(12) United States Patent
Kemnitzer et al.

(10) Patent No.: US 11,180,657 B2
(45) Date of Patent: Nov. 23, 2021

(54) POLYSULFONATED FLUORESCENCE DYES

(71) Applicant: ATTO-TEC GmbH, Siegen (DE)

(72) Inventors: Norbert Kemnitzer, Netphen (DE); Alexander Zilles, Kreuztal (DE); Karl-Heinz Drexhage, Siegen (DE); Monika Hamers-Schneider, Siegen (DE); Jutta Arden-Jacob, Zirndorf (DE)

(73) Assignee: ATTO-TEC GmbH, Siegen (DE)

( * ) Notice: Subject to any disclaimer, the term of this patent is extended or adjusted under 35 U.S.C. 154(b) by 243 days.

(21) Appl. No.: 16/145,597

(22) Filed: Sep. 28, 2018

(65) Prior Publication Data

US 2019/0100653 A1 Apr. 4, 2019
US 2019/0322870 A2 Oct. 24, 2019

(30) Foreign Application Priority Data

Sep. 29, 2017 (EP) .................... 17194195

(51) Int. Cl.
| | |
|---|---|
| C09B 1/34 | (2006.01) |
| C07D 311/88 | (2006.01) |
| C07C 301/00 | (2006.01) |
| C07C 309/31 | (2006.01) |
| C07C 323/62 | (2006.01) |
| C07D 405/10 | (2006.01) |
| C07D 471/04 | (2006.01) |
| C07C 13/00 | (2006.01) |
| C07F 7/08 | (2006.01) |
| C07D 215/10 | (2006.01) |
| C09B 5/42 | (2006.01) |
| C09B 57/02 | (2006.01) |
| G01N 21/64 | (2006.01) |

(52) U.S. Cl.
CPC ............... *C09B 1/34* (2013.01); *C07C 13/00* (2013.01); *C07C 301/00* (2013.01); *C07C 309/31* (2013.01); *C07C 323/62* (2013.01); *C07D 215/10* (2013.01); *C07D 311/88* (2013.01); *C07D 405/10* (2013.01); *C07D 471/04* (2013.01); *C07F 7/081* (2013.01); *C09B 1/346* (2013.01); *C09B 5/42* (2013.01); *C09B 57/02* (2013.01); *G01N 21/6428* (2013.01)

(58) Field of Classification Search
CPC .. C09B 1/34; C09B 1/346; C09B 5/42; C09B 57/02; C09B 11/24
See application file for complete search history.

(56) References Cited

U.S. PATENT DOCUMENTS

| | | | | |
|---|---|---|---|---|
| 7,935,822 | B2 * | 5/2011 | Arden-Jacob | C07H 21/00 546/48 |
| 8,785,637 | B2 * | 7/2014 | Arden-Jacob | C07H 21/00 546/48 |
| 8,846,924 | B2 * | 9/2014 | Zilles | C07D 215/20 546/61 |
| 2004/0260093 | A1 | 12/2004 | Czerney et al. | |
| 2006/0179585 | A1 | 8/2006 | Zilles et al. | |
| 2018/0118943 | A1 | 5/2018 | Hanaoka et al. | |

FOREIGN PATENT DOCUMENTS

| | | | |
|---|---|---|---|
| CN | 1810812 | * | 8/2006 |
| EP | 2192198 A1 | | 6/2010 |
| EP | 3219712 A1 | | 9/2017 |
| WO | 2005003086 A2 | | 1/2005 |
| WO | 2013152687 A1 | | 10/2013 |
| WO | 2015175870 A1 | | 11/2015 |
| WO | 2016157937 A1 | | 10/2016 |

* cited by examiner

*Primary Examiner* — Jezia Riley
(74) *Attorney, Agent, or Firm* — Kilpatrick Townsend & Stockton LLP

(57) ABSTRACT

The invention relates to compounds of the general formulae (I)-(IV), which are characterized by substituents B comprising one or more sulfonic acid groups and their use as marker groups for the detection of analytes.

15 Claims, 18 Drawing Sheets

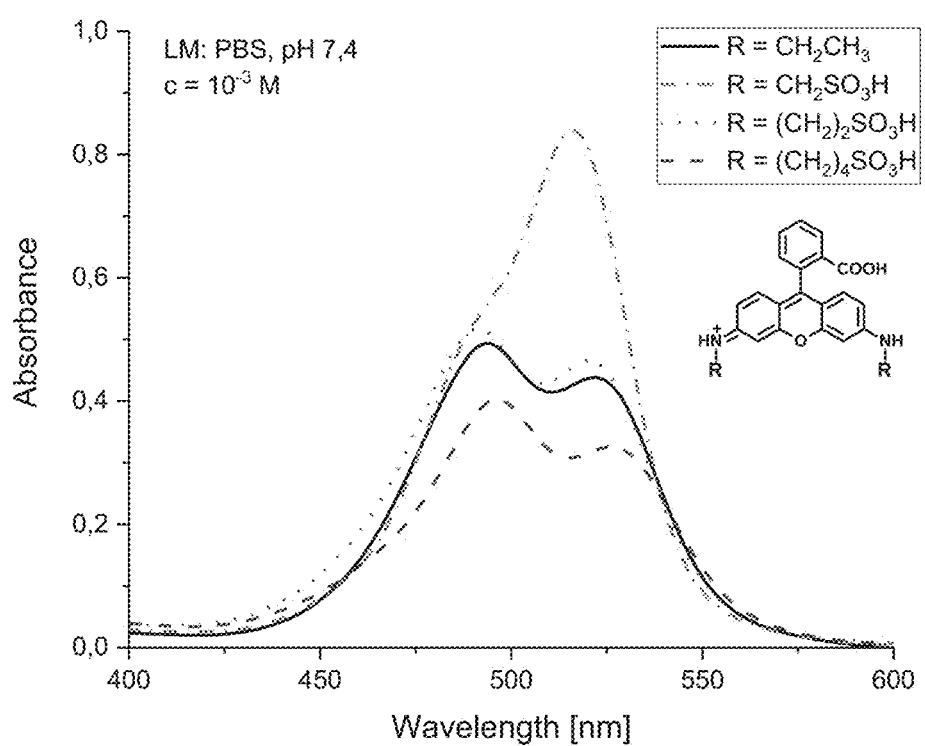
Figure 1: Absorption spectra of alkyl sulfonic acid-rhodamines in comparison with N,N'-diethyl rhodamine (R = CH$_2$CH$_3$) in PBS-buffer at 25 °C and a concentration of c = 10$^{-3}$ mol/l.

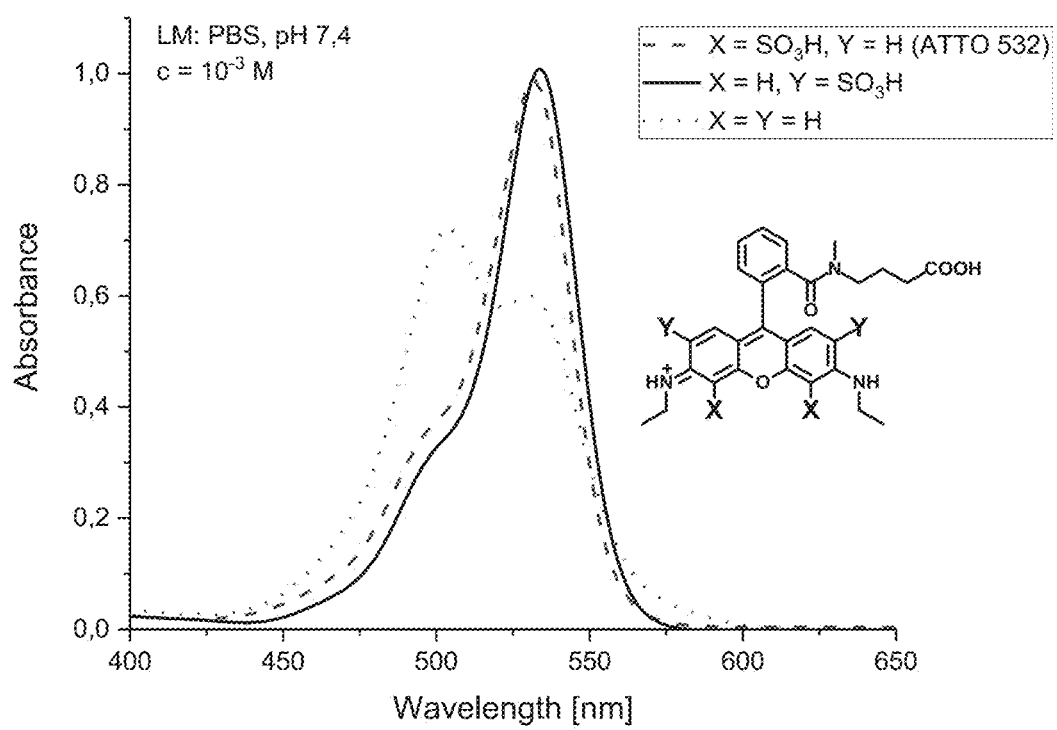
Figure 2: Absorption spectra of rhodamines directly sulfonated on the chromophore in comparison with unsulfonated dye in PBS-buffer at 25 °C and a concentration of $c = 10^{-3}$ mol/l.

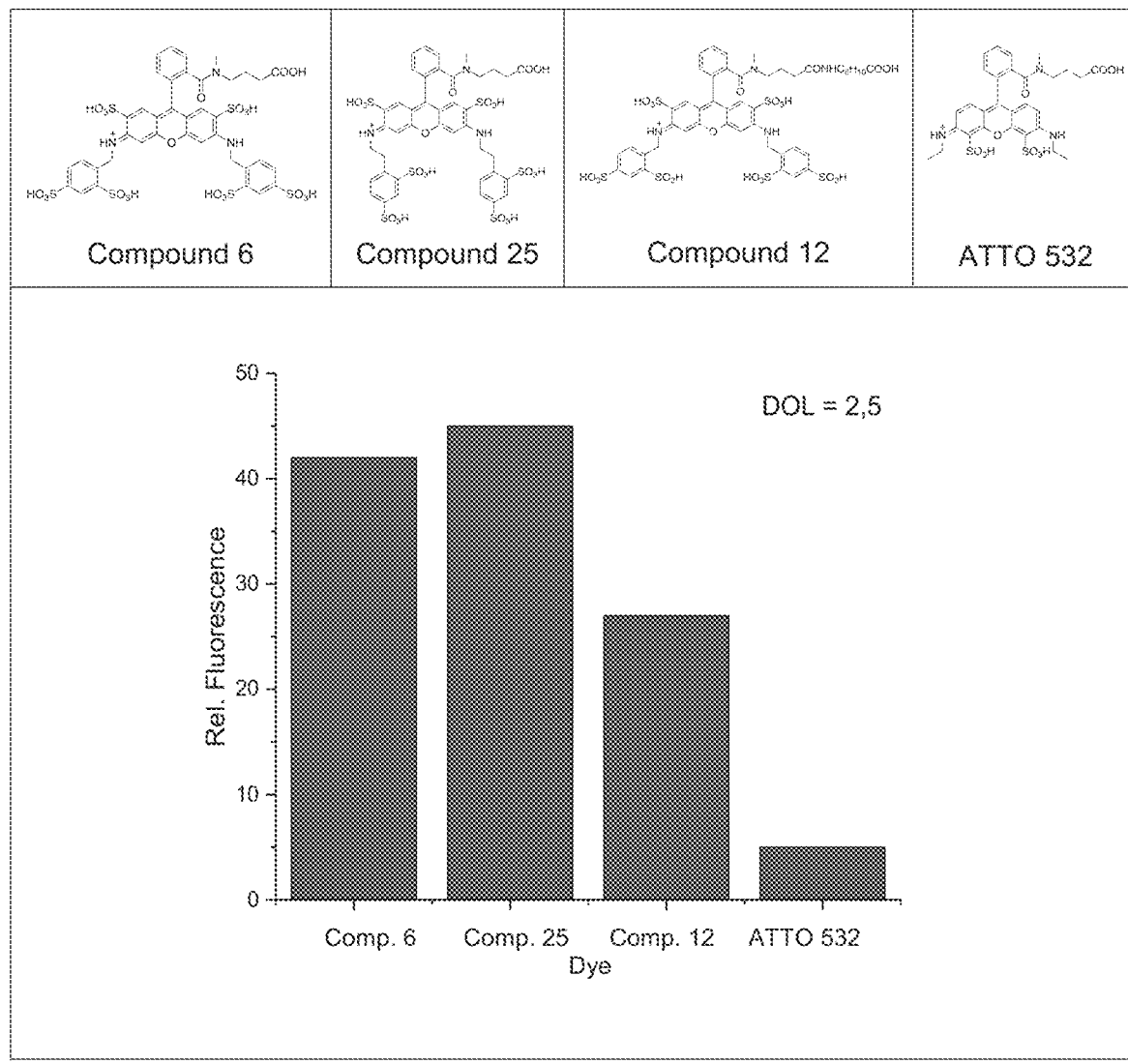
Figure 3: Fluorescence quantum yield of some dyes containing sulfonic acid groups in streptavidin-conjugate with the same DOL in PBS-buffer at 25 °C.

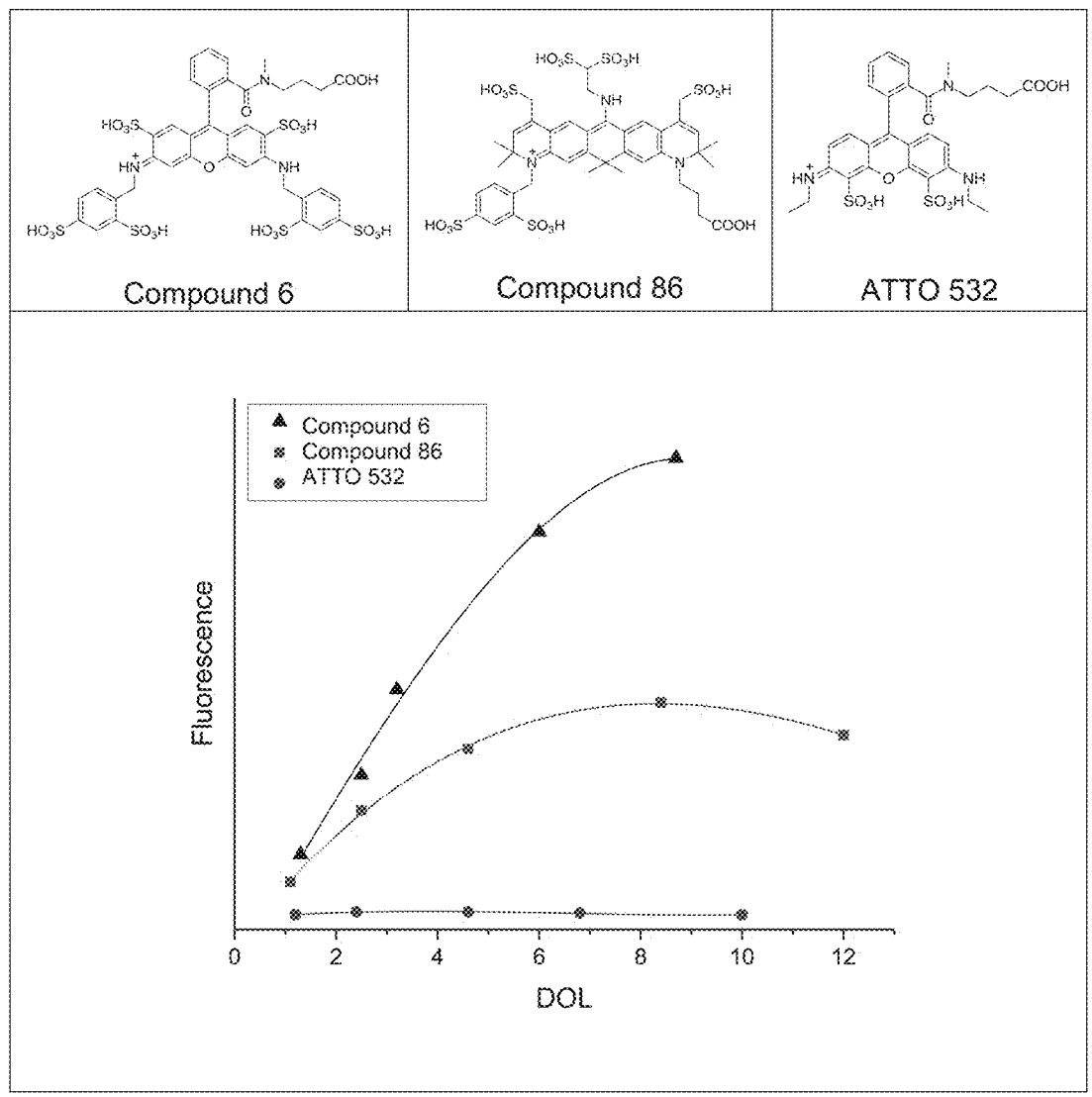
Figure 4: Relative fluorescence quantum yield of the streptavidin-conjugates of some dyes containing sulfonic acid groups at different DOLs in PBS-buffer at 25 °C.

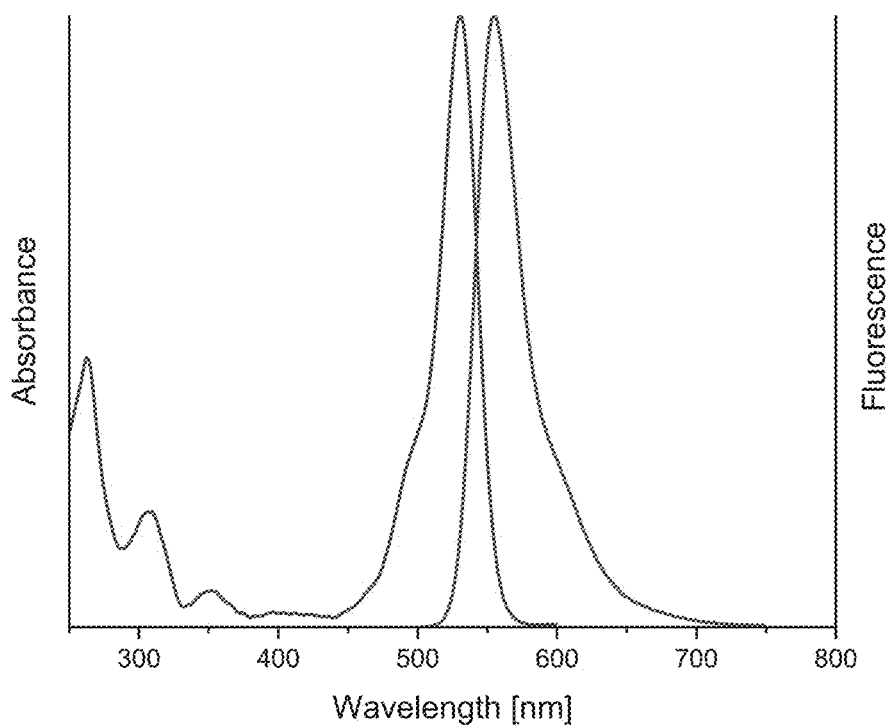
Figure 5: Absorption und fluorescence of Compound 6 in PBS-buffer at 25 °C.

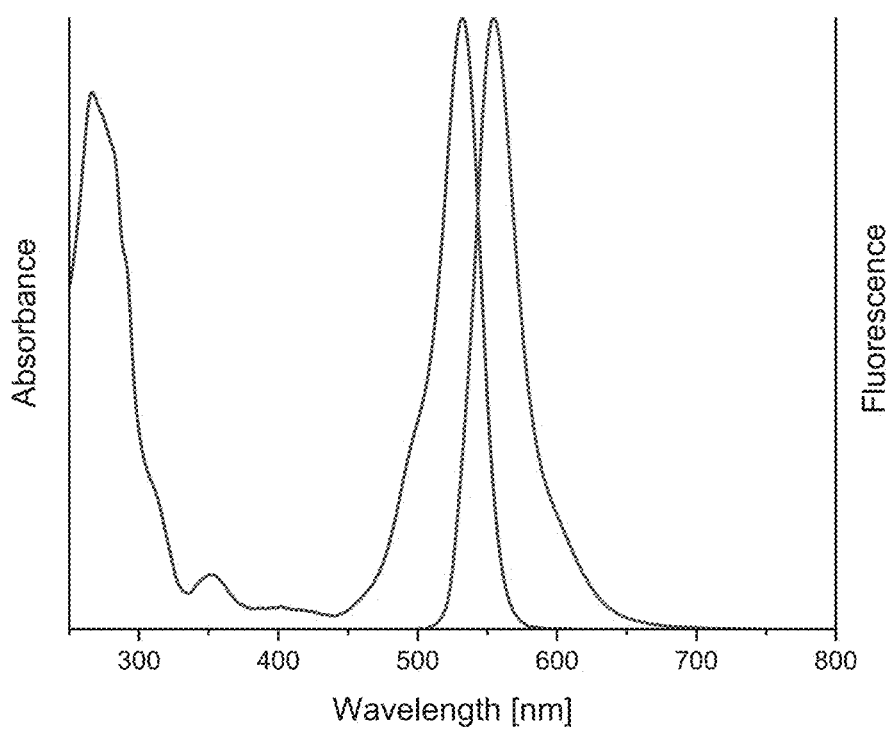
Figure 6: Absorption und fluorescence of compound 8 in PBS-buffer at 25 °C.

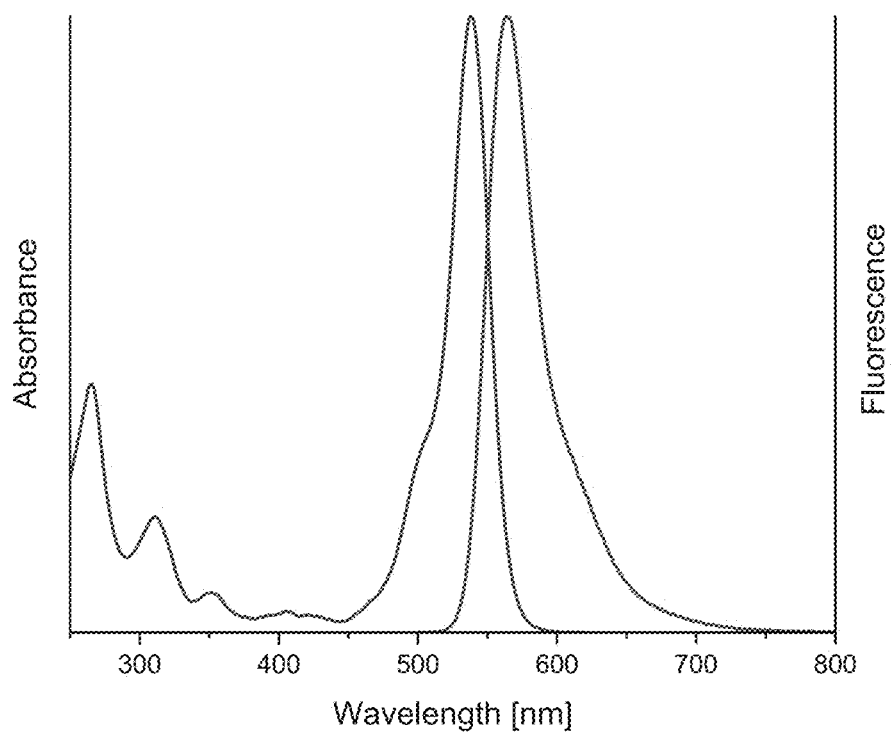
Figure 7: Absorption und fluorescence of compound 25 in PBS-buffer at 25 °C.

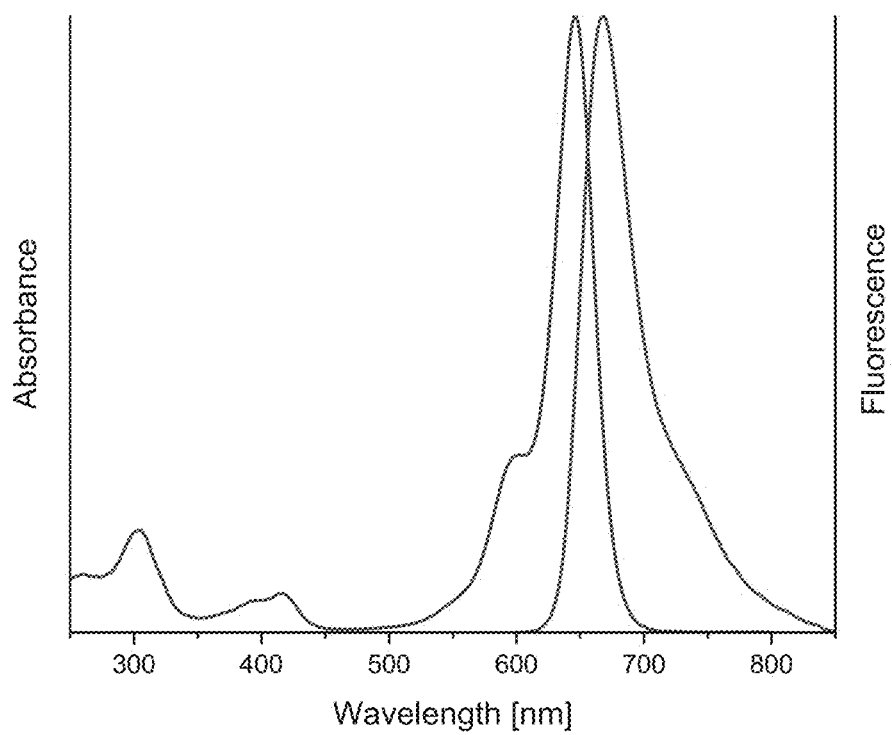
Figure 8: Absorption und fluorescence of compound 38 in PBS-buffer at 25 °C.

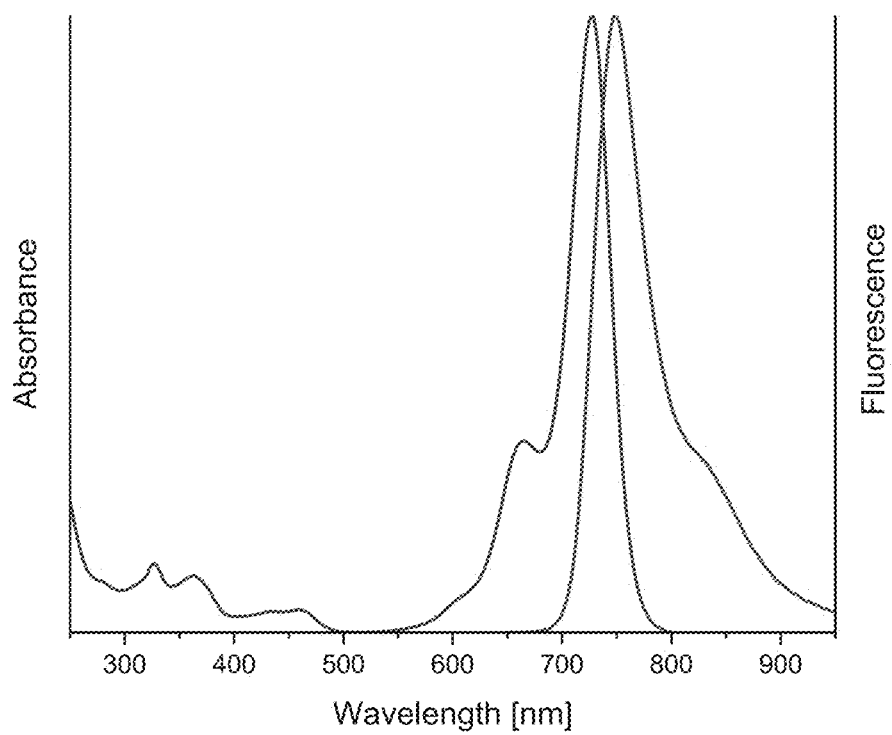
Figure 9: Absorption und fluorescence of compound 55 in PBS-buffer at 25 °C.

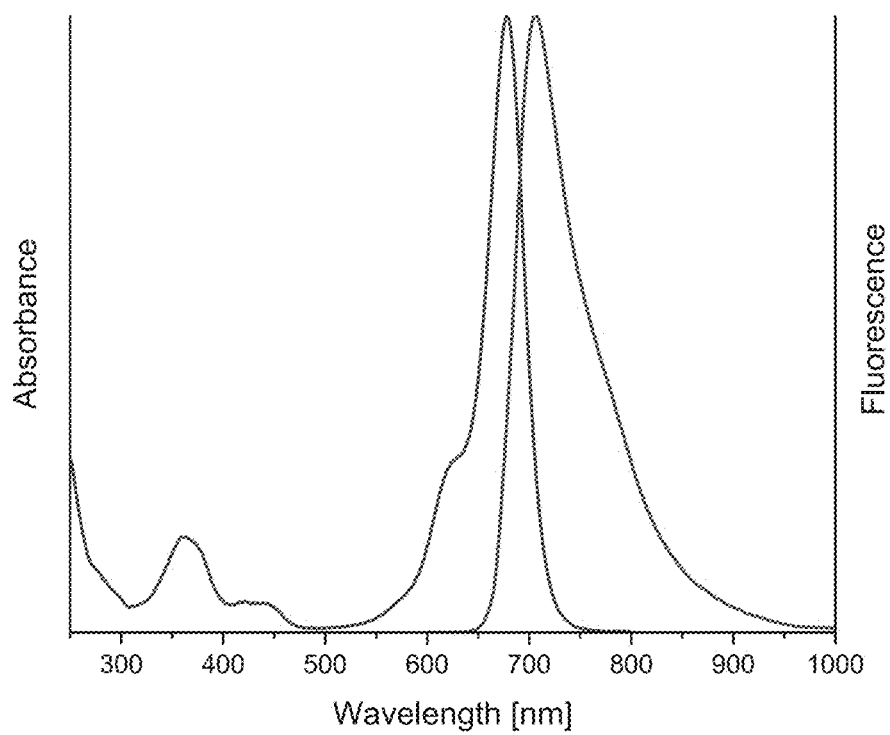
Figure 10: Absorption und fluorescence of compound 67 in PBS-buffer at 25 °C.

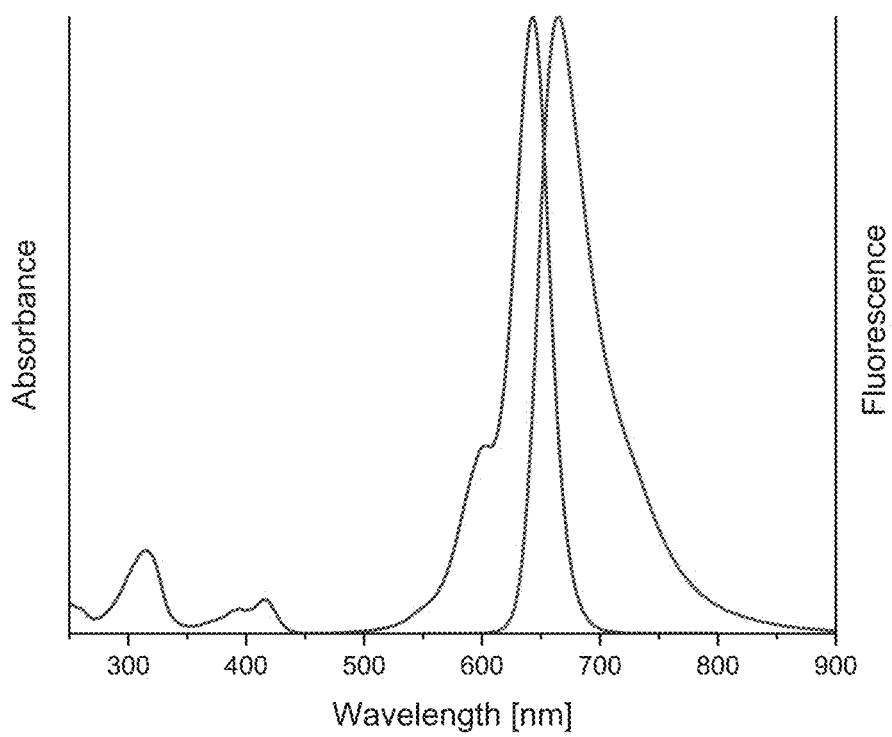
Figure 11: Absorption und fluorescence of compound 68 in PBS-buffer at 25 °C.

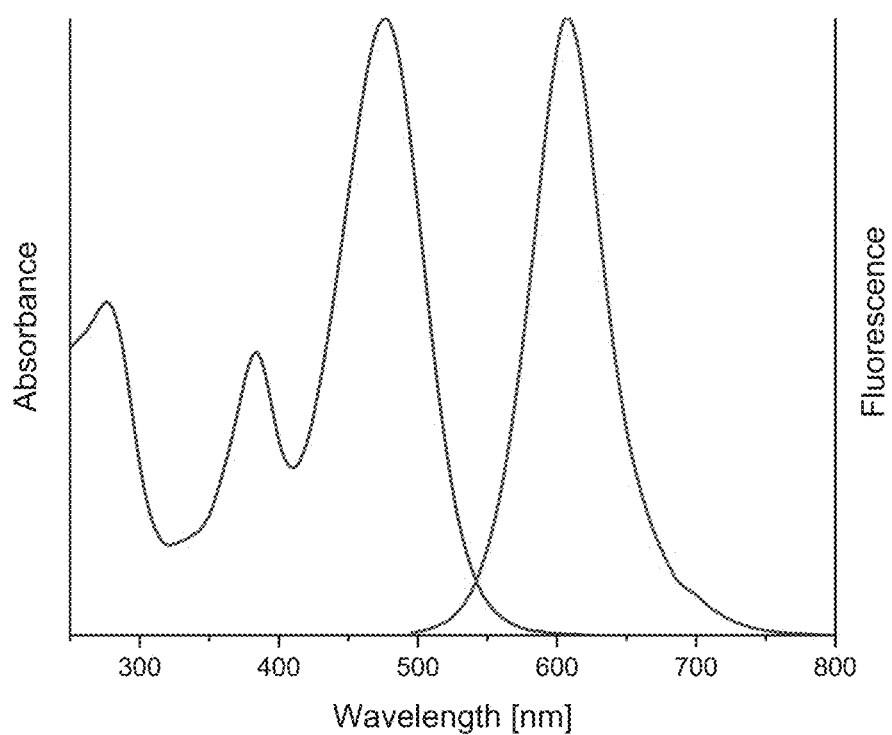
Figure 12: Absorption und fluorescence of compound 81 in PBS-buffer at 25 °C.

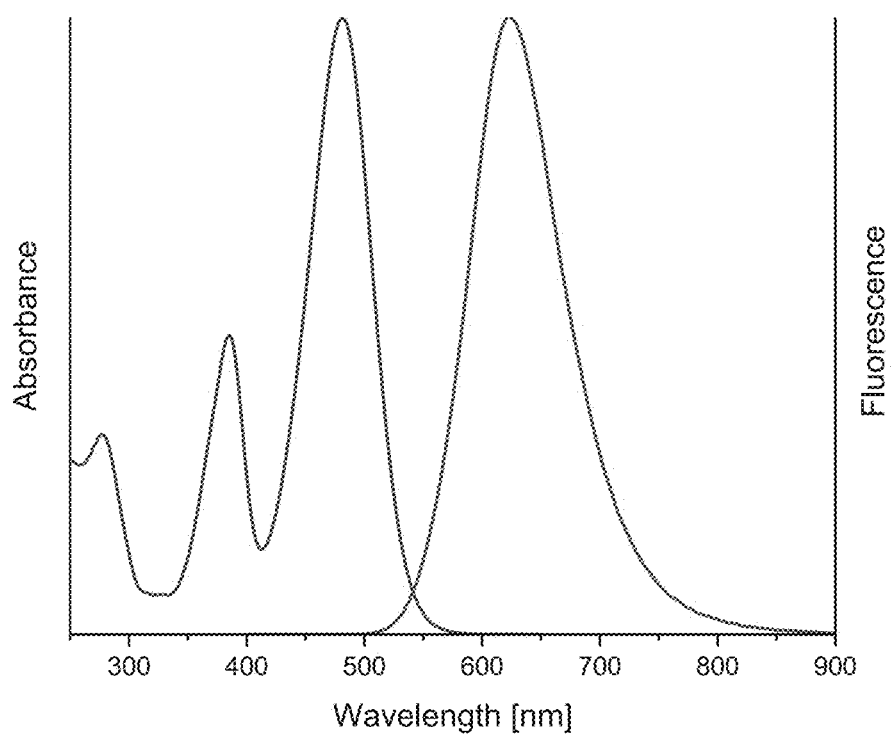
Figure 13: Absorption und fluorescence of compound 86 in PBS-buffer at 25 °C.

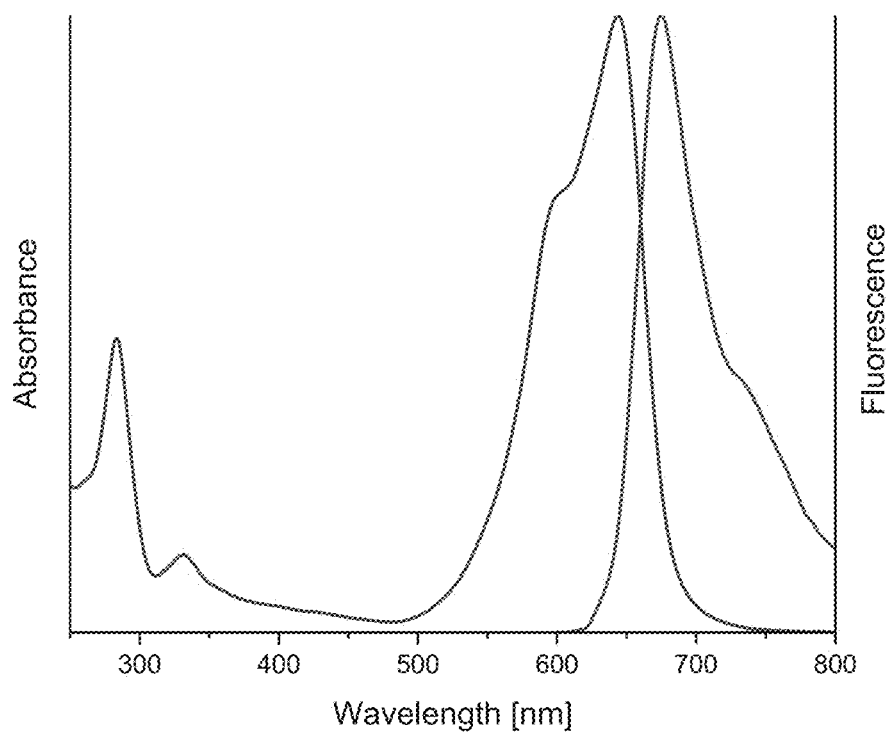
Figure 14: Absorption und fluorescence of compound 101 in PBS-buffer at 25 °C.

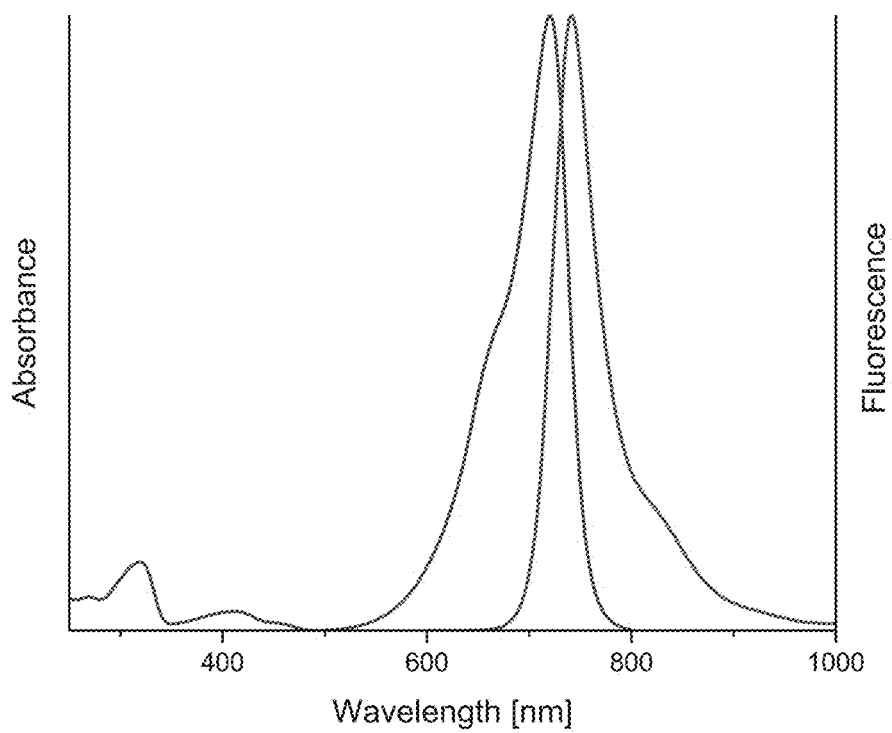
Figure 15: Absorption und fluorescence of compound 102 in PBS-buffer at 25 °C.

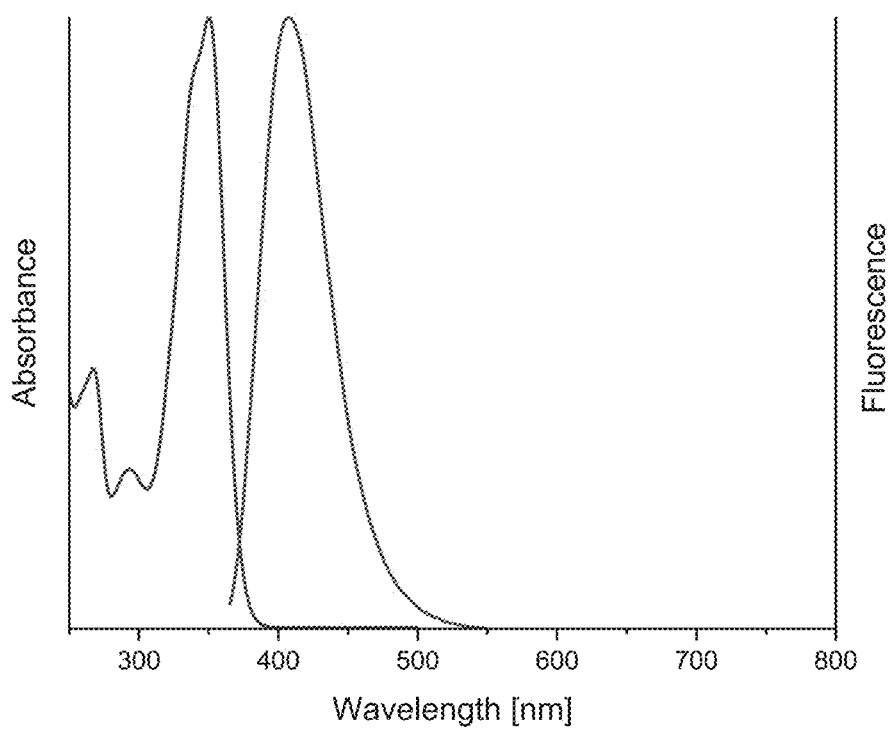
Figure 16: Absorption und fluorescence of compound 106 in PBS-buffer at 25 °C.

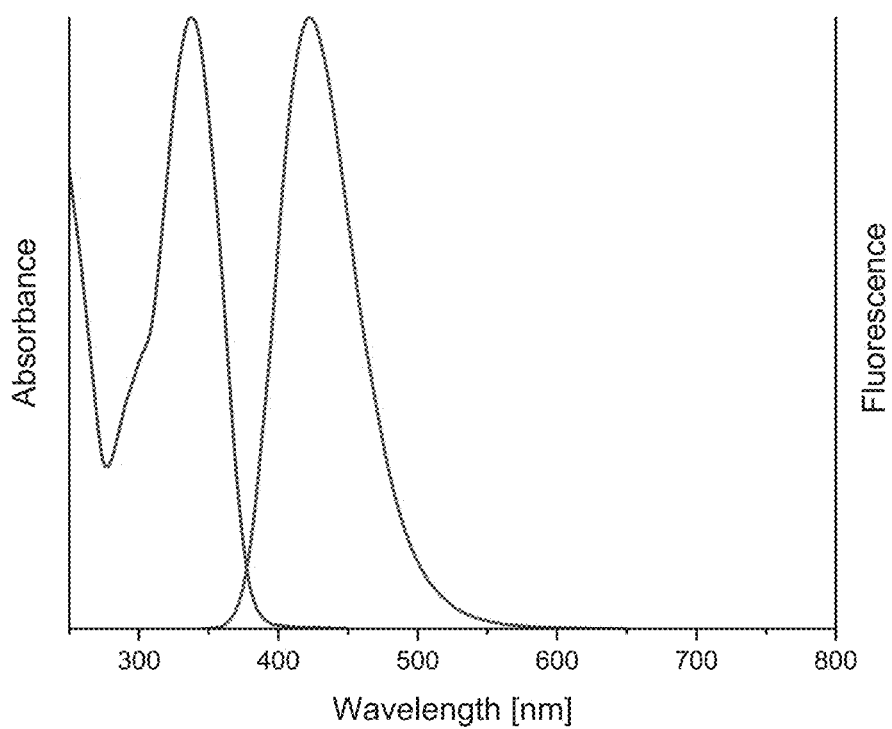
Figure 17: Absorption und fluorescence of compound 113 in PBS-buffer at 25 °C.

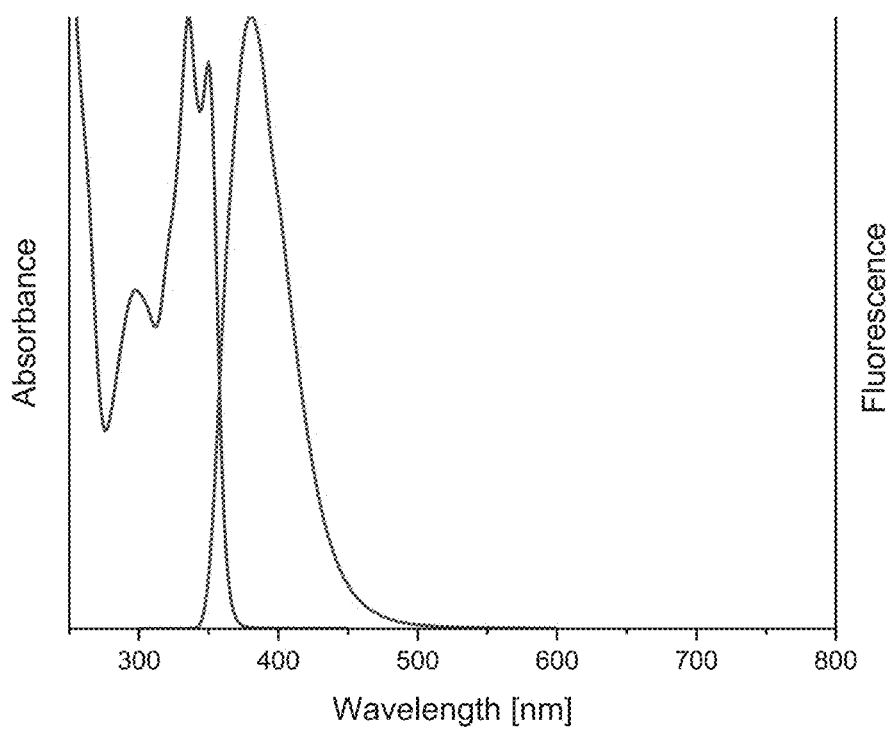
Figure 18: Absorption und fluorescence of compound 115 in PBS-buffer at 25 °C.

POLYSULFONATED FLUORESCENCE DYES

CROSS REFERENCE TO RELATED APPLICATION

This application claims priority to European Patent Application No. 17 194 195.8, filed in Europe on Sep. 29, 2017, the entire contents of which are hereby incorporated herein by this reference.

SUMMARY

The invention relates to compounds of general formulae (I)-(IV) which are characterized by substituents B containing one or more sulfonic acid groups and their use as marker groups for the detection of analytes.

In chemical, medical, and biological analytics, organic dyes are used in diverse ways as marker or detector groups. In particular fluorescence dyes have recently acquired great practical importance and have nearly supplanted other previous methods, which use radioactive isotopes, for instance. One particular advantage of fluorescence methods is the great detection sensitivity: Due to their fluorescence, even individual molecules can be detected. In comparison with radioactive methods, the stability of the labels and the simpler safety regulations are substantial advantages in practical application.

Most of these analytical marking and detection methods are carried out in an aqueous milieu. Due to the low water solubility of many organic dyes used as markers a number of problems result: The non-specific binding of the fluorophore to vessel walls or substrates and the strong tendency to form non-fluorescing dye aggregates are disruptive phenomena.

In practice non-specific binding leads to increased background fluorescence and thus to greatly reduced detection reliability. Along with the dye molecules covalently bound to the analyte to be detected (desired fluorescence labeling), fluorophores are also excited that are only absorbed by weaker interactions on surfaces, or are associated with other than the desired analytes—thus not covalently bound. If the affinity between the involved species is great enough, the obligatory washing steps do not lead to complete removal of the dye molecules non-specifically bound in this manner. These fluorophores then create a disruptive additional fluorescence signal which distorts the actual detection.

The occurrence of dye aggregates may be seen in the absorption spectrum through a major change in the longwave absorption band (so-called aggregate spectrum). This phenomenon can be observed very often in sufficiently concentrated aqueous dye solutions, whereas it normally does not occur in organic solvents.

The causes of aggregate formation are above all hydrophobic interactions between the dye chromophores and the surrounding water molecules. It is more energy-favorable when two (or more) dye molecules assemble as an aggregate. The associated change in the electron energy levels is reflected by the changed absorption spectrum.

In contrast to the fluorescence dyes present as monomers, however, dye aggregates are practically always non-fluorescing. Use as a fluorescence marker is no longer efficiently possible under these circumstances, as the sensitivity and thus the detection limit drop sharply or the image quality suffers significantly.

The described phenomenon of aggregation of dyes in aqueous solution also appears as a disruptive factor at another point: In order to increase detection reliability, it is desirable to couple as many fluorescence dye molecules as possible to a single biomolecule for marking. It is expected that the fluorescence intensity of the individual molecules hereby adds up and thus leads to a signal increase.

BRIEF DESCRIPTION OF THE DRAWINGS

FIG. 1 shows absorption spectra of alkyl sulfonic acid-rhodamines in comparison with N,N'-diethyl rhodamine ($R=CH_2CH_3$) in PBS-buffer at 25° C. and a concentration of $c=10^{-3}$ mol/l.

FIG. 2 shows absorption spectra of rhodamines directly sulfonated on the chromophone in comparison with unsulfonated dye in PBS-buffer at 25° C. and a concentration of $c=10^{-3}$ mol/l.

FIG. 3 shows fluorescence quantum yield of some dyes containing sulfonic acid groups in streptavidin-conjugate with the same DOL in PBS-buffer at 25° C.

FIG. 4 shows relative fluorescence quantum yield of the streptavidin-conjugates of some dyes containing sulfonic acid groups at different DOLs in PBS-buffer at 25° C.

FIG. 5 shows absorption and fluorescence of Compound 6 in PBS-buffer at 25° C.

FIG. 6 shows absorption and fluorescence of compound 8 in PBS-buffer at 25° C.

FIG. 7 shows absorption and fluorescence of compound 25 in PBS-buffer at 25° C.

FIG. 8 shows absorption and fluorescence of compound 38 in PBS-buffer at 25° C.

FIG. 9 shows absorption and fluorescence of compound 55 in PBS-buffer at 25° C.

FIG. 10 shows absorption and fluorescence of compound 67 in PBS-buffer at 25° C.

FIG. 11 shows absorption and fluorescence of compound 68 in PBS-buffer at 25° C.

FIG. 12 shows absorption and fluorescence of compound 81 in PBS-buffer at 25° C.

FIG. 13 shows absorption and fluorescence of compound 86 in PBS-buffer at 25° C.

FIG. 14 shows absorption and fluorescence of compound 101 in PBS-buffer at 25° C.

FIG. 15 shows absorption and fluorescence of compound 102 in PBS-buffer at 25° C.

FIG. 16 shows absorption and fluorescence of compound 106 in PBS-buffer at 25° C.

FIG. 17 shows absorption and fluorescence of compound 113 in PBS-buffer at 25° C.

FIG. 18 shows absorption and fluorescence of compound 115 in PBS-buffer at 25° C.

DETAILED DESCRIPTION

The average number of dye molecules per biomolecule is expressed by the "degree of labeling" (DOL). The method of DOL determination is known to a person skilled in the art: Toward this end, the absorptions of the dye-biomolecule-conjugate at the absorption maximum of the dye, where the biomolecule does not absorb, and in UV at 260 nm (for DNA) or 280 nm (for proteins) are obtained. Since the dye also absorbs in UV, the (total) absorption measured there must still be corrected with the absorption of the dye at this wavelength in order to obtain the actual biomolecule absorption. For this purpose, with commercial dyes, so-called CF values (correction factor values) are given, which describe the ratio of absorptions of the dye at the longwave maximum and at 260 nm or 280 nm.

From the thus obtained (individual) absorptions of dye and biomolecule in the conjugate, taking into consideration the two extinction coefficients, the quotient is formed, which directly indicates the molecular concentration ratio and thus the mean number of dye molecules per biomolecule ("degree of labeling," DOL).

The result of an increase in the DOL can be that the dyes covalently bound to the biomolecule are in close spatial proximity, and thus here as well aggregation phenomena can be observed. In such cases, one does not obtain, as may be expected, an ever increasing increase in the fluorescence signal. Rather, generally a kind of saturation is reached already at one or a few dye molecules per biomolecule, in which the detected fluorescence does not increase further. If the DOL is still higher, even a decrease in fluorescence intensity may be observed.

It was therefore an object of the present invention to provide fluorescence dyes that can be used as a marker group in analyte detection procedures, and which at least partially avoid these disadvantages of the prior art. In particular, it was an object of the present invention to provide fluorescence dyes that display as little as possible non-specific binding to vessel walls or to substrates different from the analyte. It was a further object to provide fluorescence dyes that show as little as possible or no aggregate formation in an aqueous environment.

It is known that hydrophobic organic compounds are more readily soluble in water by substitution with hydrophilic or ionic groups, e.g. sulfonic acid groups. In general this leads to a reduction in the hydrophobic interaction of the molecules with one another, which, as explained above, in organic dyes minimizes the aggregation tendency, so that once again a higher fluorescence signal can be expected.

The effectiveness of such a substitution as regards the desired fluorescence properties, however, is dependent on the type (directly on the chromophore or via a linker) and on the location (position in the molecule) of the connection of the sulfonic acids and on their total quantity.

This was shown exemplarily on cyanine dyes by J. Pauli, M. Grabolle, R. Brehm, M. Spieles, F. Hamann, M. Wenzel, I. Hilger, and U. Resch-Genger, Suitable Labels for Molecular Imaging—Influence of Dye Structure and Hydrophilicity on the Spectroscopic Properties of IgG Conjugates, Bioconjugate Chem., 2011, 22, 1298-1308 and J. Pauli, K. Licha, J. Berkemeyer, M. Grabolle, M. Spieles, N. Wegner, P. Welker, and U. Resch-Genger, New Fluorescent Labels with Tunable Hydrophilicity for the Rational Design of Bright Optical Probes for Molecular Imaging, Bioconjugate Chem., 2013, 24, 1174-1185, and F. M Hamann, R. Brehm, J. Pauli, M. Grabolle, W. Frank, W. A. Kaiser, D. Fischer, U. Resch-Genger, and I. Hilger, Controlled modulation of serum protein binding and biodistribution of asymmetric cyanine dyes by variation of the number of sulfonate groups, Molecular imaging, 2011, 10, 258-269.

For rhodamine dyes, we ourselves were able to make similar observations:

If there are sulfonic acid groups on alkyl chains of the terminal nitrogens of the dyes, with increasing distance of these hydrophilic groups from the chromophore, their aggregation inhibiting effect decreases drastically (FIG. 1). Thus the absorption spectra of equally concentrated aqueous solutions (PBS buffer: phosphate-buffered saline) of the dyes with ethyl groups or sulfoethyl groups show about the same aggregation. Under identical conditions, only in the case of the sulfomethyl groups does one recognize a reduced aggregation in the absorption spectrum. Rhodamine dyes with such simple sulfoalkyl groups are however patented for their better water solubility, see for example C. Barnes, N. N. Romanov, Illumina Cambridge Limited, Dye compounds and the use of their labelled conjugates, U.S. Pat. No. 8,178,360B2.

On the other hand, direct substitution with sulfonic acid groups on the chromophore, in addition to the increase in water solubility, also brings about a massive reduction in aggregation (FIG. 2). In the sulfonated dyes, the narrow monomer band still appears even in concentrated solution, while the unsubstituted dye shows a significant dimer band.

In neither of the two discussed cases (sulfoalkyl-substitution of the terminal nitrogens or direct sulfonic acid group substitution on the chromophore), in the coupling to the model protein streptavidin chosen by us because of its wide prevalence in biochemical procedures such as protein purification or immune assays, is the high fluorescence quantum yield of the free dyes maintained, despite increased water solubility and possibly reduced aggregation, see Table 1, example ATTO 532. With such dyes, the quantum yield in the conjugate is markedly reduced in comparison with the free uncoupled dye.

The limited availability of direct connection sites on the molecule is a further disadvantage of the previously described sulfonation of rhodamines. In this manner therefore only a small quantity of sulfonic acid groups can be incorporated in the dye, usually a maximum of two. In this regard, see e.g. F. Mao, W.-Y. Leung, Richard P. Haugland, Molecular Probes Inc., Sulfonated Xanthene Derivatives, U.S. Pat. No. 6,130,101A or R. L. Cournoyer, J. W. Foley, Polaroid Corporation, Photographic Products and Processes with a pH sensitive Xanthene Light Screening Dye, U.S. Pat. No. 4,345,017A.

In the case of the oxazines, sulfonic acid groups may even be incorporated only via alkyl chains on the molecule periphery: A. Toutchkine, Sigma-Aldrich Co., Oxazine dyes with improved aqueous solubility, United States Patent Application US2012/0010404A1.

It was therefore a further object of the present invention to incorporate even more sulfonic acid groups in dyes than is possible according to the prior art.

The preferred dyes are representatives of the following classes compiled below—but not limited to these, with the general structures:

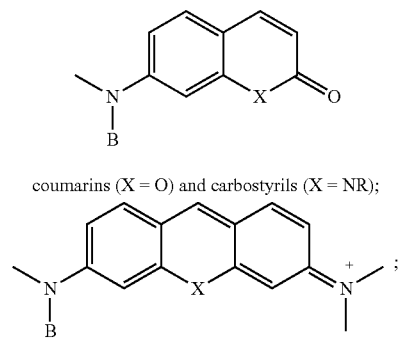

coumarins (X = O) and carbostyrils (X = NR);

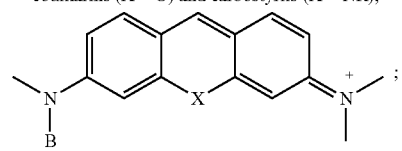

acridines (X = NR), xanthene dyes
thiopyronines/-rhodamines (X = S)
carbopyronines/-rhodamines (X = CR$_2$)
silicopyronines/-rhodamines (X = SiR$_2$)
sulfone-rhodamines (X = SO$_2$)

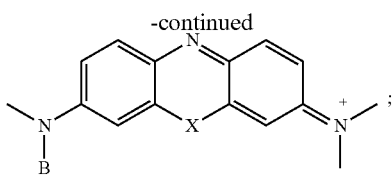

azine dyes: oxazines (X = O)
thiazines (X = S), carbazines (X = CR$_2$)

Via the moiety B substituents comprising at least one sulfonic acid group are introduced.

This object was achieved by compounds of the general formulae (I)-(IV) and their use as marker groups in a procedure for detecting an analyte.

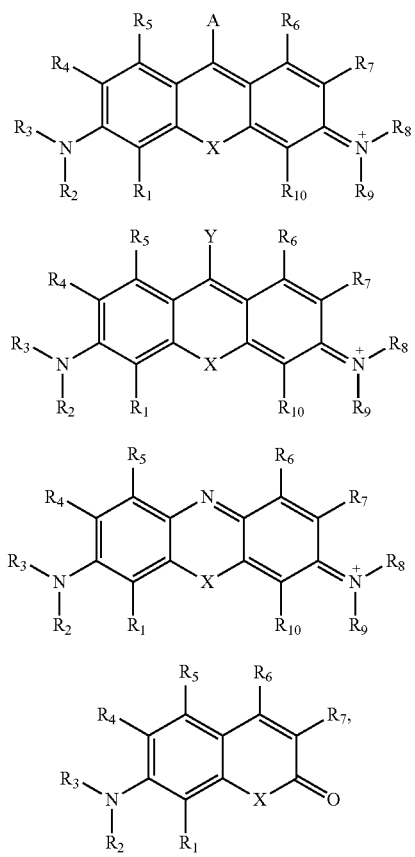

in which $R_1$, $R_4$, $R_5$, $R_6$, $R_7$, and $R_{10}$ independently of one another mean hydrogen, halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$, SO$_3$H or a hydrocarbon group having 1-20 C atoms, wherein the hydrocarbon group optionally comprises one or more heteroatoms selected from the group consisting of N, O, and S or/and one or more substituents preferably selected from the group consisting of halogen, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H, $R_2$, $R_3$, Ra, and $R_9$ independently of one another mean hydrogen or a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H, wherein each of the moieties in the compounds of the general formulae (I)-(IV) can form a ring system with one or more adjacent moieties, X in the general formula (I) means a group selected from O, S, SO$_2$, CR$_{11}$R$_{12}$ or SiR$_{13}$R$_{14}$, X in the general formula (II) means a group selected from O, S, CR$_{11}$R$_{12}$, SiR$_{13}$R$_{14}$ or NR$_{15}$, X in the general formula (III) means a group selected from O, S or CR$_{11}$R$_{12}$, X in the general formula (IV) means O or NR$_{15}$, and wherein $R_{11}$, $R_{12}$, $R_{13}$, $R_{14}$ and $R_{15}$ independently of one another mean hydrogen, CN, COOH, COO(alkyl), COO(aryl), PO$_3$H$_2$, SO$_3$H or a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H, or $R_{11}$ and $R_{12}$ or $R_{13}$ and $R_{14}$ in each case together with the atom to which they are attached, form a 3- to 7-membered ring, wherein the ring can comprise one or more double bonds or/and one or more heteroatoms selected from the group consisting of N, O and S or/and one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$, SO$_3$H and a hydrocarbon group having 1-20 C atoms or/and can be fused with one or more 3- to 7-membered rings, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$, and SO$_3$H, A in the general formula (I) means an aryl or heteroaryl moiety, which optionally comprises one or more substituents preferably selected from the group consisting of hydrogen, halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), CONH(alkyl), CON(alkyl)$_2$, CONH(aryl), CON(aryl)$_2$, PO$_3$H$_2$, SO$_3$H and a hydrocarbon group, wherein the hydrocarbon group itself optionally comprises one or more heteroatoms selected from the group consisting of N, O and S or/and one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H, Y in the general formula (II) means hydrogen, CN, COOH, COO(alkyl), COO(aryl), NHR$_{16}$, NR$_{17}$R$_{18}$, PO$_3$H$_2$, SO$_3$H or an aliphatic hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO (aryl), $PO_3H_2$ and $SO_3H$, and $R_{16}$, $R_{17}$, and $R_{18}$ independently of one another mean hydrogen, CN, COOH, COO(alkyl), COO(aryl), $PO_3H_2$, $SO_3H$ or a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, or $R_{17}$ and $R_{18}$ together with the atom to which they are attached, form a 3- to 7-membered ring, wherein the ring can comprise one or more double bonds or/and one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$ and a hydrocarbon group having 1-20 C atoms or/and can be fused with one or more 3- to 7-membered rings, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, provided that at least one of the moieties $R_2$, $R_3$, $R_8$ or $R_9$ has the structure B, wherein B means either an aliphatic hydrocarbon group having 1-6 C atoms, preferably 1-2 C atoms, wherein this hydrocarbon group itself optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, and which carries at least one $SO_3H$ substituent or means an aliphatic hydrocarbon group having 1-6 C atoms, preferably 1-3 C atoms, more preferably 1-2 C atoms, wherein this hydrocarbon group itself optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO (alkyl), COO(aryl), $PO_3H_2$ and $SO_3H$, and which carries at least one aryl or heteroaryl moiety, which optionally comprises one or more substituents preferably selected from the group consisting of hydrogen, halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO (aryl), CONH(alkyl), $CON(alkyl)_2$, CONH(aryl), CON$(aryl)_2$, $PO_3H_2$, $SO_3H$ and a hydrocarbon group, wherein the hydrocarbon group itself optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, and which carries at least one $SO_3H$ substituent or means an aryl or heteroaryl moiety, which optionally comprises one or more substituents preferably selected from the group consisting of hydrogen, halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO (alkyl), COO(aryl), CONH(alkyl), $CON(alkyl)_2$, CONH (aryl), $CON(aryl)_2$, $PO_3H_2$, $SO_3H$ and a hydrocarbon group, wherein the hydrocarbon group itself optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO (alkyl), COO(aryl), $PO_3H_2$ and $SO_3H$, and which carries at least one $SO_3H$ substituent or means a moiety, which is derived from cyanuric chloride and instead of one or both available Cl atoms is substituted with a moiety —$NH(CH_2)_nSO_3H$, wherein n is an integer from 1 to 6 and preferably n=2, wherein in compounds of the general formula (I) for X=O the moiety B is not —$(CH_2)_mSO_3H$ (sulfoalkyl group), wherein m is an integer from 1 to 6, unless at the same time at least one or more of the moieties $R_1$, $R_4$, $R_5$, $R_6$, $R_7$, $R_{10}$ and/or A comprises at least one further $SO_3H$ group, wherein in compounds of the general formula (IV) for X=O, moiety B, if it means an aliphatic hydrocarbon group, represents —$CH_2SO_3H$ or —$CH_2CH_2SO_3H$.

The definitions indicated for the structure B mean that the structure B does not form a ring system with one or more adjacent moieties.

The term "hydrocarbon group", as it is used in the scope of the present application, comprises a saturated or unsaturated hydrocarbon moiety having 1-20 carbon atoms, preferably 1-12 carbon atoms, more preferably 1-6 carbon atoms, which can be linear, branched, or cyclic and has a bond valence at any one of the 1-20 carbon atoms. Examples of hydrocarbon groups according to the present invention include alkyl, cycloalkyl, alkenyl or alkynyl and aryl.

If the hydrocarbon group comprises one or more heteroatoms selected from the group consisting of N, O and S, the hydrocarbon group can also be configured as a heteroalkyl, heterocycloalkyl, or heteroaryl.

The term "aliphatic hydrocarbon group", as it is used in the scope of the present application, has the same meaning as hydrocarbon group, with the exception of aryl or heteroaryl.

The term "alkyl", as it is used in the scope of the present application, designates a saturated, linear, or branched hydrocarbon moiety having 1-20 carbon atoms, which has a bond valence at any one of the 1-20 carbon atoms. Preferably alkyl constitutes a hydrocarbon moiety having 1-12 carbon atoms, more preferably having 1-6 carbon atoms. Especially preferable alkyls comprise methyl, ethyl, n-propyl, iso-propyl, n-butyl, iso-butyl, sec-butyl and tert-butyl.

If the hydrocarbon moiety comprises one or more heteroatoms selected from the group consisting of N, O and S, the moiety can be configured as a heteroalkyl and thus comprise inter alia alkoxy groups such as methoxy, ethoxy etc.

The term "cycloalkyl", as it is used in the scope of the present application, designates a saturated or unsaturated, cyclic hydrocarbon moiety having 3-20 carbon atoms, which has a bond valence at any one of the 3-20 carbon atoms. Preferably cycloalkyl constitutes a cyclic hydrocarbon moiety having 3-12 carbon atoms, more preferably having 3-8 carbon atoms. Especially preferable cycloalkyls comprise cyclopropyl, cyclobutyl, cyclopentyl, cyclohexyl, cycloheptyl, and cyclooctyl. In addition the cyclic hydrocarbon moieties can be bridged and form bicyclic or polycyclic compounds, such as norbornane, norbornene, and bicyclo[3.2.2]octyl.

If the cyclic hydrocarbon moiety comprises one or more heteroatoms selected from the group consisting of N, O and S, the moiety can also be configured as a heterocycloalkyl, and thus comprise aliphatic heterocycles such as tetrahydropyrrole, piperidine, dioxane, or tetrahydrofurane.

The term "alkenyl", as it is used in the scope of the present application, designates an unsaturated, linear, or branched hydrocarbon moiety having 2-20 carbon atoms, which has a bond valence at any one of the 2-20 carbon atoms and at least one double bond. Preferably alkenyl constitutes a hydrocarbon moiety having 2-12 carbon atoms, more preferably having 2-6 carbon atoms. Especially preferable alkenyls comprise ethenyl, propenyl and butenyl.

The term "alkynyl", as it is used in the scope of the present application, designates an unsaturated, linear, or branched hydrocarbon moiety having 2-20 carbon atoms, which has a bond valence at any one of the 2-20 carbon atoms and at least one triple bond. Preferably alkynyl constitutes a hydrocarbon moiety having 2-12 carbon atoms, more preferably having 2-6 carbon atoms. Especially preferable alkynyls comprise ethynyl, propynyl and butynyl.

The term "aryl", as it is used in the scope of the present application, designates an aromatic ring system having 3-20 ring atoms, more preferably having 6-14 ring atoms, which as ring atoms contains only carbon atoms and has a bond valence at any one of the carbon atoms of the 3-20 ring-forming atoms. Preferable aryls comprise phenyl, naphthyl, anthracenyl, and phenanthrenyl.

The term "heteroaryl", as it is used in the scope of the present application, designates an aromatic ring system having 3-20 ring atoms, more preferably having 5-14 ring atoms, which as ring atoms, apart from carbon atoms contains at least one heteroatom selected from the group consisting of N, O and S and has a bond valence at any one of the carbon atoms or nitrogen atoms of the 3-20 ring-forming atoms. Preferable heteroaryls comprise furanyl, imidazolyl, isothiazolyl, isoxazolyl, oxadiazolyl, oxazolyl, pyrazolyl, pyrrolyl, tetrazolyl, thiadiazolyl, thiazolyl, thienyl, triazolyl, pyrazinyl, pyridazinyl, pyridyl, pyrimidinyl, and triazinyl.

The term "halogen", as it is used in the scope of the present application, comprises fluorine, chlorine, bromine, and iodine.

The compounds according to the invention have at least one group B, which contains a sulfonic acid group (—$SO_3H$), bound to a nitrogen atom of the chromophore system, thus in position $R_2$, $R_3$, $R_8$ and/or $R_9$. According to the invention it was found that by incorporation of sulfonic acid group-containing moieties at these positions, fluorescence dyes can be provided, which show a markedly reduced and in particular no non-specific binding to vessel walls and no binding to substrates different from the desired analyte. Furthermore, the compounds according to the invention do not form non-fluorescent dye aggregates even in aqueous solutions. In this way it is possible to use a high mean number of dye molecules per analyte molecule (DOL) without this leading to undesired aggregation phenomena and thus to an undesired saturation. Furthermore, through the incorporation of sulfonic acid groups in the moieties $R_2$, $R_3$, $R_8$ and/or $R_9$, the incorporation of a large number of sulfonic acid groups in the compounds according to the invention is possible.

Especially good results are obtained, when the group B comprises an aromatic sulfonic acid group. Preferable examples of B in the compounds according to the invention of the general formulae (I)-(IV) include the following structures (H), (I) or (J), wherein the invention is not only restricted to the shown aryl systems, and also includes other than the shown constitutional isomers:

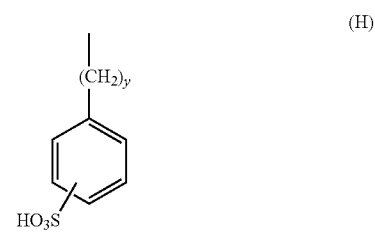

(H)

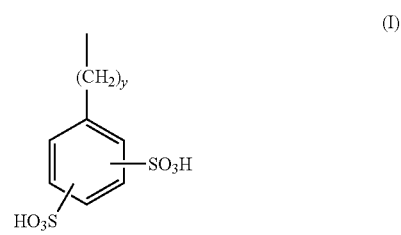

(I)

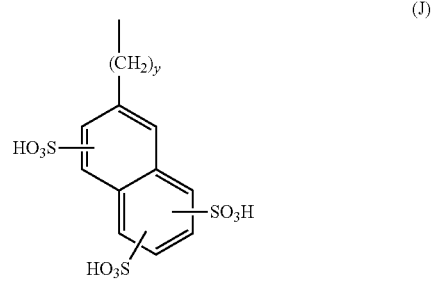

(J)

with y=0, 1, 2, 3, 4, 5, 6, preferably y=0, 1 or 2, more preferably y=1 or 2, even more preferably y=1 and wherein positions not further specified are defined as $R_1$.

Especially preferably, the group B, which constitutes one or more of the moieties $R_2$, $R_3$, $R_8$ and/or $R_9$, is a moiety selected from

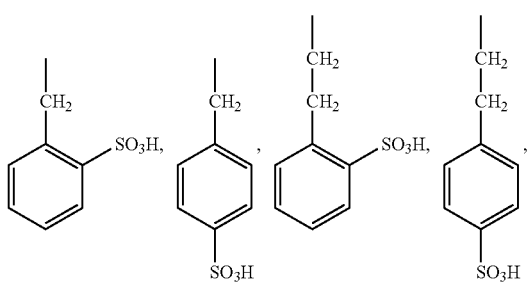

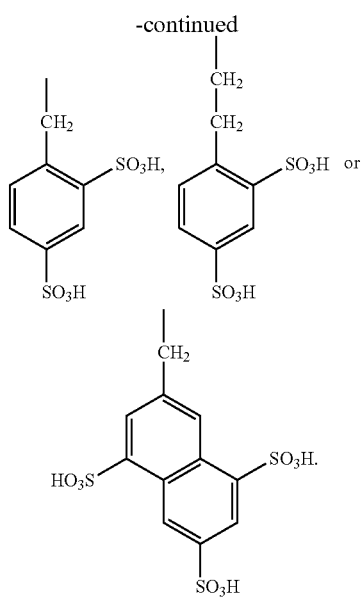

In addition, B may represent one of the structures (K) or (L) derived from cyanuric chloride with x=1, 2, 3, 4, 5, 6 preferably x=1 or 2, more preferably x=2.

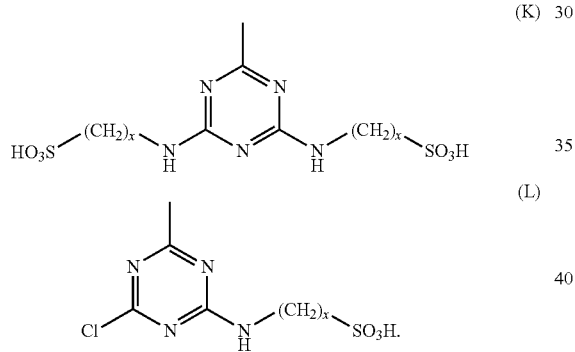

In a further preferred embodiment the group B represents —CH$_2$SO$_3$H or —CH$_2$CH$_2$SO$_3$H, even more preferably —CH$_2$—SO$_3$H.

Preferable meanings of R$_2$, R$_3$, Ra and/or R$_9$, as far as these moieties do not contain a sulfonic acid group, are hydrogen, —CH$_3$, —CH$_2$CH$_3$ and —CH$_2$CH$_2$CH$_2$COOH.

The moieties R$_1$, R$_4$, R$_7$ and/or R$_{10}$ in the compounds of the formulae (I)-(IV) are preferably hydrogen or —SO$_3$H. By one or more —SO$_3$H groups in these positions the total number of sulfonic acid groups in the compounds according to the invention can be further increased.

In a preferred embodiment of the compounds according to the invention of the general formulae (I)-(IV) R$_1$ and R$_2$, R$_3$ and R$_4$, R$_7$ and R$_8$ or/and R$_9$ and R$_{10}$ together with the atoms, to which they are bound, form a 5- or 6-membered ring, with 6-membered rings being more preferred. Therein the at least one 5- or 6-membered ring can comprise one or more double bonds or/and one or more substituents, for example 1, 2, 3 or 4 substituents, which can be the same or different. The fluorescence of such compounds is especially efficient and shows only a small dependence on temperature and environmental influences. The at least one 5- or 6-membered ring can comprise one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$, SO$_3$H and a hydrocarbon group having 1-20 C atoms, preferably 1-12 C atoms, more preferably 1-6 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H. Especially preferred as substituents of the at least one 5- or 6-membered ring are hydrocarbon groups having 1-20 C atoms, in particular alkyl groups having 1-6 C atoms, wherein the hydrocarbon groups in the case of a substitution preferably comprise one or more substituents selected from the group consisting of COOH, COO(alkyl), COO(aryl) and SO$_3$H.

Especially preferable are compounds which have one or more substituents —CH$_2$—SO$_3$H on rings formed from R$_1$ and R$_2$, R$_3$ and R$_4$, R$_7$ and Ra or/and R$_9$ and R$_{10}$.

Thus further sulfonic acid groups can be incorporated in these rings, i.e. preferable embodiments include the structures (C), (D), (E), (F), or (G)

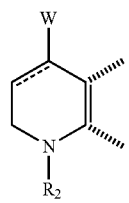

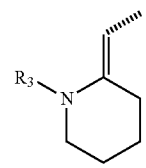

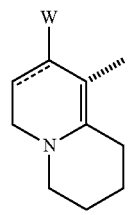

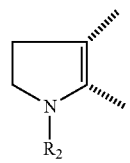

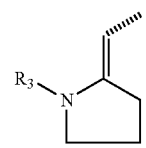

with W=H, CH$_3$ or CH$_2$SO$_3$H and wherein positions not further specified are defined in the shown ring systems as R$_1$ and the broken lines (- - -) designate optionally present double bonds. The same structures (C), (D), (E), (F) or (G) can also be present independently of one another twice in the compounds of the general formulae (I), (II) or (III), wherein then in the indicated structures $R_2$ or $R_3$ have to be replaced by $R_9$ or $R_8$, respectively.

Particularly preferable embodiments comprise the structures (C) and/or (E).

Especially preferable are compounds of the formulae (I)-(IV) comprising one of the following structures

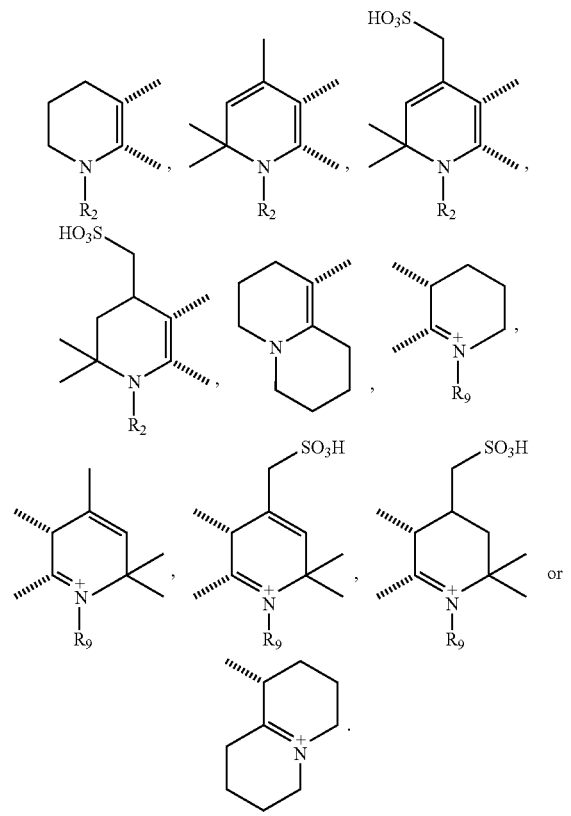

In the compounds according to the invention of the general formulae (I) and (II) X preferably means a group selected from O, $CR_{11}R_{12}$, $SiR_{13}R_{14}$ and in the general formula (III) X preferably means O, $CR_{11}R_{12}$. If X is represented by $CR_{11}R_{12}$ or $SiR_{13}R_{14}$, preferably at least one of the moieties $R_{11}$, $R_{12}$, $R_{13}$, or $R_{14}$ constitutes a hydrocarbon group having 1-20 C atoms, preferably an alkyl group having 1-6 C atoms, more preferably methyl or ethyl.

The compounds of the formula (I) comprise a moiety A. In preferred embodiments of the invention A (aryl-system, "rhodamine-like") in the general formula (I) is one of the structures (M), (N), (O), (P) or (Q)

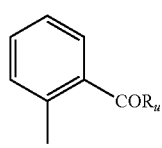

(M)

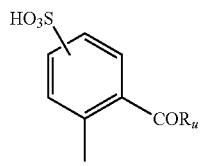

(N)

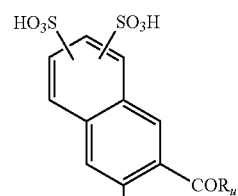

(O)

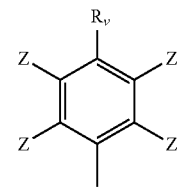

(P)

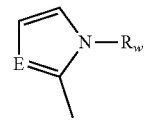

(Q)

wherein
E represents a group selected from O, S, N or $^+NR_{19}$,
$R_u$=halogen, $OR_{20}$, $NHR_{21}$, $NR_{22}R_{23}$,
Z is selected from hydrogen or halogen,
$R_v$=Z, $S(CH_2)_xCOOH$, $S(CH_2)_xSO_3H$, $NHR_{24}$, $NR_{25}R_{26}$ and
$R_w$=H, alkyl, $(CH_2)_xCOOH$, $(CH_2)_xSO_3H$ with x=1, 2, 3, 4, 5, 6,
$R_{19}$ and $R_{20}$ independently of one another mean hydrogen or a hydrocarbon group having 1-20 C atoms preferably 1-12 C atoms, more preferably 1-6 C atoms, wherein the hydrocarbon group optionally contains one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$ and $SO_3H$, and
$R_{21}$, $R_{22}$ and $R_{23}$ as well as $R_{24}$, $R_{25}$ and $R_{26}$ are defined identical to $R_{16}$, $R_{17}$ and $R_{18}$ and positions not further specified are defined as $R_1$.

Preferable groups A include

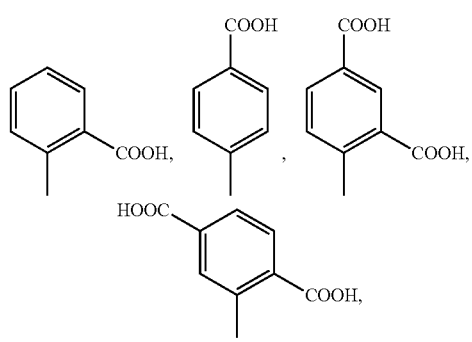

-continued

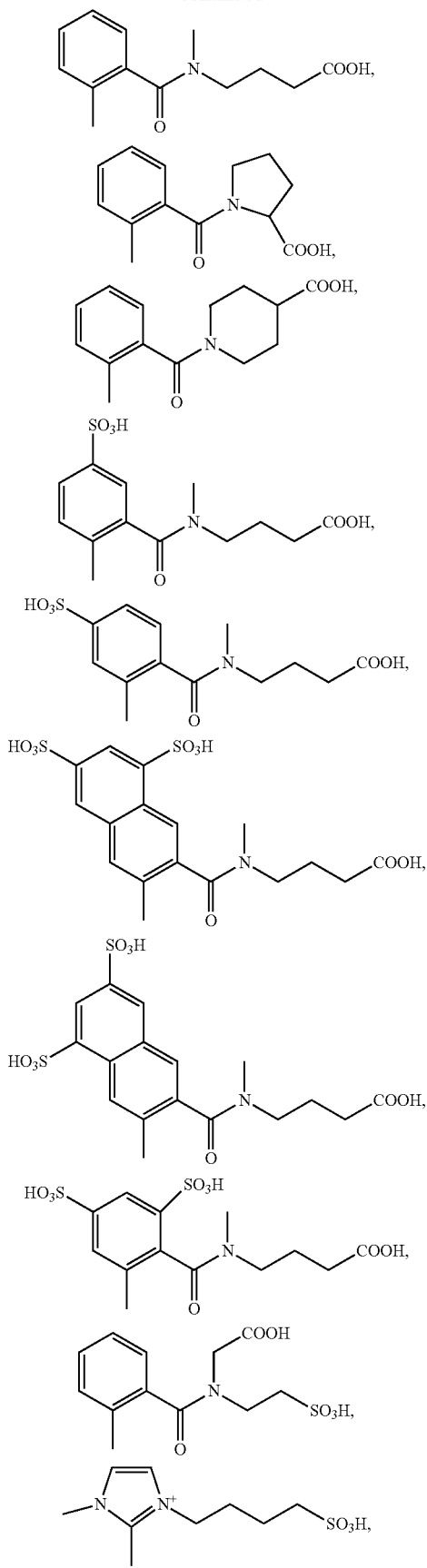

-continued

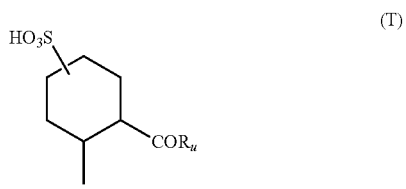

Especially preferable are compounds of the formula (I) in which X=O (rhodamines), X=S (thiorhodamines), X=C(CH$_3$)$_2$ (carborhodamines) or X=Si(CH$_3$)$_2$ (silicorhodamines).

In compounds of the formula (I) with X=O the moiety B preferably does not constitute a sulfoalkyl group and in particular not the moiety —CH$_2$—CH$_2$—CH$_2$—SO$_3$H (sulfopropyl group).

In compounds of the formula (I) with X=O, if the moiety B constitutes a sulfoalkyl group, preferably at least one further SO$_3$H group is contained in the molecule, in particular in the moieties R$_1$, R$_4$, R$_5$, R$_6$, R$_7$, R$_{10}$ or/and A.

The compounds of the formula (II) comprise a group Y. In preferred embodiments of the invention, Y (aliphatic and other substituents, "pyronine-like") in the general formula (II) is hydrogen, CN, CF$_3$, NHR$_{16}$, NR$_{17}$R$_{18}$, (CF$_2$)$_x$COOH with x=1, 2, 3, 4, 5, 6, or the structure (T)

(T)

wherein R$_u$=halogen, OR$_{20}$, NHR$_{21}$, NR$_{22}$R$_{23}$ and positions not further specified are defined as R$_1$.

Y is especially preferably selected from hydrogen, CN, —NH—(CH$_2$)$_3$—COOH, —NH—(CH$_2$)$_5$—COOH, —NH—CH(COOH)—(CH$_2$)$_2$—SO$_3$H, —NH—CH$_2$—CH(SO$_3$H)$_2$ or —NH—CH$_2$—CH$_2$—SO$_3$H.

Especially preferable are compounds of the formula (II) in which X=C(CH$_3$)$_2$ (carbopyronines) or X=Si(CH$_3$)$_2$ (silicopyronines).

Furthermore compounds of the formula (III) are preferable in which X=O (oxazines) or X=C(CH$_3$)$_2$ (carbazines).

Finally, compounds of the formula (IV) are preferable in which X=O (coumarins) or X=NR (carbostyrils).

R$_2$ in compounds of the formula (IV) is preferably a moiety B selected from CH$_2$SO$_3$H, CH$_2$CH$_2$SO$_3$H,

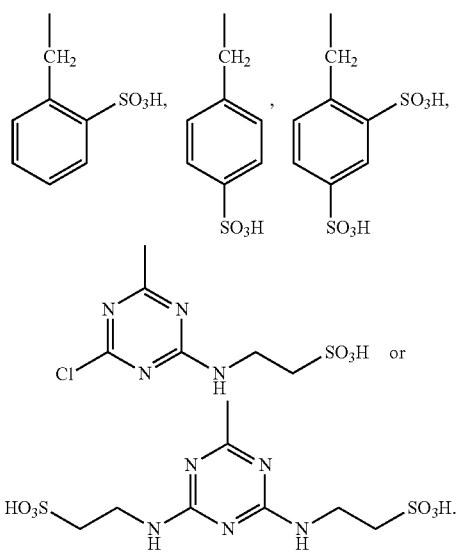

Furthermore, in compounds of the formula (IV) preferably at least one of the moieties $R_1$, $R_4$ and/or $R_7$, in particular $R_1$ and/or $R_4$, is a sulfonic acid group (—$SO_3H$).

In compounds of the formula (IV), in which X=O the moiety B, if it represents an aliphatic hydrocarbon group, is preferably —$CH_2SO_3H$ or —$CH_2CH_2SO_3H$.

According to the invention compounds are provided which have a group containing a sulfonic acid group on at least one of the nitrogen atoms of the compounds of the formulae (I)-(IV). Therein, sulfonic acid groups can be provided via the moieties $R_2$, $R_3$, $R_8$ or $R_9$, wherein in a preferred embodiment the total number of sulfonic acid groups in the moieties $R_2$, $R_3$, $R_8$ and $R_9$ is at least 2, in particular at least 3, preferably at least 4, even more preferably at least 5 and most preferably at least 6. It was found that such compounds allow a high DOL without aggregation phenomena being observed which reduce the fluorescence signal. Furthermore, for these compounds a high water solubility and a low aggregation tendency in aqueous media are observed.

According to the invention it is furthermore possible and preferable, in addition to the sulfonic acid groups provided in the moieties $R_2$, $R_3$, $R_8$ and $R_9$ to add further sulfonic acid groups, preferably in the form of —$SO_3H$ at the positions $R_1$, $R_4$, $R_7$ and/or $R_{10}$ and preferably as —$CH_2$—$SO_3H$ as substituents on ring systems, formed by $R_1$ and $R_2$, $R_3$ and $R_4$, $R_7$ and $R_8$ or/and $R_9$ and $R_{10}$.

The number of the sulfonic acid groups incorporated via the moieties $R_1$, $R_4$, $R_7$ and/or $R_{10}$ is preferably at least 1 and even more preferably at least 2. The number of the sulfonic acid groups incorporated via the groups $R_1$ and $R_2$, $R_3$ and $R_4$, $R_7$ and Ra and/or $R_9$ and $R_{10}$ forming a ring system is preferably 1 and even more preferably at least 2.

It is furthermore possible and preferable to incorporate further sulfonic acid groups via the groups A and Y. In this manner compounds with a large total number of sulfonic acid groups can be provided. Preferably the compounds according to the invention have in the entire molecule at least 2, in particular at least 3, preferably at least 4, even more preferably at least 5, and most preferably at least 6 sulfonic acid groups.

From the protonated, acid forms of the compounds ionic/charged salts can be obtained if they are neutralized with alkaline solutions or bases. These salts may possess an altered solubility in polar, particularly aqueous media. Apart therefrom, such salts are equivalent to the shown formulae.

Furthermore the compounds can also be present in a solvatized, particularly hydrated form, or can contain one or more crystal water molecules. Crystalline or amorphous forms are also equivalent to the shown formulae.

Some compounds possess asymmetric carbon atoms as optical centers or double bonds. The racemates, diasteromers, and geometric isomers resulting therefrom are all covered by the present invention.

The compounds can further have unnatural isotope ratios or even be radioactively labeled. These isotope variants, whether or not they are radioactive, are likewise covered by the shown formulae.

The compounds of the general formulae (I)-(IV) can be used as marker groups in processes of qualitative or/and quantitative determination of an analyte. This determination can preferably be made in aqueous fluids, e.g. samples of bodily fluids such as blood, serum, plasma, lymphatic fluid, bile, cerebrospinal fluid, extracellular tissue fluid, urine, saliva, and sweat, waste water or food. The method can be carried out both as a wet test, e.g. in a cuvette or as a dry test in a corresponding reagent carrier. Here the carrier can be made of any material deemed suitable by a person skilled in the art that can be wetted by the sample to be examined. Examples of such carrier materials include porous glass, plastics, ion exchange resins, dextranes, celluloses, cellulose derivatives or/and hydrophilic polymers, but are not limited to these. The determination of the analyte can hereby be carried out by means of a single reaction or by a sequence of reactions. The analytes are frequently biomolecules, preferably selected from peptides, polypeptides, proteins, nucleotides, nucleosides, nucleic acids, nucleic acid analogs, or/and haptenes.

The compounds of the general formulae (I)-(IV) can be used in all chemical, medical, and biological detection methods known to a person skilled in the art in which fluorescence dyes are suitable as marker groups. For this purpose the compounds are generally covalently coupled to a receptor specific for the analyte to be identified, or to the analyte itself. Toward this end, the compounds according to the invention of the general formulae (I)-(IV) preferably have at least one functional group capable of covalent coupling, such as OH, SH, $NH_2$ and/or COOH, for example.

One generally known process is coupling of the N-hydroxysuccinimidyl ester of the dye to an amino group of the substrate. The specific receptor or analyte can be any suitable compound or any suitable molecule, and is preferably a peptide, a polypeptide, or a nucleic acid. Numerous common coupling methods are described in Greg T. Hermanson, Bioconjugate Techniques, Academic Press, San Diego, Calif., 1996.

Apart from these conventional methods, in recent years the so-called "click-chemistry" has been established. In this case, in accordance with different reaction principles, two molecules are connected to one another via functional groups bio-orthogonally—i.e. the two reaction partners are reacted in a targeted manner also in the presence of many other functionalities and without influencing the biological processes. The best-known example is Cu(I)-catalyzed 1,3-dipolar cycloaddition (Huisgen-cycloaddition) of an alkyne and an azide. In this very current research area, novel and improved reaction methods are constantly studied. For example, Cu-free and thus more biocompatible reactions were developed. An overview of the principles may be found for example in K. Nwe, M. W. Brechbiel, Growing Applications of "Click Chemistry" for Bioconjugation in Contemporary Biomedical Research, Cancer Biotherapy and Radiopharmaceuticals, 2009, 24 (3), 289-302.

Both the absorption- and fluorescence maxima and above all the fluorescence quantum yield are not substantially altered by one of the above described couplings of compounds according to the invention to the above-recited carriers and biomolecules—in contrast to the fluorescence probes frequently used up until now.

These results are exemplarily explained by the coupling of the dyes according to the invention to the model protein streptavidin. The compounds listed in Table 1 belong to the class of rhodamines with the same chromophore system. In an aqueous solution at room temperature they all have a comparably high fluorescence quantum yield of about 90%. But whereas the quantum yield in the dyes corresponding to the prior art is greatly reduced following coupling to streptavidin (cf. Table 1, example ATTO 532), surprisingly the quantum yield in the dyes according to the invention remains extraordinarily high even with a DOL of about 5 or 7 (see Table 1, examples for compounds according to the invention). Thus with established marking procedures, a much better detection reliability is achieved. As is graphically shown in FIGS. 3 and 4, the fluorescence obtained in the conjugate is greatly increased in comparison with the exemplar dyes of the prior art.

TABLE 1

Fluorescence quantum yield of some dyes containing sulfonic acid groups in the streptavidin conjugate at different DOLs in comparison with the uncoupled dye. There is a graphic representation in FIG. 3.

| Compound | DOL | Fluorescence quantum yield of the dye following coupling to streptavidin in comparison with the uncoupled dye |
|---|---|---|
| ATTO 532 | 2.5 | 5% |
|  | 4.6 | 3% |
| 6 | 2.5 | 42% |
|  | 5.5 | 37% |
| 12 | 3.0 | 27% |
| 19 | 5.6 | 10% |
| 25 | 2.8 | 45% |
|  | 6.7 | 35% |

TABLE 1-continued

Fluorescence quantum yield of some dyes containing sulfonic acid groups in the streptavidin conjugate at different DOLs in comparison with the uncoupled dye. There is a graphic representation in FIG. 3.

| Compound | DOL | Fluorescence quantum yield of the dye following coupling to streptavidin in comparison with the uncoupled dye |
|---|---|---|
| 26 | 7.0 | 8% |
| 27 | 1.5 | 34% |

The fluorescence quantum yield of the compounds according to the invention after coupling to streptavidin in comparison with the uncoupled dye at a DOL of 1 is preferably >20%, more preferably >30% and in particular >35%. At a DOL of 3 the fluorescence quantum yield of the compounds according to the invention after coupling to streptavidin in comparison with the uncoupled compounds is preferably >15%, more preferably >20% and in particular >25%. With a DOL of 5 die fluorescence quantum yield of the compounds according to the invention after coupling to streptavidin in comparison with the uncoupled compounds is preferably >10%, more preferably >15% and in particular >20%.

In the physiologically relevant pH-range, the sulfonate group carries a negative charge. Several such groups on an organic dye not only improve water solubility but drastically reduce the aggregation tendency. An increased number of negative charges impedes a mutual attraction. Rather, there is a Coulomb repulsion of equal charges, which also effectively impedes non-specific binding to negatively charged "biopolymers" such as DNA, RNA or certain enzymes. Thereby reduced aggregation and mutual repulsion frequently leads to increased fluorescence, as quenching interactions of the involved chromophores are absent.

Through the present invention, anionic dye molecules may be produced which have a net negative charge in contrast to the positively charged base chromophores.

One special area of use of charged dyes is electrophoretic separation. Through the number of sulfonic acid groups, therefore, dyes with a precisely defined quantity of negative charges can be produced. The conjugates of a series of such dyes can then be distinguished for example in each case by a single elementary charge, depending on how many sulfonic acid groups the corresponding dye scaffolds carry.

Examples of the compounds according to the invention are listed in Tables 2-6, where the structures as well as the absorption and fluorescence maxima are indicated. The spectra of selected compounds are shown FIGS. 5-18.

TABLE 2 general formula (I), examples for X = O (rhodamines)

| Compound | Structure | $\lambda_{abs}$ [nm] | $\lambda_{fl}$ [nm] |
|---|---|---|---|
| 1 | 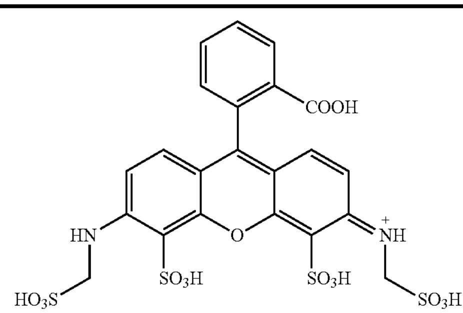 | 533[c] | 554[b] |

TABLE 2-continued

| general formula (I), examples for X = O (rhodamines) | | | |
|---|---|---|---|
| Compound | Structure | $\lambda_{abs}$ [nm] | $\lambda_{fl}$ [nm] |
| 2 | | 554[c] | 584[b] |
| 3 | | 550[c] | 583[b] |
| 4 | | 536[c] | 559[b] |
| 5 | | 560[c] | 584[b] |

TABLE 2-continued
general formula (I), examples for X = O (rhodamines)
| Compound | Structure | $\lambda_{abs}$ [nm] | $\lambda_{fl}$ [nm] |
|---|---|---|---|
| 6 | 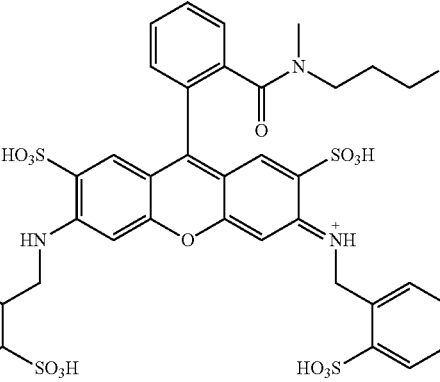 | 534[c] | 559[b] |
| 7 | 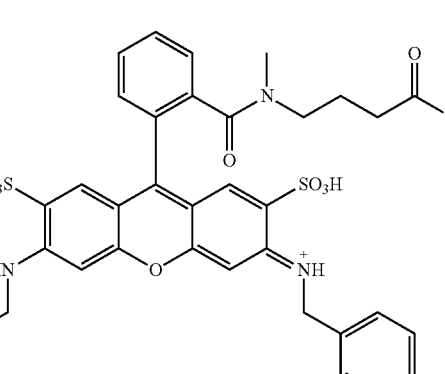 | 534[c] | 559[b] |
| 8 | 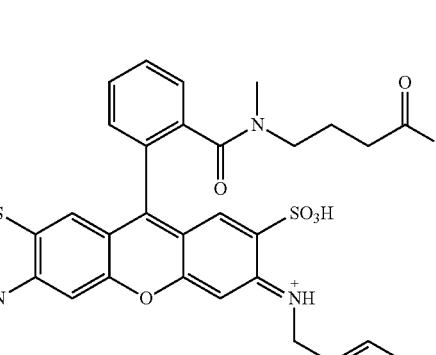 | 533[c] | 556[b] |

TABLE 2-continued
general formula (I), examples for X = O (rhodamines)
| Compound | Structure | $\lambda_{abs}$ [nm] | $\lambda_{fl}$ [nm] |
|---|---|---|---|
| 9 | 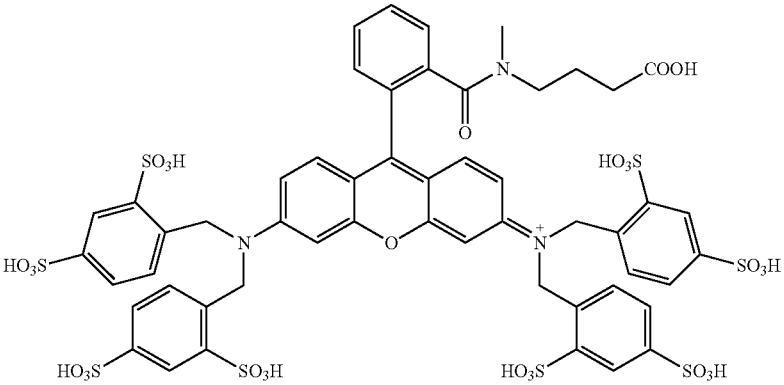 | 550[c] | 572[b] |
| 10 | 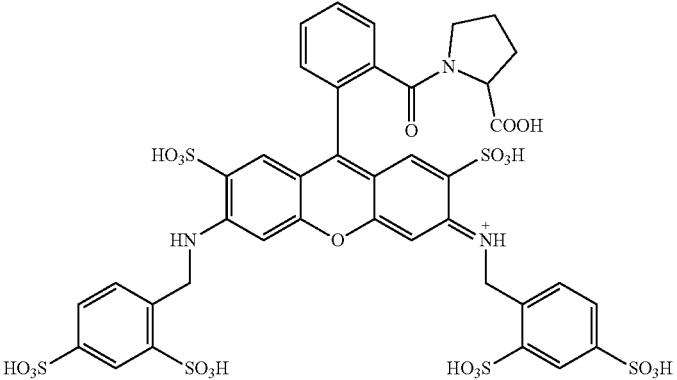 [SMILES: O=C(O)C1CCCN1C(=O)c1ccccc1-c1c2cc(S(=O)(=O)O)/c(=N/Cc3ccc(S(=O)(=O)O)cc3S(=O)(=O)O)cc-2oc2cc(NCc3ccc(S(=O)(=O)O)cc3S(=O)(=O)O)c(S(=O)(=O)O)cc12] | 534[c] | 556[b] |
| 11 | 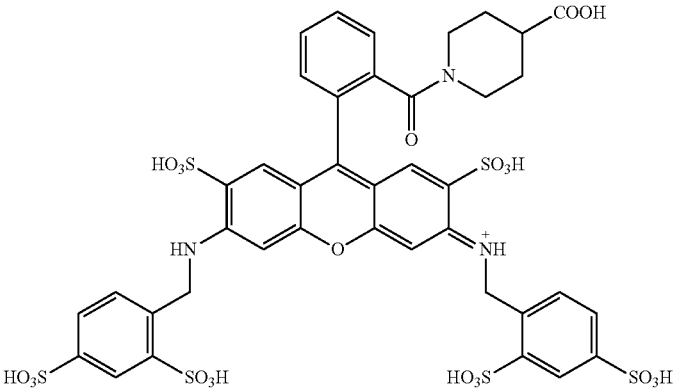 [SMILES: O=C(O)C1CCN(C(=O)c2ccccc2-c2c3cc(S(=O)(=O)O)/c(=N/Cc4ccc(S(=O)(=O)O)cc4S(=O)(=O)O)cc-3oc3cc(NCc4ccc(S(=O)(=O)O)cc4S(=O)(=O)O)c(S(=O)(=O)O)cc23)CC1] | 529[c] | 550[b] |

TABLE 2-continued general formula (I), examples for X = O (rhodamines)

| Compound | Structure | $\lambda_{abs}$ [nm] | $\lambda_{fl}$ [nm] |
|---|---|---|---|
| 12 | 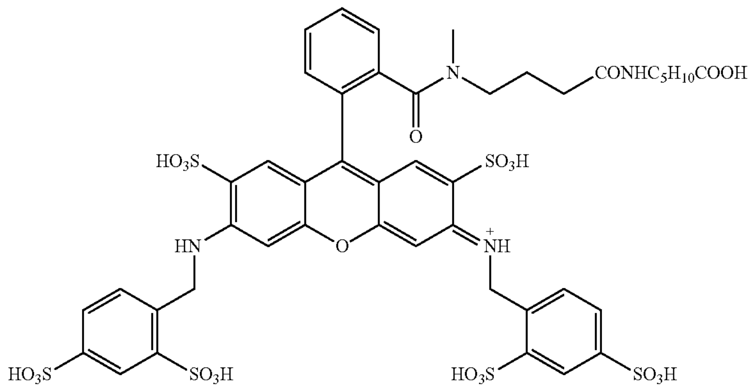 | $536^c$ | $555^b$ |
| 13 | 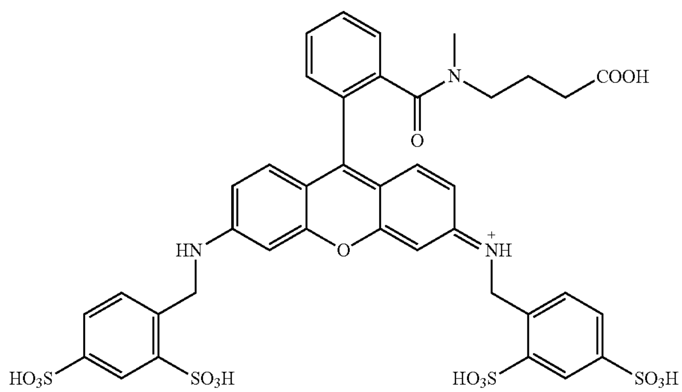 [SMILES: CN(CCCC(=O)O)C(=O)c1ccccc1-c1c2cc/c(=N/Cc3ccc(S(=O)(=O)O)cc3S(=O)(=O)O)cc-2oc2cc(NCc3ccc(S(=O)(=O)O)cc3S(=O)(=O)O)ccc12] | $534^c$ | $555^b$ |
| 14 | 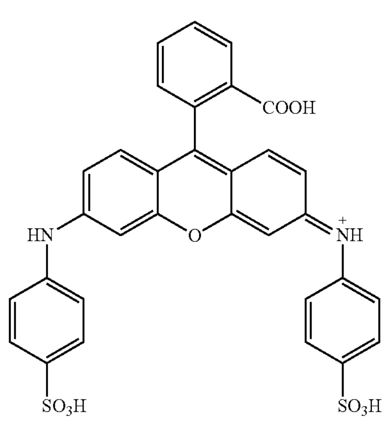 [SMILES: O=C(O)c1ccccc1-c1c2cc/c(=N/c3ccc(S(=O)(=O)O)cc3)cc-2oc2cc(Nc3ccc(S(=O)(=O)O)cc3)ccc12] | $560^b$ | — |

TABLE 2-continued general formula (I), examples for X = O (rhodamines)

| Compound | Structure | $\lambda_{abs}$ [nm] | $\lambda_{fl}$ [nm] |
|---|---|---|---|
| 15 | 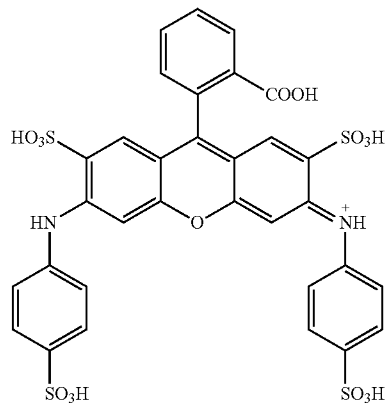 [SMILES: O=C(O)c1ccccc1-c1c2cc(S(=O)(=O)O)/c(=N/c3ccc(S(=O)(=O)O)cc3)cc-2oc2cc(Nc3ccc(S(=O)(=O)O)cc3)c(S(=O)(=O)O)cc12] | 558[c] | — |
| 16 | 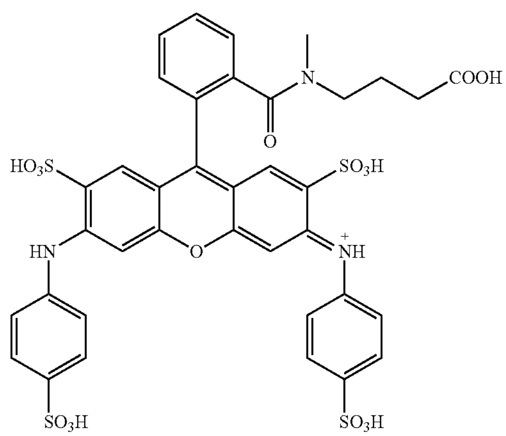 [SMILES: CN(CCCC(=O)O)C(=O)c1ccccc1-c1c2cc(S(=O)(=O)O)/c(=N/c3ccc(S(=O)(=O)O)cc3)cc-2oc2cc(Nc3ccc(S(=O)(=O)O)cc3)c(S(=O)(=O)O)cc12] | 566[c] | — |
| 17 | 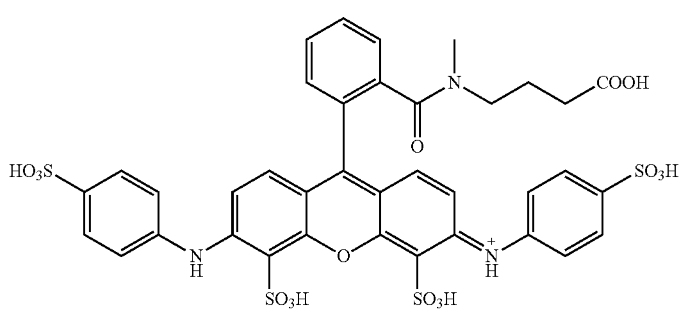 [SMILES: CN(CCCC(=O)O)C(=O)c1ccccc1-c1c2cc/c(=N\c3ccc(S(=O)(=O)O)cc3)c(S(=O)(=O)O)c-2oc2c(S(=O)(=O)O)c(Nc3ccc(S(=O)(=O)O)cc3)ccc12] | 555[c] | — |

TABLE 2-continued
| | general formula (I), examples for X = O (rhodamines) | | |
|---|---|---|---|
| Compound | Structure | $\lambda_{abs}$ [nm] | $\lambda_{fl}$ [nm] |
| 18 | 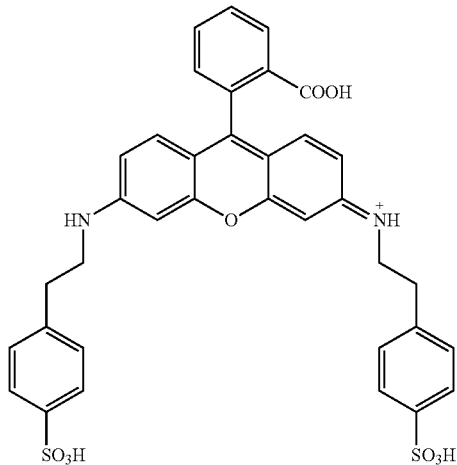 [SMILES: O=C(O)c1ccccc1-c1c2cc/c(=N/CCc3ccc(S(=O)(=O)O)cc3)cc-2oc2cc(NCCc3ccc(S(=O)(=O)O)cc3)ccc12] | 530[c] | 551[b] |
| 19 | 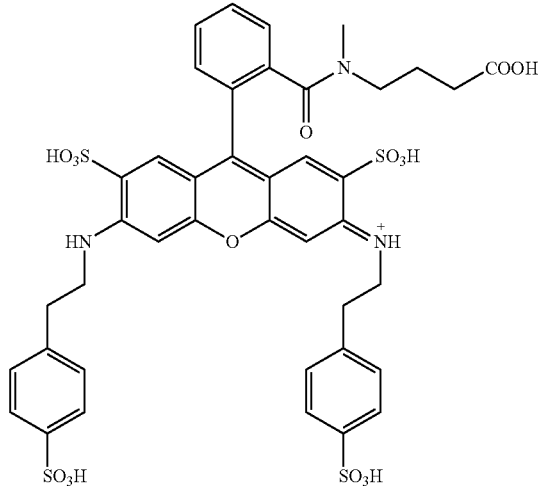 [SMILES: CN(CCCC(=O)O)C(=O)c1ccccc1-c1c2cc(S(=O)(=O)O)/c(=N/CCc3ccc(S(=O)(=O)O)cc3)cc-2oc2cc(NCCc3ccc(S(=O)(=O)O)cc3)c(S(=O)(=O)O)cc12] | 537[c] | 560[b] |
| 20 | 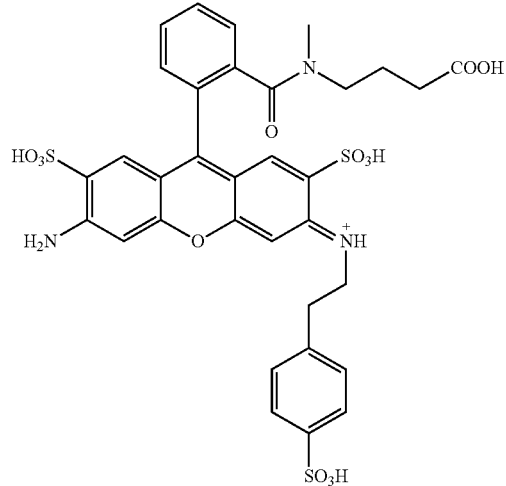 [SMILES: CN(CCCC(=O)O)C(=O)c1ccccc1-c1c2cc(S(=O)(=O)O)/c(=N/CCc3ccc(S(=O)(=O)O)cc3)cc-2oc2cc(N)c(S(=O)(=O)O)cc12] | 528[c] | 550[b] |

TABLE 2-continued general formula (I), examples for X = O (rhodamines)

| Compound | Structure | $\lambda_{abs}$ [nm] | $\lambda_{fl}$ [nm] |
|---|---|---|---|
| 21 | 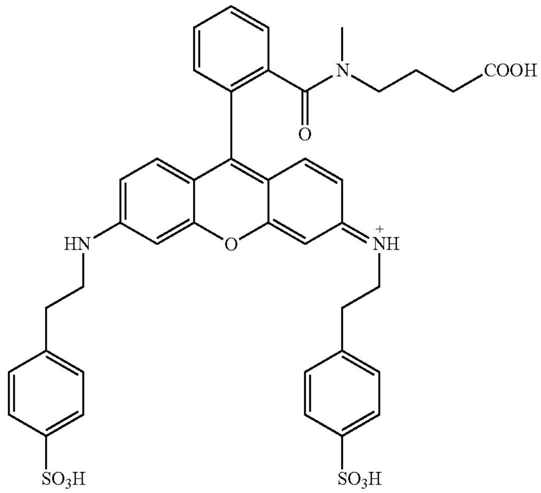 [SMILES: CN(CCCC(=O)O)C(=O)c1ccccc1-c1c2cc/c(=N/CCc3ccc(S(=O)(=O)O)cc3)cc-2oc2cc(NCCc3ccc(S(=O)(=O)O)cc3)ccc12] | 538[c] | 559[b] |
| 22 | 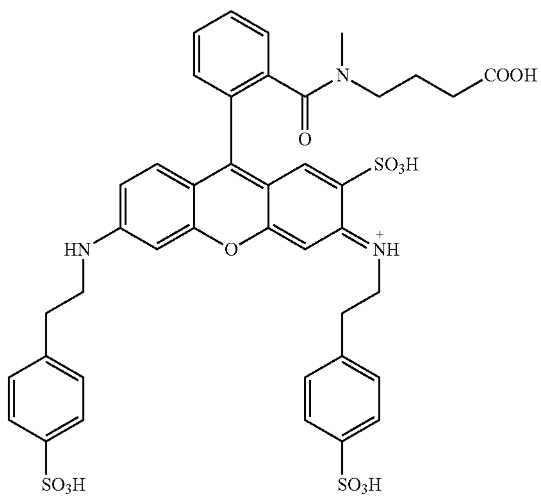 [SMILES: CN(CCCC(=O)O)C(=O)c1ccccc1-c1c2cc(S(=O)(=O)O)/c(=N/CCc3ccc(S(=O)(=O)O)cc3)cc-2oc2cc(NCCc3ccc(S(=O)(=O)O)cc3)ccc12] | 536[c] | 558[b] |
| 23 | 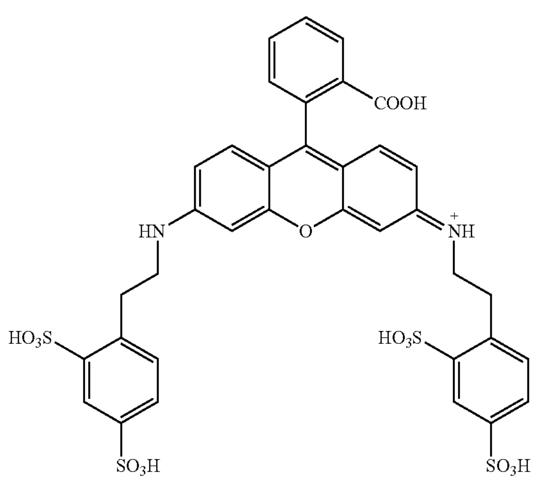 [SMILES: O=C(O)c1ccccc1-c1c2cc/c(=N/CCc3ccc(S(=O)(=O)O)cc3S(=O)(=O)O)cc-2oc2cc(NCCc3ccc(S(=O)(=O)O)cc3S(=O)(=O)O)ccc12] | 532[c] | 559[b] |

TABLE 2-continued
general formula (I), examples for X = O (rhodamines)
| Compound | Structure | $\lambda_{abs}$ [nm] | $\lambda_{fl}$ [nm] |
|---|---|---|---|
| 24 | 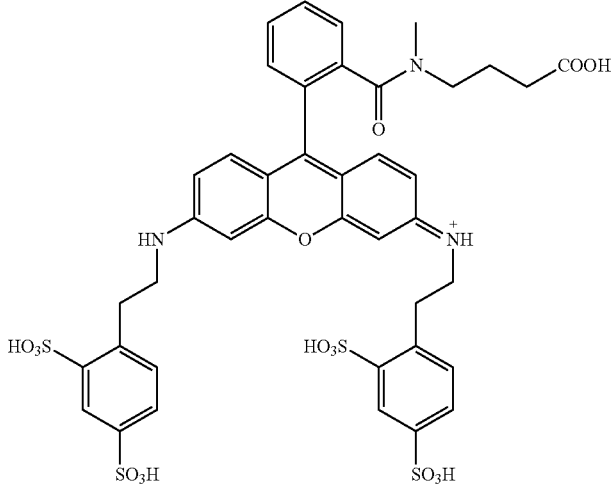 [SMILES: CN(CCCC(=O)O)C(=O)c1ccccc1-c1c2cc/c(=N/CCc3ccc(S(=O)(=O)O)cc3S(=O)(=O)O)cc-2oc2cc(NCCc3ccc(S(=O)(=O)O)cc3S(=O)(=O)O)ccc12] | 539[c] | 561[b] |
| 25 | 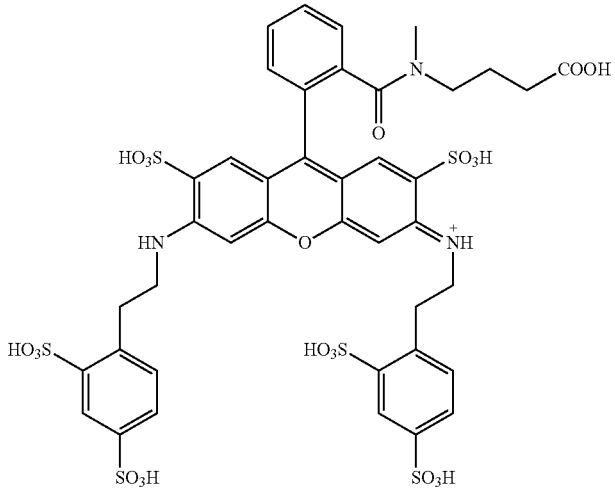 [SMILES: CN(CCCC(=O)O)C(=O)c1ccccc1-c1c2cc(S(=O)(=O)O)/c(=N/CCc3ccc(S(=O)(=O)O)cc3S(=O)(=O)O)cc-2oc2cc(NCCc3ccc(S(=O)(=O)O)cc3S(=O)(=O)O)c(S(=O)(=O)O)cc12] | 539[b] | 560[b] |
| 26 | 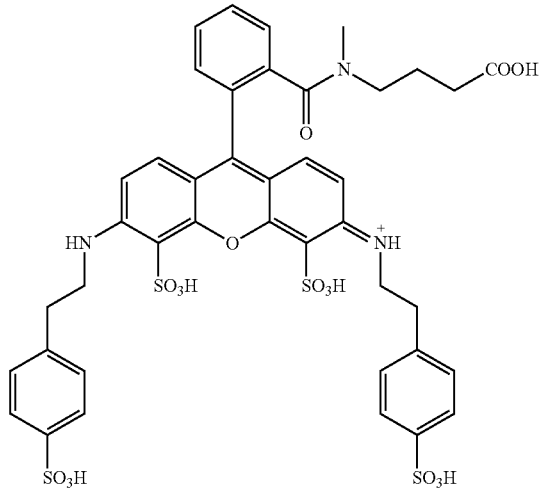 [SMILES: CN(CCCC(=O)O)C(=O)c1ccccc1-c1c2cc/c(=N/CCc3ccc(S(=O)(=O)O)cc3)c(S(=O)(=O)O)c-2oc2c(S(=O)(=O)O)c(NCCc3ccc(S(=O)(=O)O)cc3)ccc12] | 538[c] | 558[b] |

TABLE 2-continued general formula (I), examples for X = O (rhodamines)

| Compound | Structure | $\lambda_{abs}$ [nm] | $\lambda_{fl}$ [nm] |
|---|---|---|---|
| 27 | 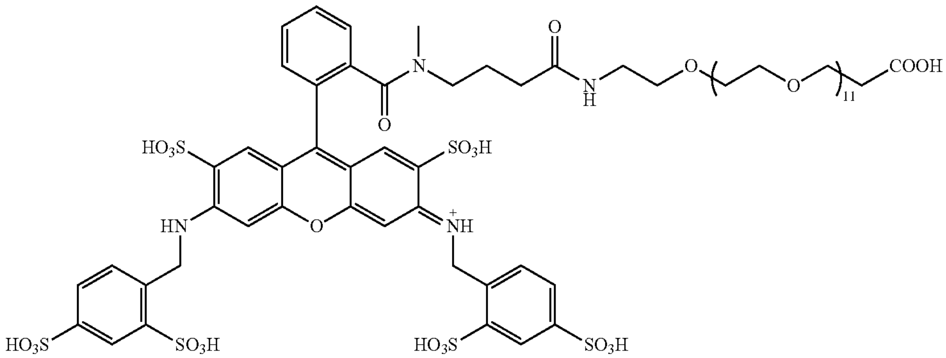 | 539[c] | 558[b] |
| 28 | 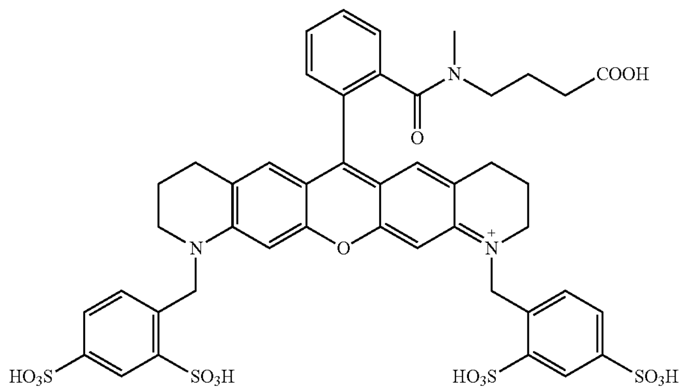 | 567[c] | |
| 29 | 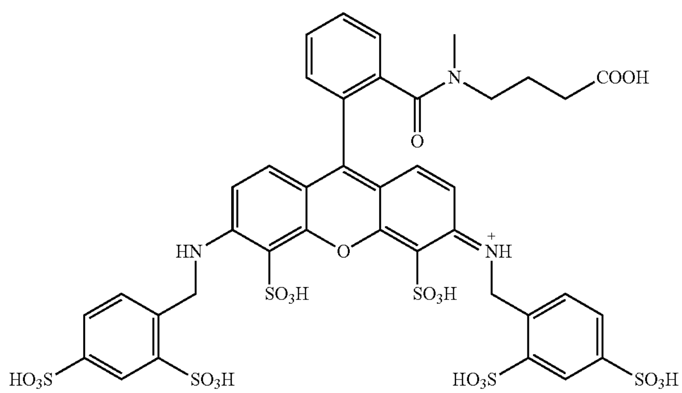 [SMILES: CN(CCCC(=O)O)C(=O)c1ccccc1-c1c2cc/c(=N/Cc3ccc(S(=O)(=O)O)cc3S(=O)(=O)O)c(S(=O)(=O)O)c-2oc2c(S(=O)(=O)O)c(NCc3ccc(S(=O)(=O)O)cc3S(=O)(=O)O)ccc12] | 531[c] | |
| 30 | 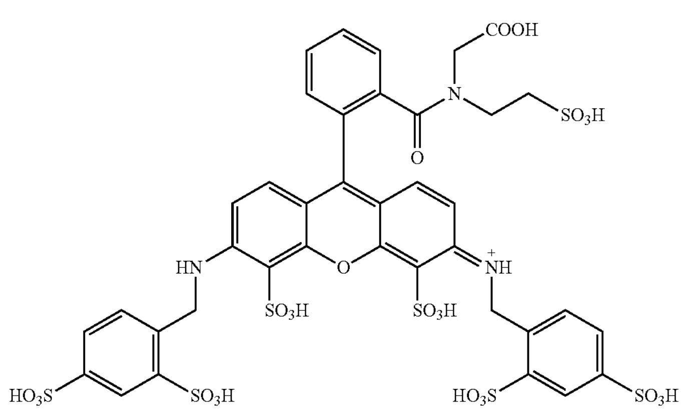 [SMILES: O=C(O)CN(CCS(=O)(=O)O)C(=O)c1ccccc1-c1c2cc/c(=N/Cc3ccc(S(=O)(=O)O)cc3S(=O)(=O)O)c(S(=O)(=O)O)c-2oc2c(S(=O)(=O)O)c(NCc3ccc(S(=O)(=O)O)cc3S(=O)(=O)O)ccc12] | 536[c] | |

TABLE 2-continued
general formula (I), examples for X = O (rhodamines)
| Compound | Structure | $\lambda_{abs}$ [nm] | $\lambda_{fl}$ [nm] |
|---|---|---|---|
| 31 | 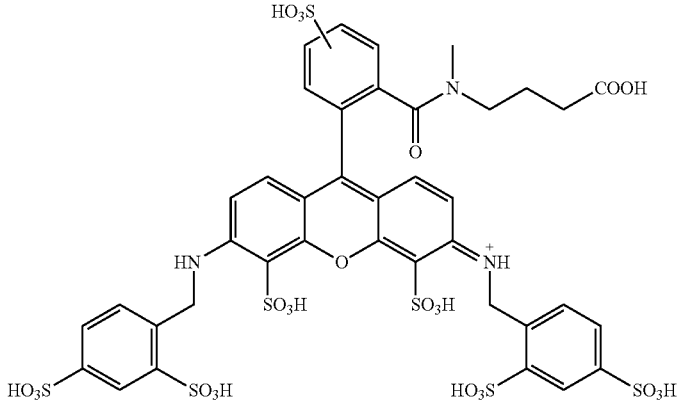 (2 isomers) | 532[c] | |
| 32 | 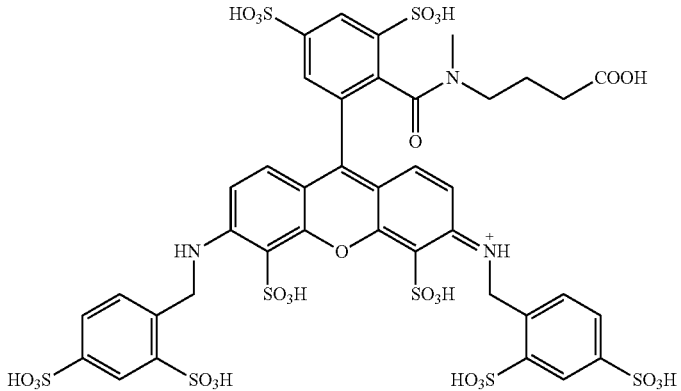 [SMILES: CN(CCCC(=O)O)C(=O)c1c(-c2c3cc/c(=N/Cc4ccc(S(=O)(=O)O)cc4S(=O)(=O)O)c(S(=O)(=O)O)c-3oc3c(S(=O)(=O)O)c(NCc4ccc(S(=O)(=O)O)cc4S(=O)(=O)O)ccc23)cc(S(=O)(=O)O)cc1S(=O)(=O)O] | 530[c] | |
| 33 | 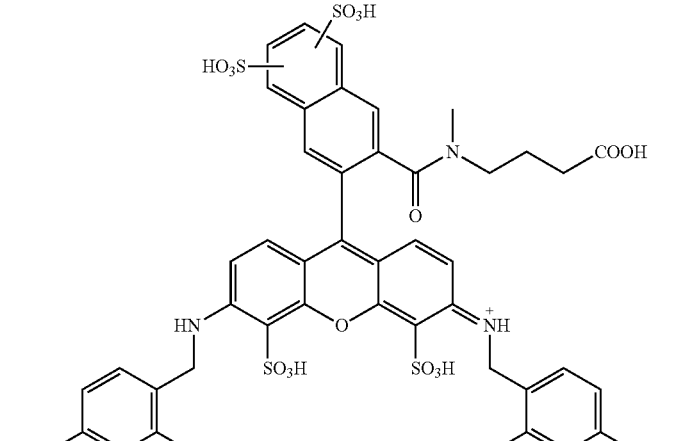 (2 isomers) | 539[c] | |

TABLE 2-continued
general formula (I), examples for X = O (rhodamines)
| Compound | Structure | $\lambda_{abs}$ [nm] | $\lambda_{fl}$ [nm] |
|---|---|---|---|
| 34 | 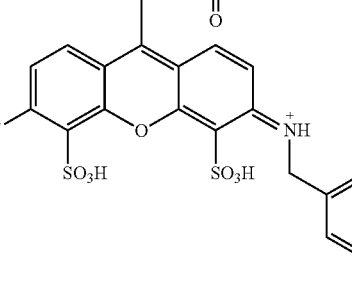 | 530[b] | |
| 35 | 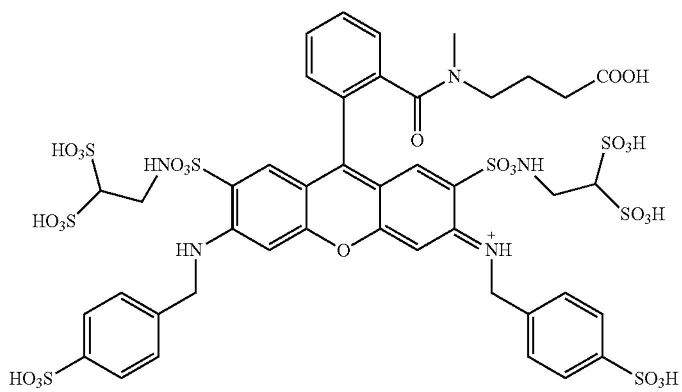 | 540[b] | 562[b] |
Solvent: [a]ethanol, [b]PBS pH 7.4, [c]water/acetonitrile 1:1
TABLE 3
general formula (I), examples for X = C(CH$_3$)$_2$ (carborhodamines), X = Si(CH$_3$)$_2$ (silicorhodamines)
| Compound | Structure | $\lambda_{abs}$ [nm] | $\lambda_{fl}$ [nm] |
|---|---|---|---|
| 36 | 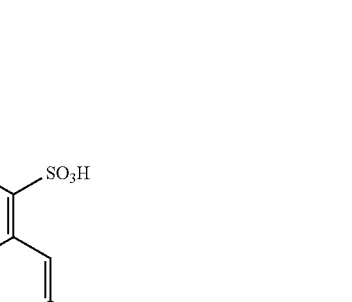 | 656[b] | 677[b] |

TABLE 3-continued
general formula (I), examples for X = C(CH$_3$)$_2$ (carborhodamines), X = Si(CH$_3$)$_2$ (silicorhodamines)
| Compound | Structure | $\lambda_{abs}$ [nm] | $\lambda_{fl}$ [nm] |
|---|---|---|---|
| 37 | 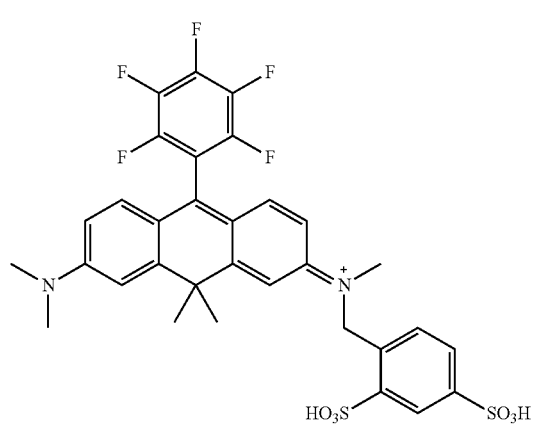 [SMILES: CN(C)c1ccc2c(c1)C(C)(C)C1=C/C(=[N+](/C)Cc3ccc(S(=O)(=O)O)cc3S(=O)(=O)O)C=CC1=C2c1c(F)c(F)c(F)c(F)c1F] | 642[b] | 661[b] |
| 38 | 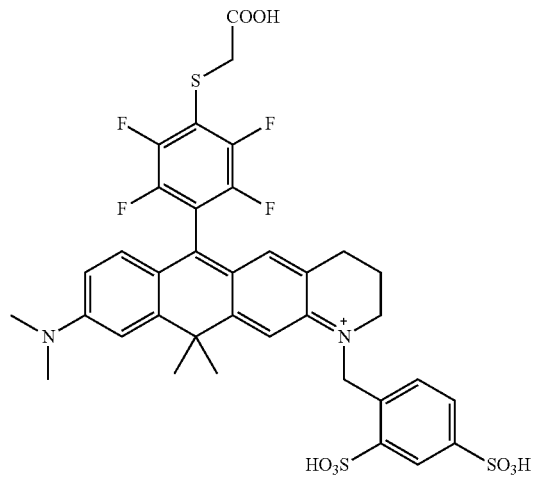 [SMILES: CN(C)c1ccc2c(c1)C(C)(C)c1cc3c(cc1=C2c1c(F)c(F)c(SCC(=O)O)c(F)c1F)CCC[N+]=3Cc1ccc(S(=O)(=O)O)cc1S(=O)(=O)O] | 646[b] | 667[b] |
| 39 | 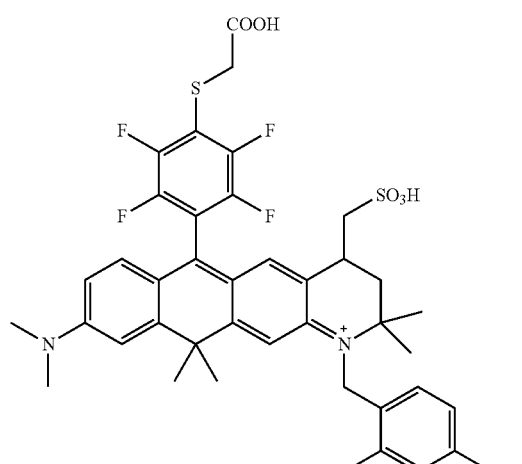 | 673[b] | 693[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 40 | 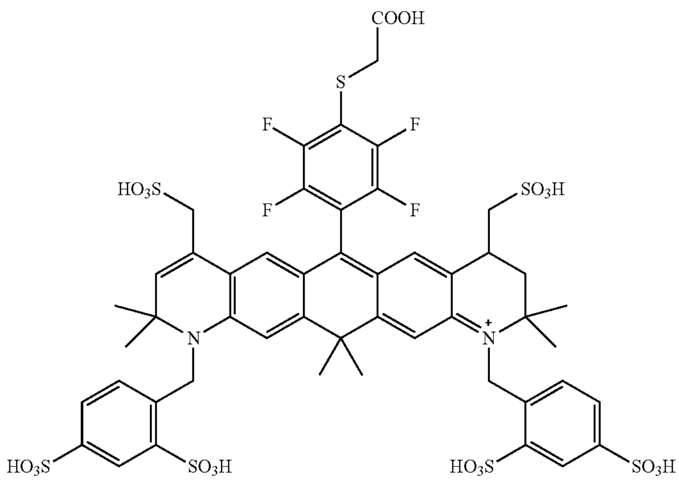 [SMILES: CC1(C)c2cc3c(cc2C(c2c(F)c(F)c(SCC(=O)O)c(F)c2F)=c2cc4c(cc21)=[N+](Cc1ccc(S(=O)(=O)O)cc1S(=O)(=O)O)C(C)(C)CC4CS(=O)(=O)O)C(CS(=O)(=O)O)=CC(C)(C)N3Cc1ccc(S(=O)(=O)O)cc1S(=O)(=O)O] | 699[b] | 720[b] |
| 41 | 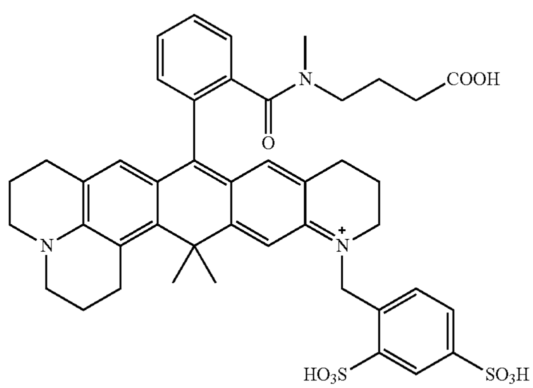 [SMILES: CN(CCCC(=O)O)C(=O)c1ccccc1C1=c2cc3c(cc2C(C)(C)c2c1cc1c4c2CCCN4CCC1)=[N+](Cc1ccc(S(=O)(=O)O)cc1S(=O)(=O)O)CCC3] | 642[a]<br>640[b] | 663[a]<br>659[b] |
| 42 | 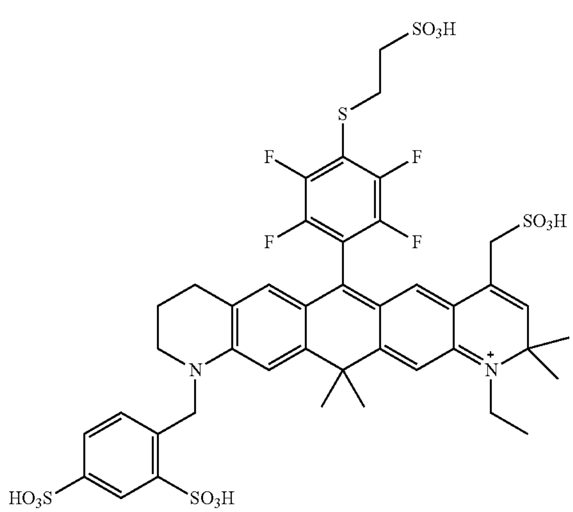 [SMILES: CC[N+]1=c2cc3c(cc2C(CS(=O)(=O)O)=CC1(C)C)=C(c1c(F)c(F)c(SCCS(=O)(=O)O)c(F)c1F)c1cc2c(cc1C3(C)C)N(Cc1ccc(S(=O)(=O)O)cc1S(=O)(=O)O)CCC2] | 682[b] | 701[b] |

TABLE 3-continued
general formula (I), examples for X = C(CH$_3$)$_2$ (carborhodamines), X = Si(CH$_3$)$_2$ (silicorhodamines)
| Compound | Structure | $\lambda_{abs}$ [nm] | $\lambda_{fl}$ [nm] |
|---|---|---|---|
| 43 | 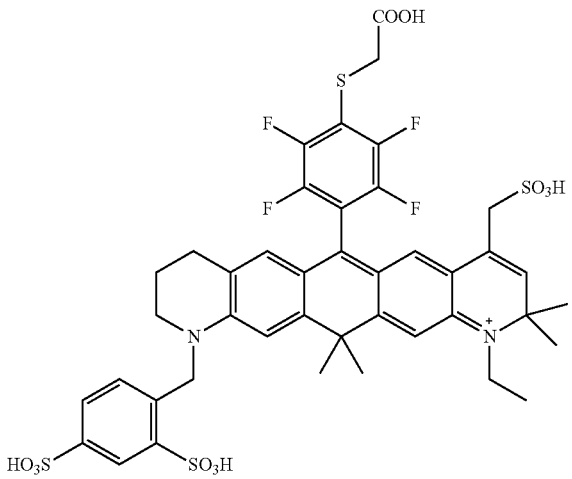 [SMILES: CC[N+]1=c2cc3c(cc2C(CS(=O)(=O)O)=CC1(C)C)=C(c1c(F)c(F)c(SCC(=O)O)c(F)c1F)c1cc2c(cc1C3(C)C)N(Cc1ccc(S(=O)(=O)O)cc1S(=O)(=O)O)CCC2] | 684[b] | 704[b] |
| 44 | 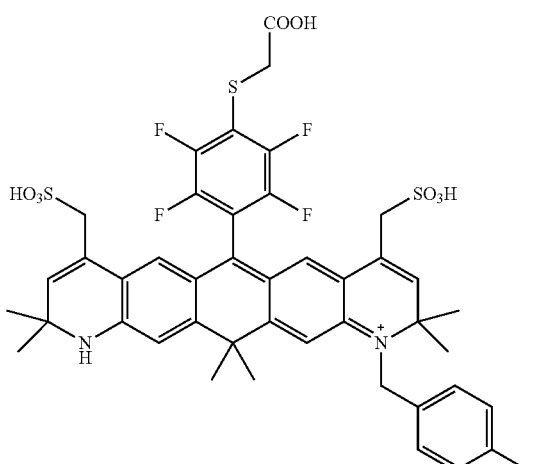 | 687[b] | 707[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 45 | 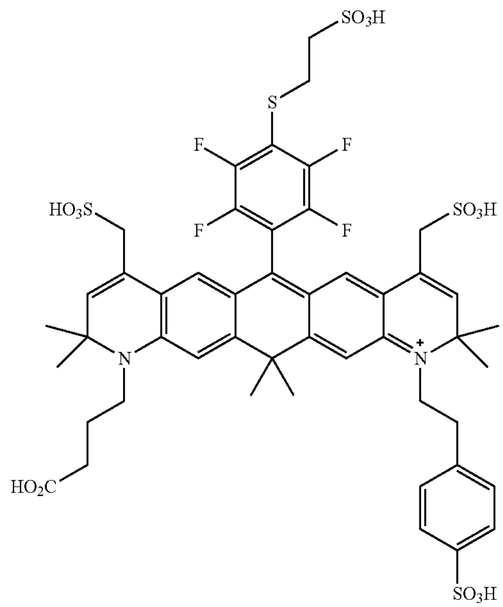 | 698[b] | 719[b] |
| 46 | 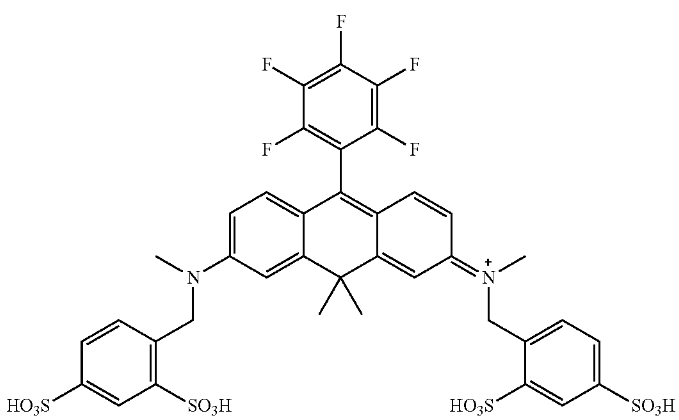 [SMILES: CN(Cc1ccc(S(=O)(=O)O)cc1S(=O)(=O)O)c1ccc2c(c1)C(C)(C)C1=C/C(=[N+](/C)Cc3ccc(S(=O)(=O)O)cc3S(=O)(=O)O)C=CC1=C2c1c(F)c(F)c(F)c(F)c1F] | 646[b] | 666[b] |
| 47 | 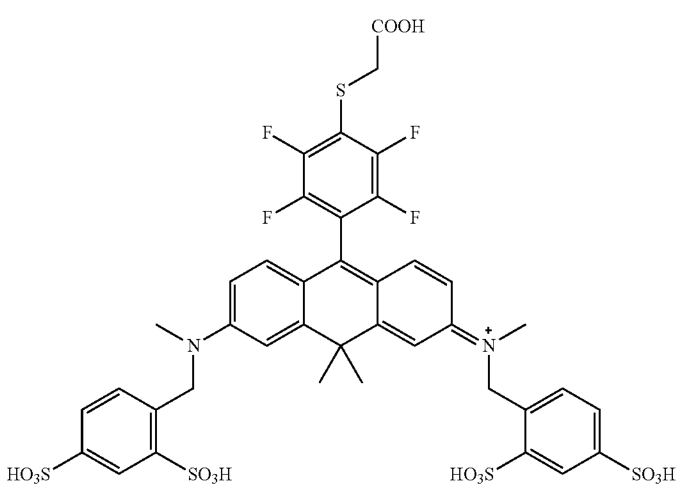 [SMILES: CN(Cc1ccc(S(=O)(=O)O)cc1S(=O)(=O)O)c1ccc2c(c1)C(C)(C)C1=C/C(=[N+](/C)Cc3ccc(S(=O)(=O)O)cc3S(=O)(=O)O)C=CC1=C2c1c(F)c(F)c(SCC(=O)O)c(F)c1F] | 645[b] | 666[b] |

TABLE 3-continued general formula (I), examples for X = C(CH₃)₂ (carborhodamines), X = Si(CH₃)₂ (silicorhodamines)

| Compound | Structure | $\lambda_{abs}$ [nm] | $\lambda_{fl}$ [nm] |
|---|---|---|---|
| 48 | 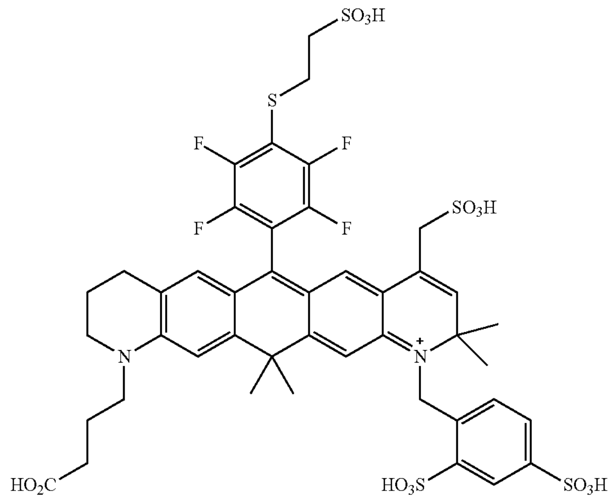 [SMILES: CC1(C)c2cc3c(cc2C(c2c(F)c(F)c(SCCS(=O)(=O)O)c(F)c2F)=c2cc4c(cc21)=[N+](Cc1ccc(S(=O)(=O)O)cc1S(=O)(=O)O)C(C)(C)C=C4CS(=O)(=O)O)CCCN3CCCC(=O)O] | 682[b] | 705[b] |
| 49 | 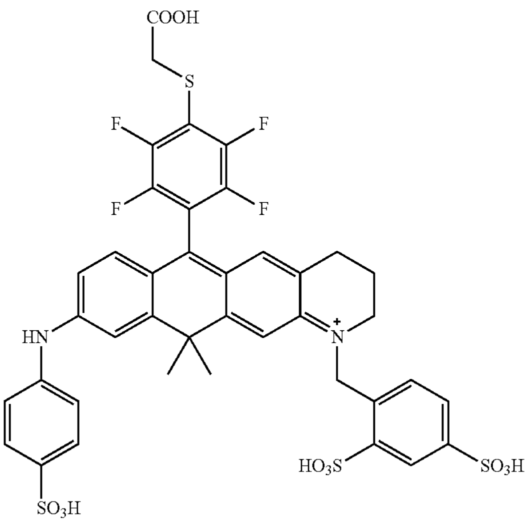 [SMILES: CC1(C)c2cc(Nc3ccc(S(=O)(=O)O)cc3)ccc2C(c2c(F)c(F)c(SCC(=O)O)c(F)c2F)=c2cc3c(cc21)=[N+](Cc1ccc(S(=O)(=O)O)cc1S(=O)(=O)O)CCC3] | 648[b] | — |
| 50 | 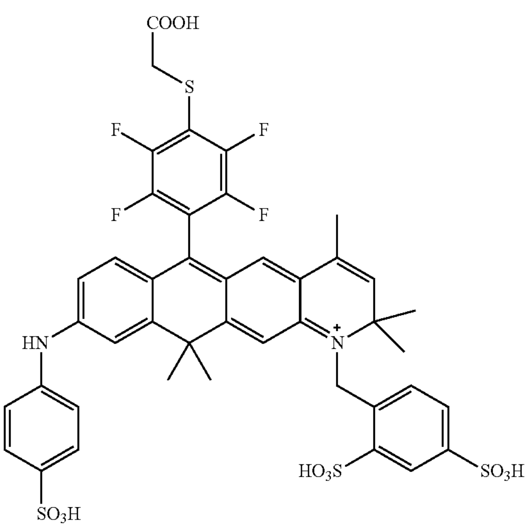 [SMILES: CC1=CC(C)(C)[N+](Cc2ccc(S(=O)(=O)O)cc2S(=O)(=O)O)=c2cc3c(cc21)=C(c1c(F)c(F)c(SCC(=O)O)c(F)c1F)c1ccc(Nc2ccc(S(=O)(=O)O)cc2)cc1C3(C)C] | 669[b] | — |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 51 | 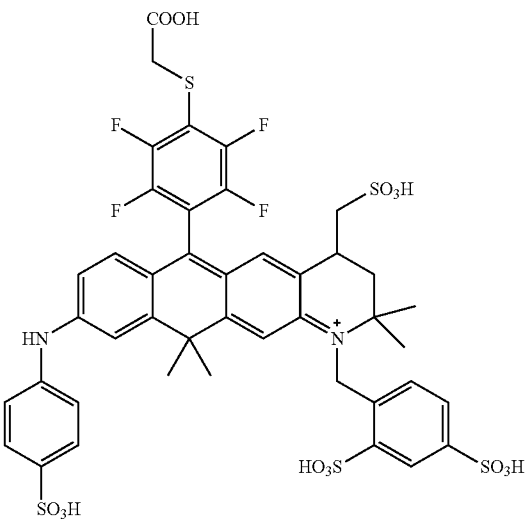 [SMILES: CC1(C)c2cc(Nc3ccc(S(=O)(=O)O)cc3)ccc2C(c2c(F)c(F)c(SCC(=O)O)c(F)c2F)=c2cc3c(cc21)=[N+](Cc1ccc(S(=O)(=O)O)cc1S(=O)(=O)O)C(C)(C)CC3CS(=O)(=O)O] | 650[b] | — |
| 52 | 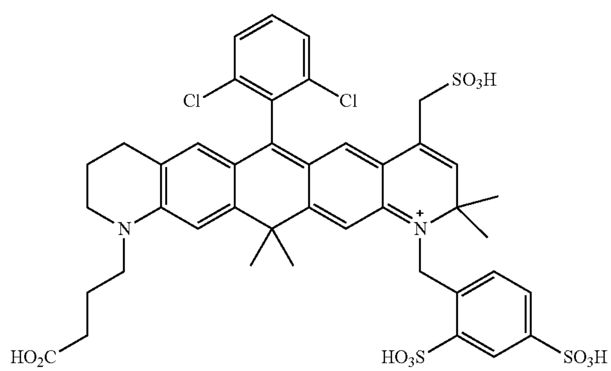 [SMILES: CC1(C)c2cc3c(cc2C(c2c(Cl)cccc2Cl)=c2cc4c(cc21)=[N+](Cc1ccc(S(=O)(=O)O)cc1S(=O)(=O)O)C(C)(C)C=C4CS(=O)(=O)O)CCCN3CCCC(=O)O] | 673[b] | 698[b] |
| 53 | 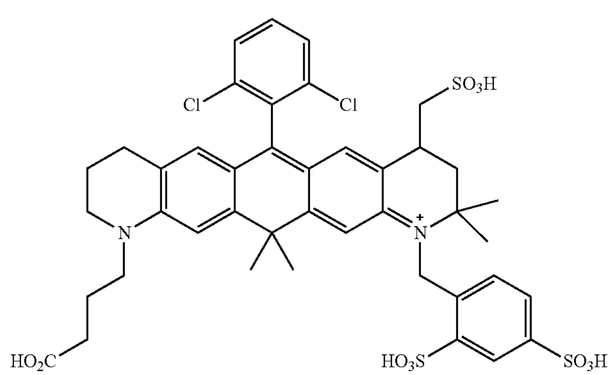 [SMILES: CC1(C)c2cc3c(cc2C(c2c(Cl)cccc2Cl)=c2cc4c(cc21)=[N+](Cc1ccc(S(=O)(=O)O)cc1S(=O)(=O)O)C(C)(C)CC4CS(=O)(=O)O)CCCN3CCCC(=O)O] | 654[b] | 677[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 54 | 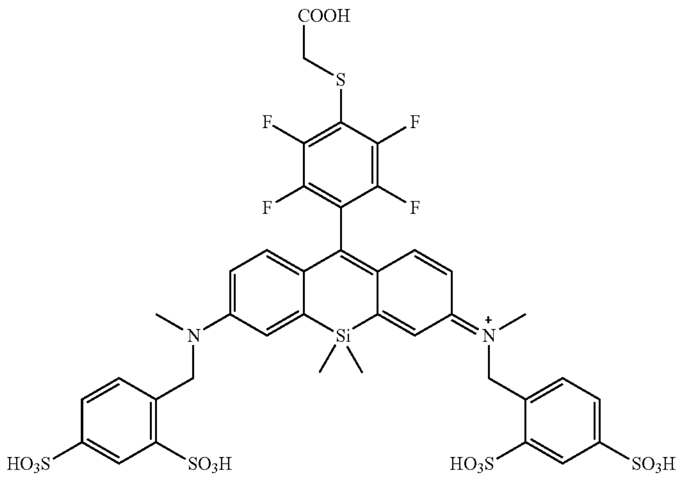 [SMILES: CN(Cc1ccc(S(=O)(=O)O)cc1S(=O)(=O)O)c1ccc2c(c1)[Si](C)(C)C1=C/C(=[N+](/C)Cc3ccc(S(=O)(=O)O)cc3S(=O)(=O)O)C=CC1=C2c1c(F)c(F)c(SCC(=O)O)c(F)c1F] | 685[b] | 709[b] |
| 55 | 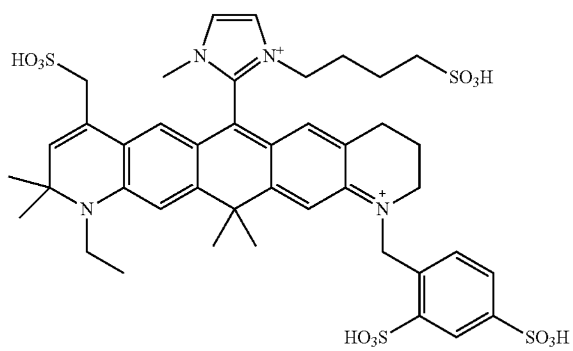 [SMILES: CCN1c2cc3c(cc2C(CS(=O)(=O)O)=CC1(C)C)C(c1n(C)cc[n+]1CCCCS(=O)(=O)O)=c1cc2c(cc1C3(C)C)=[N+](Cc1ccc(S(=O)(=O)O)cc1S(=O)(=O)O)CCC2] | 725[b] | 749[b] |
| 56 | 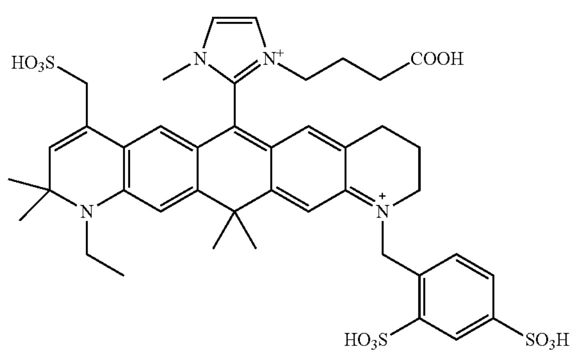 [SMILES: CCN1c2cc3c(cc2C(CS(=O)(=O)O)=CC1(C)C)C(c1n(C)cc[n+]1CCCC(=O)O)=c1cc2c(cc1C3(C)C)=[N+](Cc1ccc(S(=O)(=O)O)cc1S(=O)(=O)O)CCC2] | 724[b] | 746[b] |
| 57 | 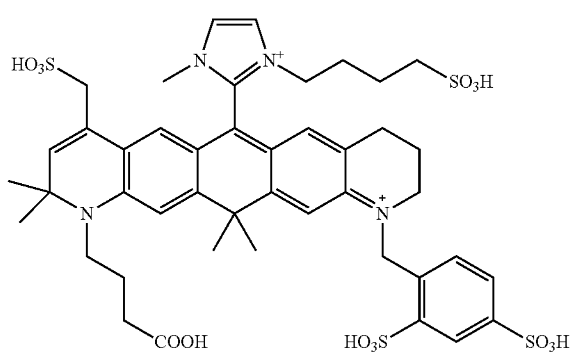 [SMILES: Cn1cc[n+](CCCCS(=O)(=O)O)c1C1=c2cc3c(cc2C(C)(C)c2cc4c(cc21)C(CS(=O)(=O)O)=CC(C)(C)N4CCCC(=O)O)=[N+](Cc1ccc(S(=O)(=O)O)cc1S(=O)(=O)O)CCC3] | 725[b] | 749[b] |

TABLE 3-continued
general formula (I), examples for X = C(CH$_3$)$_2$ (carborhodamines), X = Si(CH$_3$)$_2$ (silicorhodamines)
| Compound | Structure | $\lambda_{abs}$ [nm] | $\lambda_{fl}$ [nm] |
|---|---|---|---|
| 58 | 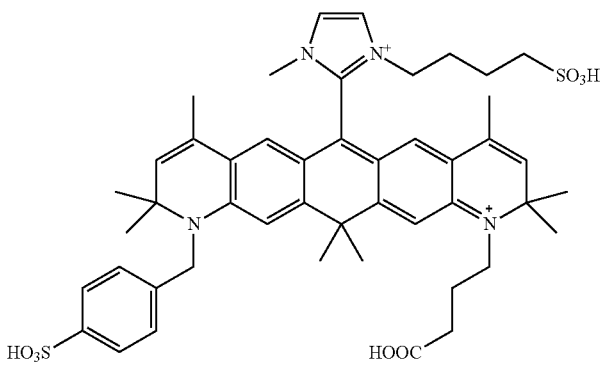 [SMILES: CC1=CC(C)(C)N(Cc2ccc(S(=O)(=O)O)cc2)c2cc3c(cc21)C(c1n(C)cc[n+]1CCCCS(=O)(=O)O)=c1cc2c(cc1C3(C)C)=[N+](CCCC(=O)O)C(C)(C)C=C2C] | 742[b] | 775[b] |
| 59 | 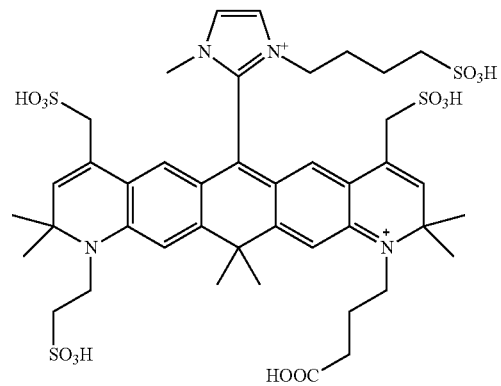 | 739[b] | 771[b] |
| 60 | 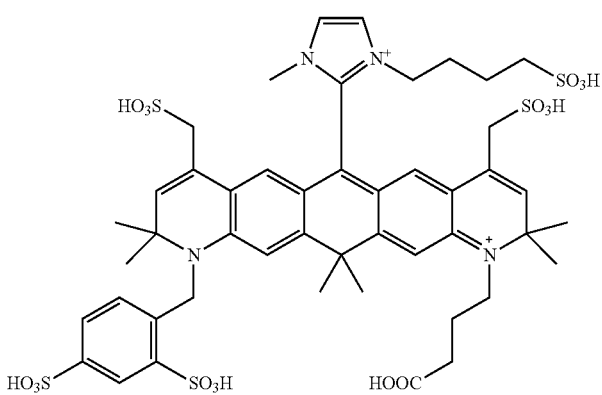 [SMILES: Cn1cc[n+](CCCCS(=O)(=O)O)c1C1=c2cc3c(cc2C(C)(C)c2cc4c(cc21)C(CS(=O)(=O)O)=CC(C)(C)N4Cc1ccc(S(=O)(=O)O)cc1S(=O)(=O)O)=[N+](CCCC(=O)O)C(C)(C)C=C3CS(=O)(=O)O] | 742[b] | 775[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 61 | 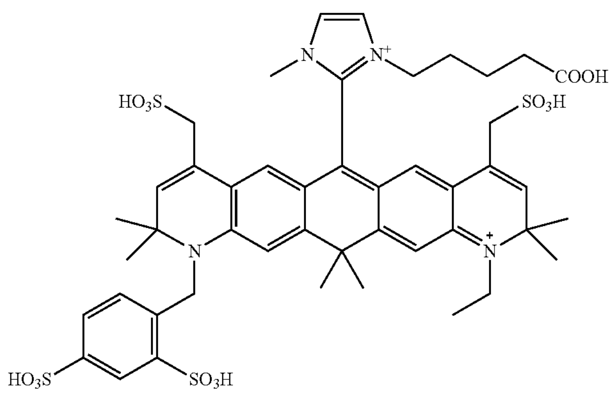 [SMILES: CC[N+]1=c2cc3c(cc2C(CS(=O)(=O)O)=CC1(C)C)=C(c1n(C)cc[n+]1CCCCC(=O)O)c1cc2c(cc1C3(C)C)N(Cc1ccc(S(=O)(=O)O)cc1S(=O)(=O)O)C(C)(C)C=C2CS(=O)(=O)O] | 743[b] | 776[b] |
| 62 | 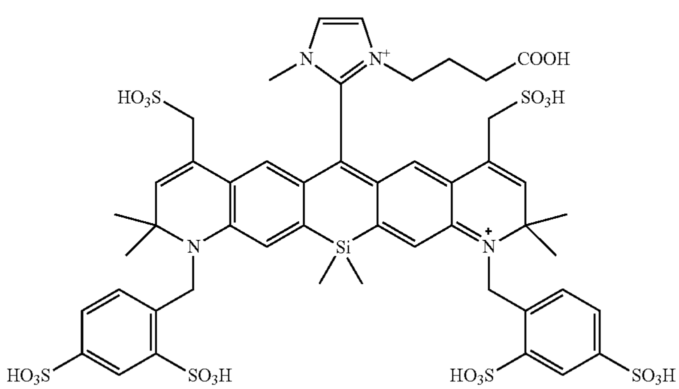 [SMILES: Cn1cc[n+](CCCC(=O)O)c1C1=c2cc3c(cc2[Si](C)(C)c2cc4c(cc21)C(CS(=O)(=O)O)=CC(C)(C)N4Cc1ccc(S(=O)(=O)O)cc1S(=O)(=O)O)=[N+](Cc1ccc(S(=O)(=O)O)cc1S(=O)(=O)O)C(C)(C)C=C3CS(=O)(=O)O] | 791[b] | 817[b] |
| 63 | 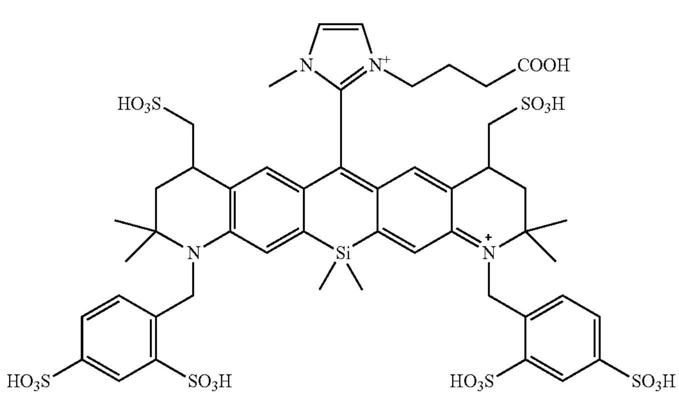 [SMILES: Cn1cc[n+](CCCC(=O)O)c1C1=c2cc3c(cc2[Si](C)(C)c2cc4c(cc21)C(CS(=O)(=O)O)CC(C)(C)N4Cc1ccc(S(=O)(=O)O)cc1S(=O)(=O)O)=[N+](Cc1ccc(S(=O)(=O)O)cc1S(=O)(=O)O)C(C)(C)CC3CS(=O)(=O)O] | 752[b] | 776[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 64 | 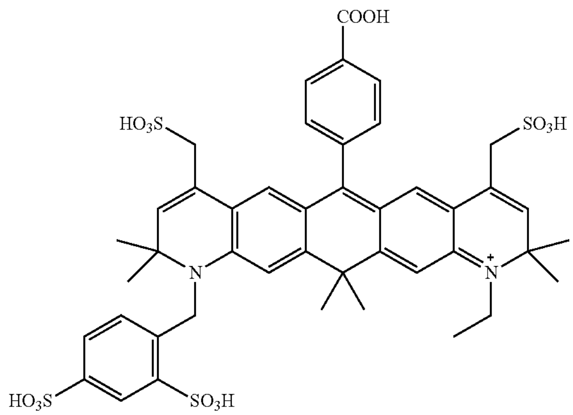 [SMILES: CC[N+]1=c2cc3c(cc2C(CS(=O)(=O)O)=CC1(C)C)=C(c1ccc(C(=O)O)cc1)c1cc2c(cc1C3(C)C)N(Cc1ccc(S(=O)(=O)O)cc1S(=O)(=O)O)C(C)(C)C=C2CS(=O)(=O)O] | 667[b] | 697[b] |
| 65 | 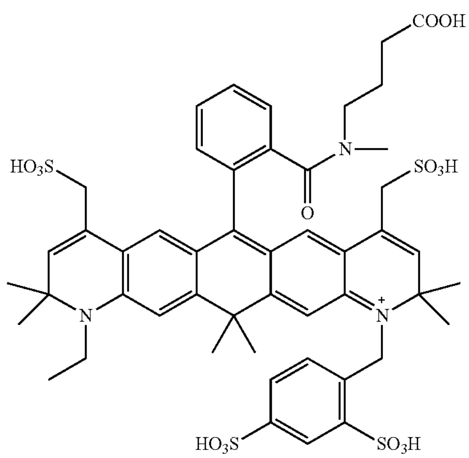 | 679[b] | 706[b] |
| 66 | 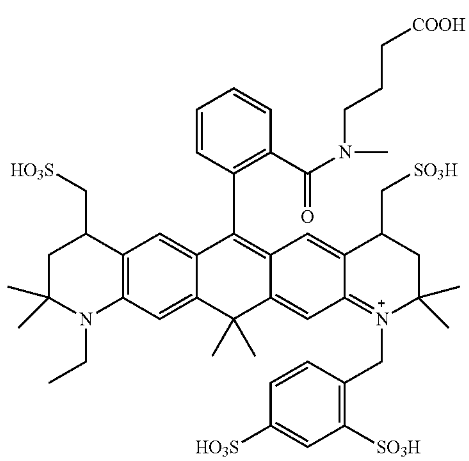 | 645[b] | 665[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 67 | 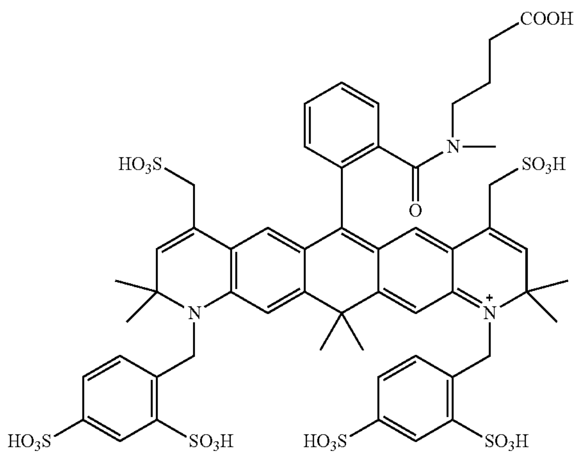 | 679[b] | 707[b] |
| 68 | 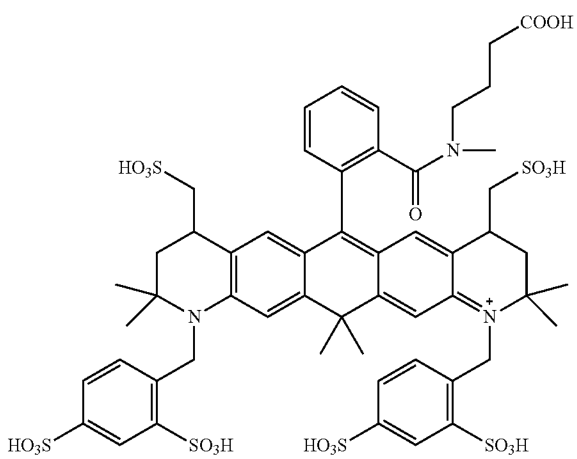 | 645[b] | 666[b] |
| 69 | 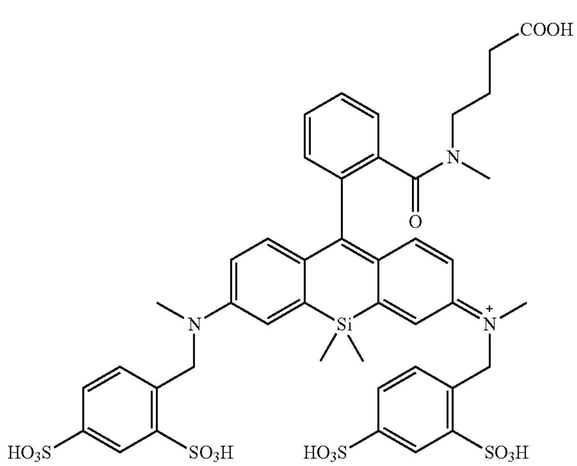 [SMILES: CN(CCCC(=O)O)C(=O)c1ccccc1C1=C2C=C/C(=[N+](\C)Cc3ccc(S(=O)(=O)O)cc3S(=O)(=O)O)C=C2[Si](C)(C)c2cc(N(C)Cc3ccc(S(=O)(=O)O)cc3S(=O)(=O)O)ccc21] | 658[b] | 680[b] |

TABLE 3-continued
general formula (I), examples for X = C(CH$_3$)$_2$ (carborhodamines), X = Si(CH$_3$)$_2$ (silicorhodamines)
| Compound | Structure | $\lambda_{abs}$ [nm] | $\lambda_{fl}$ [nm] |
|---|---|---|---|
| 70 | 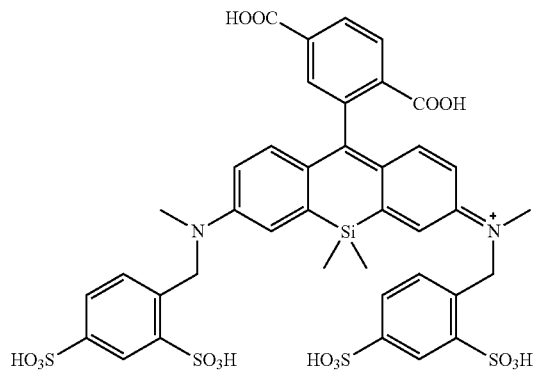 [SMILES: CN(Cc1ccc(S(=O)(=O)O)cc1S(=O)(=O)O)c1ccc2c(c1)[Si](C)(C)C1=C/C(=[N+](/C)Cc3ccc(S(=O)(=O)O)cc3S(=O)(=O)O)C=CC1=C2c1cc(C(=O)O)ccc1C(=O)O] | 649[b] | 670[b] |
| 71 | 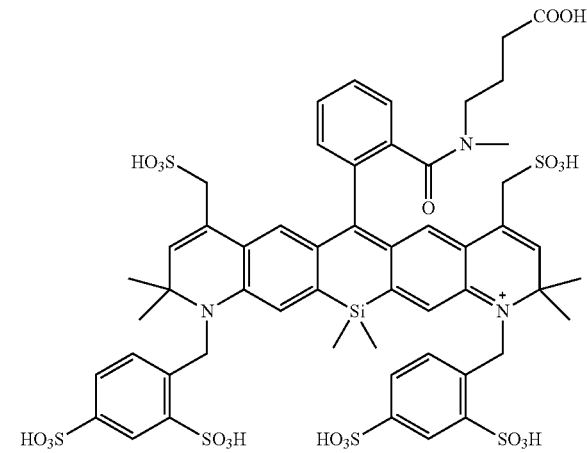 [SMILES: CN(CCCC(=O)O)C(=O)c1ccccc1C1=c2cc3c(cc2[Si](C)(C)c2cc4c(cc21)C(CS(=O)(=O)O)=CC(C)(C)N4Cc1ccc(S(=O)(=O)O)cc1S(=O)(=O)O)=[N+](Cc1ccc(S(=O)(=O)O)cc1S(=O)(=O)O)C(C)(C)C=C3CS(=O)(=O)O] | 722[b] | 752[b] |
| 72 | 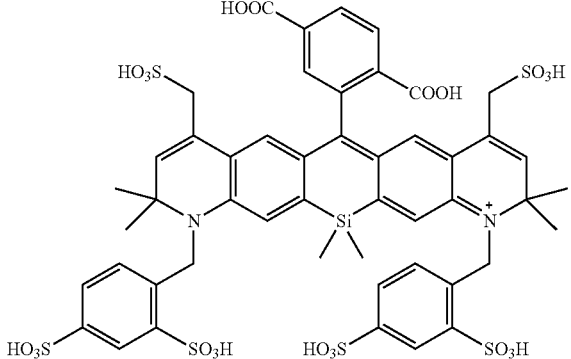 | 711[b] | 740[b] |

TABLE 3-continued general formula (I), examples for X = C(CH$_3$)$_2$ (carborhodamines), X = Si(CH$_3$)$_2$ (silicorhodamines)

| Compound | Structure | $\lambda_{abs}$ [nm] | $\lambda_{fl}$ [nm] |
|---|---|---|---|
| 73 | 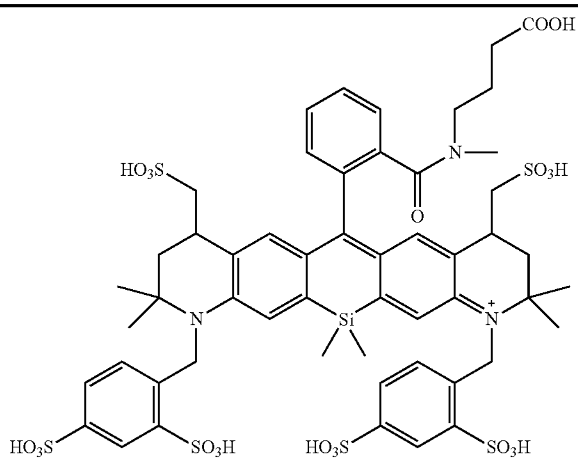 | 686[b] | 708[b] |
| 74 | 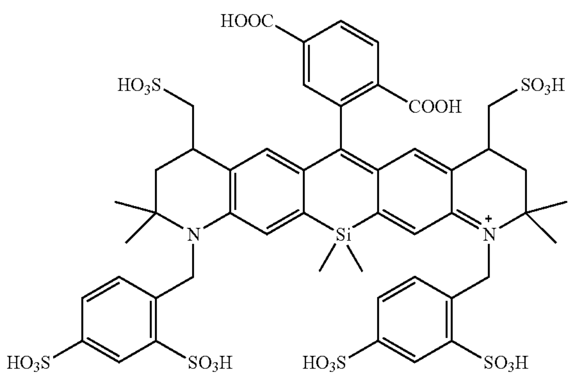 [SMILES: CC1(C)CC(CS(=O)(=O)O)c2cc3c(cc2N1Cc1ccc(S(=O)(=O)O)cc1S(=O)(=O)O)[Si](C)(C)c1cc2c(cc1=C3c1cc(C(=O)O)ccc1C(=O)O)C(CS(=O)(=O)O)CC(C)(C)[N+]=2Cc1ccc(S(=O)(=O)O)cc1S(=O)(=O)O] | 675[b] | 698[b] |

Solvent: [a]Ethanol, [b]PBS pH 7.4, [c]water/acetonitrile 1:1

TABLE 4 general formula (II), examples for X = C(CH$_3$)$_2$ (carbopyronines), X = Si(CH$_3$)$_2$ (silicopyronines)
1

| Compound | Structure | $\lambda_{abs}$ [nm] | $\lambda_{fl}$ [nm] |
|---|---|---|---|
| 75 | 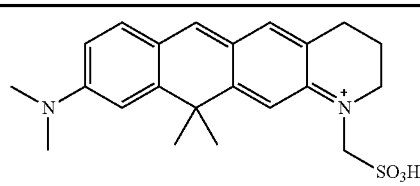 | 597[a] | 621[a] |
| 76 | 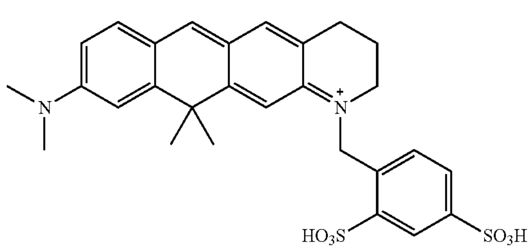 [SMILES: CN(C)c1ccc2c(c1)C(C)(C)c1cc3c(cc1=C2)CCC[N+]=3Cc1ccc(S(=O)(=O)O)cc1S(=O)(=O)O] | 596[b] | 622[b] |

TABLE 4-continued
general formula (II), examples for X = C(CH₃)₂ (carbopyronines), X = Si(CH₃)₂ (silicopyronines)
| Compound | Structure | $\lambda_{abs}$ [nm] | $\lambda_{fl}$ [nm] |
|---|---|---|---|
| 77 | 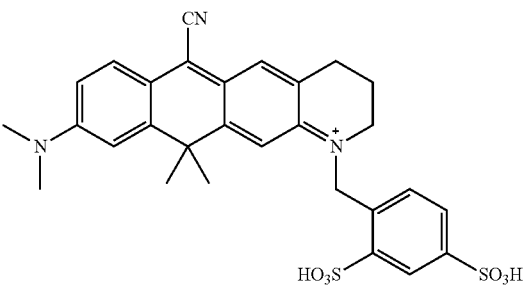 [SMILES: CN(C)c1ccc2c(c1)C(C)(C)c1cc3c(cc1=C2C#N)CCC[N+]=3Cc1ccc(S(=O)(=O)O)cc1S(=O)(=O)O] | 730[b] | 751[b] |
| 78 | 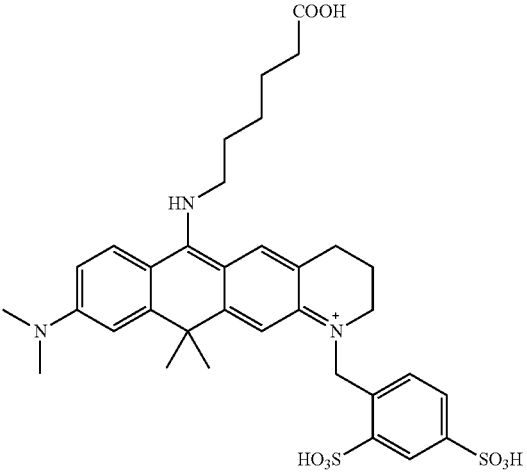 [SMILES: CN(C)c1ccc2c(c1)C(C)(C)c1cc3c(cc1=C2NCCCCCC(=O)O)CCC[N+]=3Cc1ccc(S(=O)(=O)O)cc1S(=O)(=O)O] | 468[a]<br>463[b] | 609[b] |
| 79 | 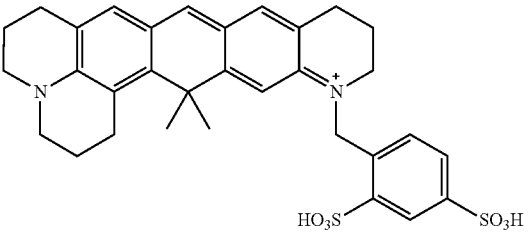 [SMILES: CC1(C)c2c(cc3c4c2CCCN4CCC3)C=c2cc3c(cc21)=[N+](Cc1ccc(S(=O)(=O)O)cc1S(=O)(=O)O)CCC3] | 627[b] | 649[b] |
| 80 | 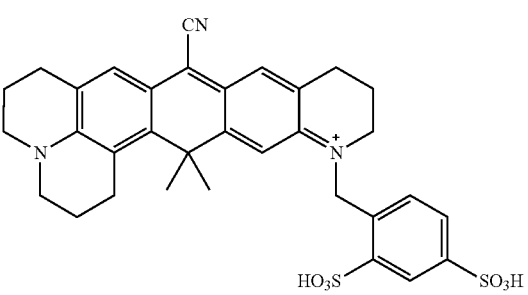 [SMILES: CC1(C)c2c(cc3c4c2CCCN4CCC3)C(C#N)=c2cc3c(cc21)=[N+](Cc1ccc(S(=O)(=O)O)cc1S(=O)(=O)O)CCC3] | 739[b] | 761[b] |

TABLE 4-continued general formula (II), examples for X = C(CH₃)₂ (carbopyronines), X = Si(CH₃)₂ (silicopyronines)

| Compound | Structure | $\lambda_{abs}$ [nm] | $\lambda_{fl}$ [nm] |
|---|---|---|---|
| 81 | 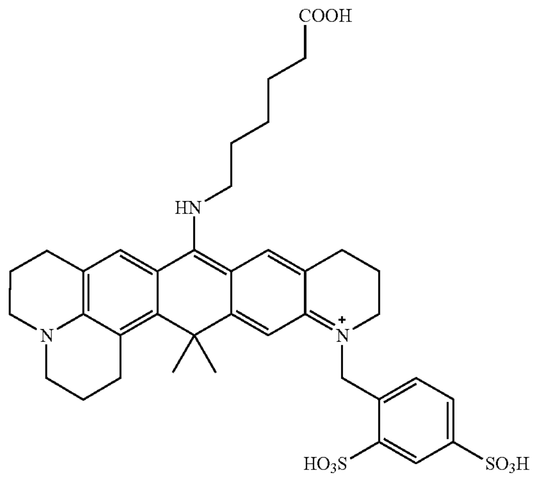 [SMILES: CC1(C)c2c(cc3c4c2CCCN4CCC3)C(NCCCCCC(=O)O)=c2cc3c(cc21)=[N+](Cc1ccc(S(=O)(=O)O)cc1S(=O)(=O)O)CCC3] | 476[b] | 614[b] |
| 82 | 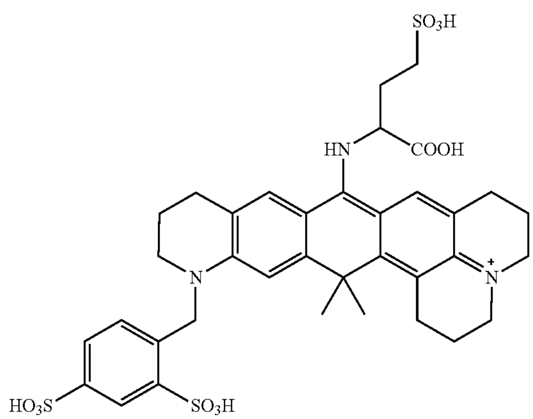 [SMILES: CC1(C)c2cc3c(cc2C(NC(CCS(=O)(=O)O)C(=O)O)=c2cc4c5c(c21)CCC[N+]=5CCC4)CCCN3Cc1ccc(S(=O)(=O)O)cc1S(=O)(=O)O] | | |
| 83 | 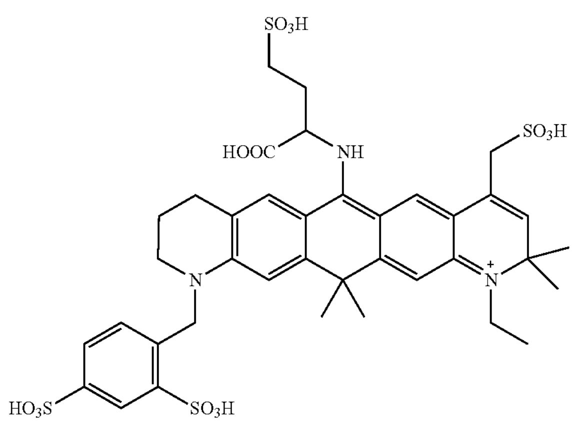 [SMILES: CC[N+]1=c2cc3c(cc2C(CS(=O)(=O)O)=CC1(C)C)=C(NC(CCS(=O)(=O)O)C(=O)O)c1cc2c(cc1C3(C)C)N(Cc1ccc(S(=O)(=O)O)cc1S(=O)(=O)O)CCC2] | | |

TABLE 4-continued general formula (II), examples for X = C(CH$_3$)$_2$ (carbopyronines), X = Si(CH$_3$)$_2$ (silicopyronines)

| Compound | Structure | $\lambda_{abs}$ [nm] | $\lambda_{fl}$ [nm] |
|---|---|---|---|
| 84 | 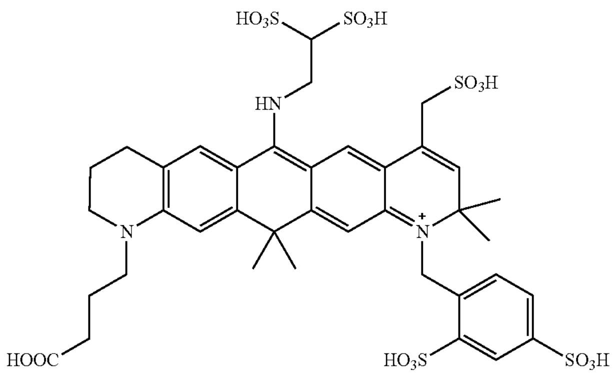 [SMILES: CC1(C)c2cc3c(cc2C(NCC(S(=O)(=O)O)S(=O)(=O)O)=c2cc4c(cc21)=[N+](Cc1ccc(S(=O)(=O)O)cc1S(=O)(=O)O)C(C)(C)C=C4CS(=O)(=O)O)CCCN3CCCC(=O)O] | 490[b] | 644[b] |
| 85 | 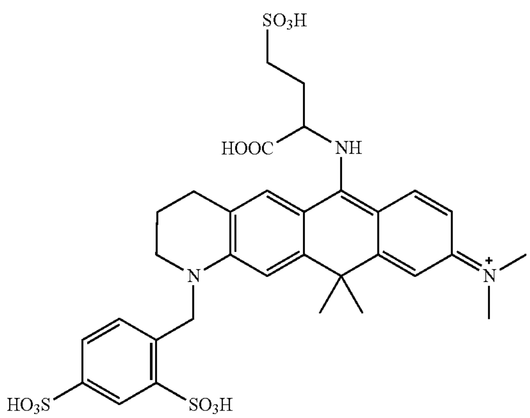 [SMILES: C[N+](C)=C1C=CC2=C(NC(CCS(=O)(=O)O)C(=O)O)c3cc4c(cc3C(C)(C)C2=C1)N(Cc1ccc(S(=O)(=O)O)cc1S(=O)(=O)O)CCC4] | 496[b] | 673[b] |
| 86 | 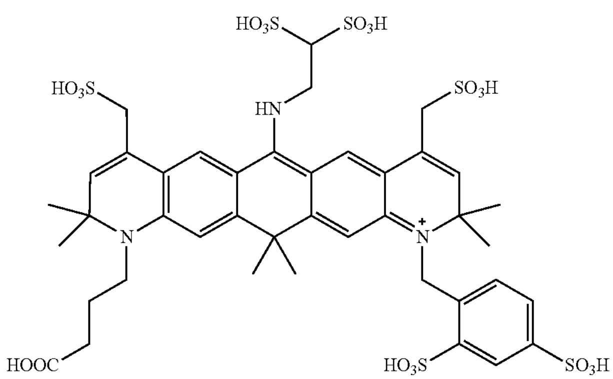 [SMILES: CC1(C)c2cc3c(cc2C(NCC(S(=O)(=O)O)S(=O)(=O)O)=c2cc4c(cc21)=[N+](Cc1ccc(S(=O)(=O)O)cc1S(=O)(=O)O)C(C)(C)C=C4CS(=O)(=O)O)C(CS(=O)(=O)O)=CC(C)(C)N3CCCC(=O)O] | 502[b] | 660[b] |
| 87 | 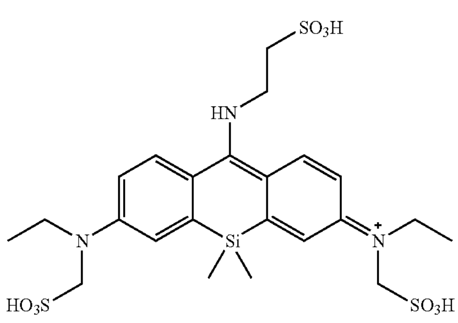 [SMILES: CCN(CS(=O)(=O)O)c1ccc2c(c1)[Si](C)(C)C1=C/C(=[N+](/CC)CS(=O)(=O)O)C=CC1=C2NCCS(=O)(=O)O] | 472[b] | 605[b] |

TABLE 4-continued general formula (II), examples for X = C(CH₃)₂ (carbopyronines), X = Si(CH₃)₂ (silicopyronines)

| Compound | Structure | $\lambda_{abs}$ [nm] | $\lambda_{fl}$ [nm] |
|---|---|---|---|
| 88 | 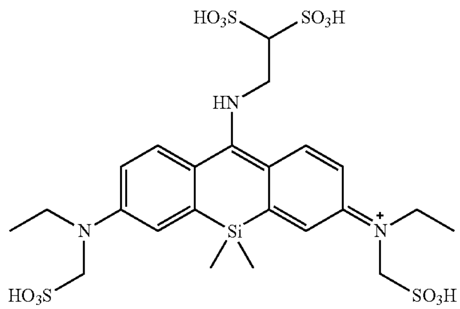 [SMILES: CCN(CS(=O)(=O)O)c1ccc2c(c1)[Si](C)(C)C1=C/C(=[N+](/CC)CS(=O)(=O)O)C=CC1=C2NCC(S(=O)(=O)O)S(=O)(=O)O] | 471[b] | 605[b] |
| 89 | 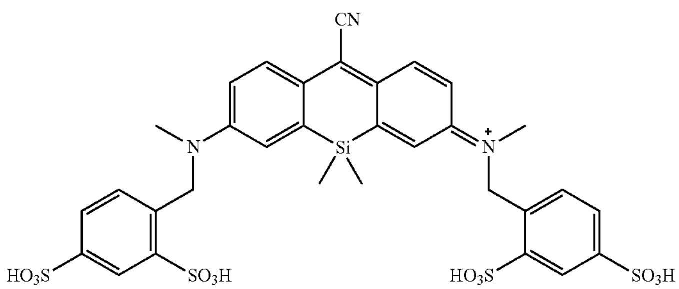 [SMILES: CN(Cc1ccc(S(=O)(=O)O)cc1S(=O)(=O)O)c1ccc2c(c1)[Si](C)(C)C1=C/C(=[N+](/C)Cc3ccc(S(=O)(=O)O)cc3S(=O)(=O)O)C=CC1=C2C#N] | 746[b] | 763[b] |
| 90 | 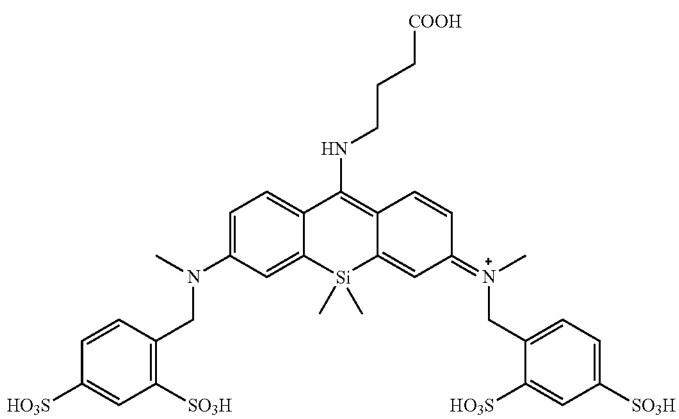 [SMILES: CN(Cc1ccc(S(=O)(=O)O)cc1S(=O)(=O)O)c1ccc2c(c1)[Si](C)(C)C1=C/C(=[N+](/C)Cc3ccc(S(=O)(=O)O)cc3S(=O)(=O)O)C=CC1=C2NCCCC(=O)O] | 483[b] | 637[b] |
| 91 | 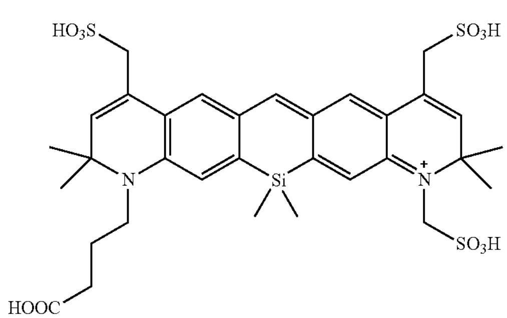 | 715[b] | 738[b] |

TABLE 4-continued
general formula (II), examples for X = C(CH₃)₂ (carbopyronines), X = Si(CH₃)₂ (silicopyronines)
| Compound | Structure | $\lambda_{abs}$ [nm] | $\lambda_{fl}$ [nm] |
|---|---|---|---|
| 92 | 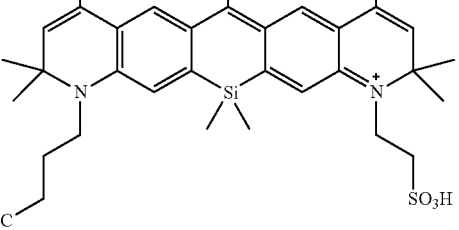 | 817[b] | 841[b] |
| 93 | 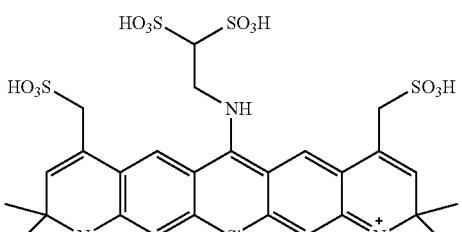 | 516[b] | 695[b] |
| 94 | 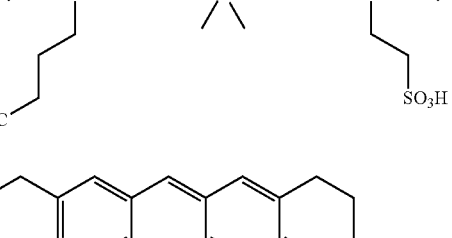 | 670[b] | 693[b] |
| 95 | 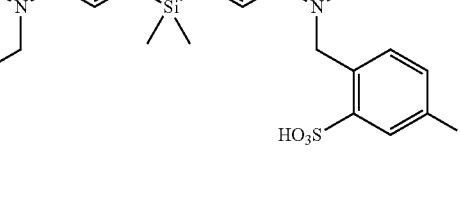 | 489[b] | 661[b] |

TABLE 4-continued general formula (II), examples for X = C(CH₃)₂ (carbopyronines), X = Si(CH₃)₂ (silicopyronines)

| Compound | Structure | $\lambda_{abs}$ [nm] | $\lambda_{fl}$ [nm] |
|---|---|---|---|
| 96 | (structure) | 518[b] | 695[b] |

Solvent: [a]ethanol, [b]PBS pH 7.4, [c]water/acetonitrile 1:1

TABLE 5 general formula (III), examples for X = O (oxazines), X = C(CH₃)₂ (carbazines)

| Compound | Structure | $\lambda_{abs}$ [nm] | $\lambda_{fl}$ [nm] |
|---|---|---|---|
| 97 | (structure) | 649[b] | 667[b] |
| 98 | (structure) | 664[b] | 682[b] |

TABLE 5-continued general formula (III), examples for X = O (oxazines), X = C(CH₃)₂ (carbazines)

| Compound | Structure | $\lambda_{abs}$ [nm] | $\lambda_{fl}$ [nm] |
|---|---|---|---|
| 99 | 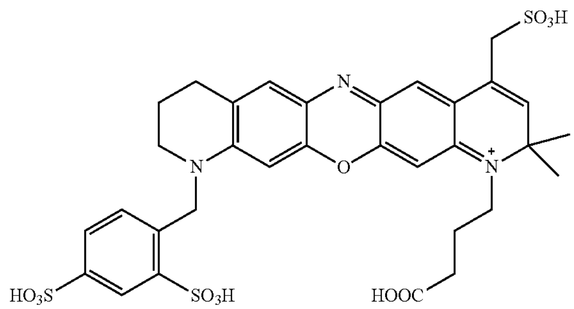 [SMILES: CC1(C)C=C(CS(=O)(=O)O)c2cc3c(cc2=[N+]1CCCC(=O)O)Oc1cc2c(cc1N=3)CCCN2Cc1ccc(S(=O)(=O)O)cc1S(=O)(=O)O] | 682[b] | 700[b] |
| 100 | 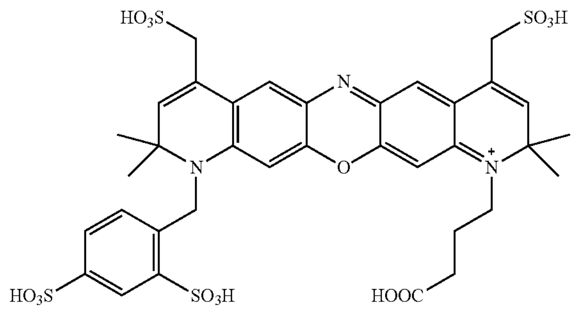 | 701[b] | 718[b] |
| 101 | 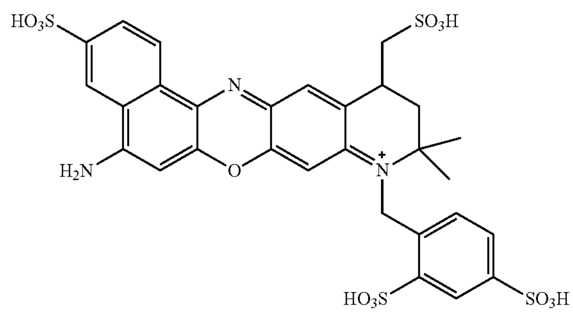 [SMILES: CC1(C)CC(CS(=O)(=O)O)c2cc3c(cc2=[N+]1Cc1ccc(S(=O)(=O)O)cc1S(=O)(=O)O)Oc1cc(N)c2cc(S(=O)(=O)O)ccc2c1N=3] | 647[b] | 678[b] |
| 102 | 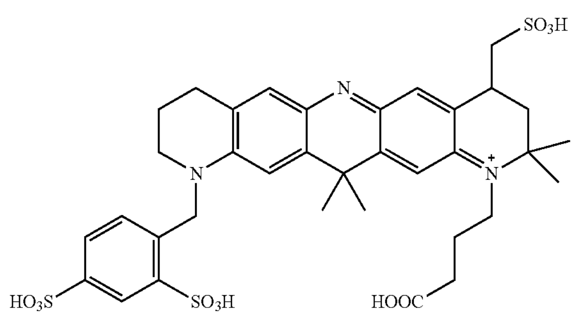 [SMILES: CC1(C)c2cc3c(cc2N=c2cc4c(cc21)=[N+](CCCC(=O)O)C(C)(C)CC4CS(=O)(=O)O)CCCN3Cc1ccc(S(=O)(=O)O)cc1S(=O)(=O)O] | 721[b] | 742[b] |
| 103 | 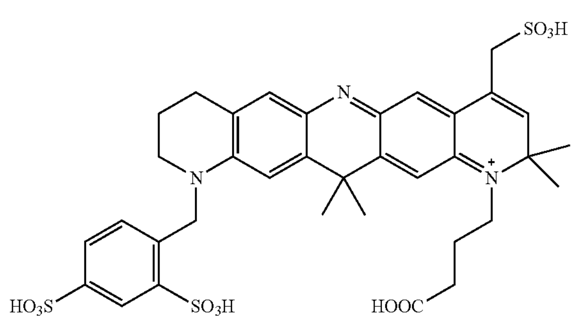 | 740[b] | 761[b] |

TABLE 5-continued general formula (III), examples for X = O (oxazines), X = C(CH$_3$)$_2$ (carbazines)

| Compound | Structure | $\lambda_{abs}$ [nm] | $\lambda_{fl}$ [nm] |
|---|---|---|---|
| 104 | 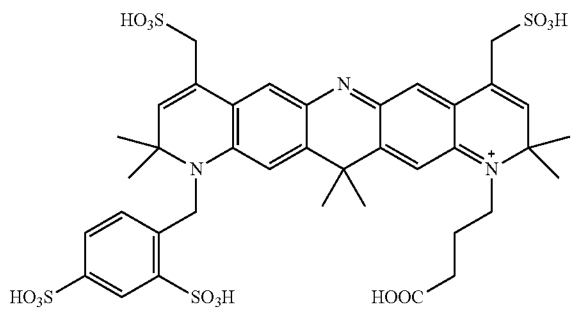 [SMILES: CC1(C)c2cc3c(cc2N=c2cc4c(cc21)=[N+](CCCC(=O)O)C(C)(C)C=C4CS(=O)(=O)O)C(CS(=O)(=O)O)=CC(C)(C)N3Cc1ccc(S(=O)(=O)O)cc1S(=O)(=O)O] | 758[b] | 778[b] |

Solvent: [a]ethanol, [b]PBS pH 7.4, [c]water/acetonitrile 1:1

TABLE 6 general formula (IV), examples for X = O (coumarins), X = NR (carbostyrils)

| Compound | Structure | $\lambda_{abs}$ [nm] | $\lambda_{fl}$ [nm] |
|---|---|---|---|
| 105 | 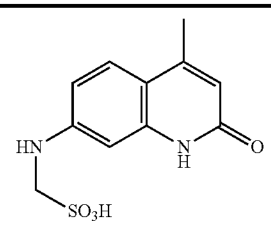 | 355[a] 349[b] | 406[a] 413[b] |
| 106 | 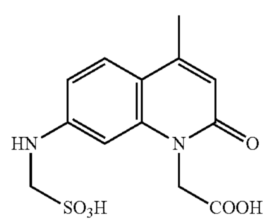 [SMILES: Cc1cc(=O)n(CC(=O)O)c2cc(NCS(=O)(=O)O)ccc12] | 350[b] | 410[b] |
| 107 | 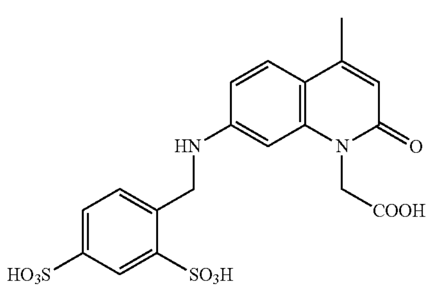 [SMILES: Cc1cc(=O)n(CC(=O)O)c2cc(NCc3ccc(S(=O)(=O)O)cc3S(=O)(=O)O)ccc12] | 351[b] | 413[b] |
| 108 | 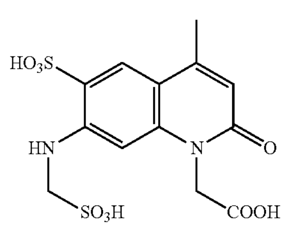 [SMILES: Cc1cc(=O)n(CC(=O)O)c2cc(NCS(=O)(=O)O)c(S(=O)(=O)O)cc12] | 348[b] | 411[b] |

TABLE 6-continued general formula (IV), examples for X = O (coumarins), X = NR (carbostyrils)

| Compound | Structure | $\lambda_{abs}$ [nm] | $\lambda_{fl}$ [nm] |
|---|---|---|---|
| 109 | 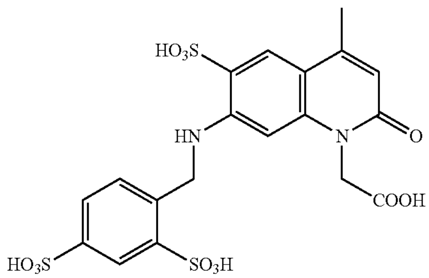 [SMILES: Cc1cc(=O)n(CC(=O)O)c2cc(NCc3ccc(S(=O)(=O)O)cc3S(=O)(=O)O)c(S(=O)(=O)O)cc12] | $349^b$ | $418^b$ |
| 110 | 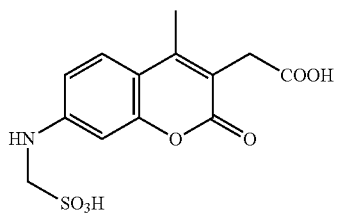 [SMILES: Cc1c(CC(=O)O)c(=O)oc2cc(NCS(=O)(=O)O)ccc12] | $354^b$ | $353^b$ |
| 111 | 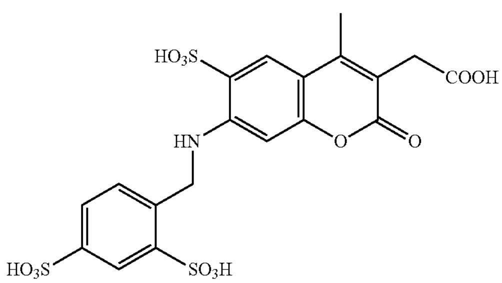 [SMILES: Cc1c(CC(=O)O)c(=O)oc2cc(NCc3ccc(S(=O)(=O)O)cc3S(=O)(=O)O)c(S(=O)(=O)O)cc12] | $348^b$ | $449^b$ |
| 112 | 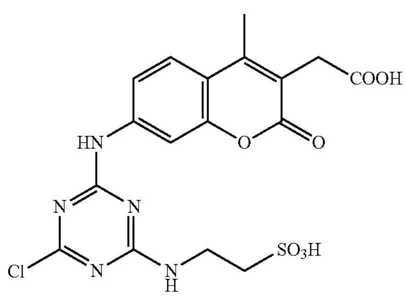 [SMILES: Cc1c(CC(=O)O)c(=O)oc2cc(Nc3nc(Cl)nc(NCCS(=O)(=O)O)n3)ccc12] | $338^b$ | $416^b$ |
| 113 | 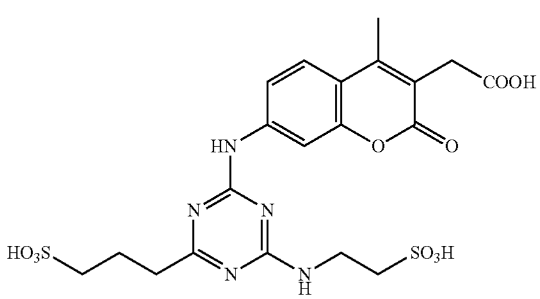 [SMILES: Cc1c(CC(=O)O)c(=O)oc2cc(Nc3nc(CCCS(=O)(=O)O)nc(NCCS(=O)(=O)O)n3)ccc12] | $336^b$ | $423^b$ |

TABLE 6-continued general formula (IV), examples for X = O (coumarins), X = NR (carbostyrils)

| Compound | Structure | $\lambda_{abs}$ [nm] | $\lambda_{fl}$ [nm] |
|---|---|---|---|
| 114 | 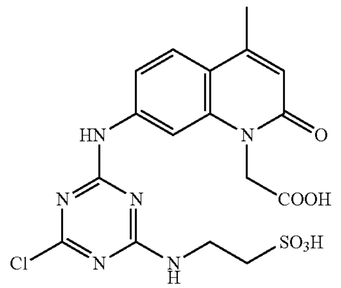 [SMILES: Cc1cc(=O)n(CC(=O)O)c2cc(Nc3nc(Cl)nc(NCCS(=O)(=O)O)n3)ccc12] | 338[b] | 385[b] |
| 115 | 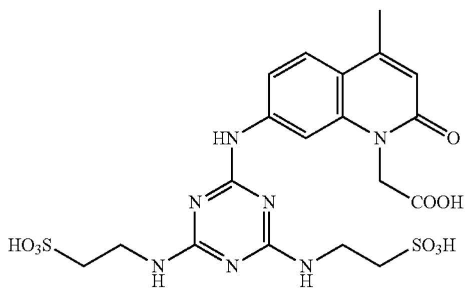 [SMILES: Cc1cc(=O)n(CC(=O)O)c2cc(Nc3nc(NCCS(=O)(=O)O)nc(NCCS(=O)(=O)O)n3)ccc12] | 335[b] | 383[b] |

Solvent: [a]ethanol, [b]PBS pH 7.4, [c]water/acetonitrile 1:1 + 0.1 vol % trifluoroacetic acid In an especially preferable embodiment, compounds of the formula (I) comprise a moiety —$SO_3H$ at positions $R_4$ and/or $R_7$.

A special property of the rhodamines, which—as shown in compounds 6, 10, 11, 12, 19, 20, 25 and 27—are directly substituted on the chromophore with sulfonic acid groups at positions $R_4$ and $R_7$, is that they easily form a lactone or pseudobase in aqueous weakly alkaline solutions. Normally such lactones are adequately stabilized only in aprotic solvents such as acetone or chloroform. In protic solvents the carboxyl group is deprotonated and a slightly more short-wave absorbing and fluorescent zwitterion is formed. In the exemplary compounds, however, colorless compounds are formed due to the strong electron attraction of the indicated substituents, due to internal ester formation and the associated interruption of the conjugated system. If the carboxyl group is not free but is present as an ester or tertiary amide, so-called pseudobases are formed, through nucleophilic attack (hydroxide ions etc.) at the central carbon atom, which is stronger positivized by the electron-attracting substituents, which pseudobases are likewise colorless due to the interruption of the conjugated system. Both reactions are reversible; by changing the pH value, the dielectric constant ("polarity") and/or the capability of hydrogen bridge bonding ("proticity"), the dye can be restored. Therefore such compounds can in principle be used as probes for the properties of their direct environment: Depending on the milieu, the molecules are present in colorless or colored form. Associated therewith is also a sort of fluorogenicity, because the longwave fluorescence appears only in the dye form.

The fluorogenicity of compounds gains importance for modern imaging procedures such as fluorescence imaging of living cells or as molecular switches in microscopic and nanoscopic procedures, e.g. STED, PALM, (d)STORM etc. There are even novel silico-rhodamines developed for this purpose; see for example G. Lukinavicius, K. Umezawa et al. (2013), A near-infrared fluorophore for live-cell super-resolution microscopy for cellular proteins, Nature Chemistry 5, 132-139. But even conventional chromophores are further modified for this type of application, see for example J. B. Grimm, A. J. Sung et al. (2013), Carbofluoresceins and Carborhodamines as Scaffolds for High-Contrast Fluorogenic Probes, ACS Chem. Biol. 8, 1303-1310.

The mentioned subgroup of the novel and inventive dyes provided herein may therefore in principle also be used in such procedures, and should allow significant advances.

A particular subgroup of the compounds according to the invention is fluorescence quenchers. These dyes are not fluorescent themselves, but can act as acceptors for the emission of fluorescent compounds. A widespread area of use of such quenchers is for instance the measurement of the geometry (distances, size, and arrangement of molecular groups) or the reactivity (enzyme activity, reaction speeds, etc.) using Förster resonance energy transfer (FRET). The fluorescence of the donor can only appear when the distance between donor and acceptor exceeds a critical value. Below this distance, the fluorescence of the donor is quenched by the acceptor (=quencher) which is not fluorescent by itself. An overview of the bioanalytical applications of the FRET technology is provided for example by A. Roda, M. Guardigli, E. Micheline, M. Mirasoli, Nanobioanalytical luminescence: Förster-type energy transfer methods, Anal. Bioanal. Chem. 393, 2009, 109-123.

Examples of quenchers according to the invention are compounds 14, 15, 16 and 17. These rhodamines represent a further development of the dyes designated as "violamines" because of their magenta-colored solutions, see for example H. E. Fierz-David, Künstliche Organische Farbstoffe [Artificial Organic Dyes], Springer-Verlag, Berlin, 1926, p. 276ff. However, also the structure of other dye classes may be modified in this way. Examples according to the invention include compounds 49, 50 and 51 from the class of carbopyronines.

Fluorescence quenchers according to the invention include in particular a group B having structure

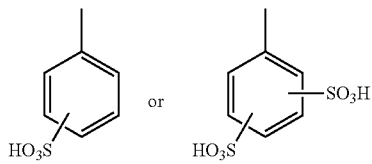

and in particular at least one group B, selected from

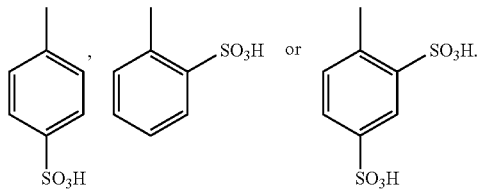

The aromatic ring of the group B in compounds having fluorescence-quencher properties is thus directly bound to the nitrogen atom.

An important advantage of the present invention is that the novel compounds of the general formulae (I)-(IV), which are suitable in particular for use as a marker group in processes for the detection of analytes, can be produced by a simple and economical procedure and are easy to handle. One significant advantage of the invention lies therefore in the commercial availability or economical production of starting dyes according to methods known to a person skilled in the art. Many known, readily fluorescent and photostable dyes of the classes of coumarins, xanthenes, carbopyronines, and oxazines etc. can be reacted in simple chemical reactions into compounds according to the invention. Thereby, on the one hand, the entire visible spectrum is covered because the starting chromophore can be selected from a wide range. On the other hand, due to the possibility to vary the substituents virtually as desired, the absorption and fluorescence maxima, fluorescence quantum yield and decay period can be greatly varied and thus selected as desired. This allows to reduce or avoid interferences with disrupting substances in the samples.

The compounds of the formulae (I)-(IV) are produced in accordance with the procedures described in more detail in the examples.

In particular in the case of the rhodamines, the production is especially simple and economical: rhodamines commercially available or easily producible in accordance with known methods are converted to the leuco form. The leuco form is alkylated at the amino groups with a multiply sulfonated aryl-alkyl halide and subsequently oxidized to the dye according to the invention (see example: Compound 6).

On the other hand, rhodamines according to the invention can be produced in a known manner from commercial 3',6'-dichlorofluorane, e.g. by reaction with a multiply sulfonated benzylamine easily in a known manner (see example: Compound 18).

In these two procedures, the group B is subsequently incorporated in the dye. This method is not limited to rhodamines, but can also be applied to other compounds of the general formulae (I)-(IV).

It is also possible however to produce the compounds according to the invention of the formulae (I)-(IV) by synthesis of the ring system using building blocks that already contain the group B. Such a procedure is shown by way of example below for compounds 102 and 103.

EXAMPLES FOR THE PREPARATION OF PRECURSOR COMPOUNDS 2-(bromomethyl)-benzene Sulfonic Acid 1st stage: 2-(Hydroxymethyl)-benzene Sulfonic Acid 25 g (120 mmol) of 2-formyl-benzene sulfonic acid sodium salt (M=208.17 g/mol) are suspended in 400 ml of methanol, mixed portionwise with 3.63 g (96 mmol) of sodium borohydride and stirred at room temperature. The reaction is monitored by thin-layer chromatography (water/acetonitrile 1:9). After about 90 minutes mixture is suctioned off and the filtrate is evaporated until dry. For complete drying, the residue is treated with dichloromethane and concentrated again. This process is repeated until a nearly colorless powder results. Yield: 100%.

NMR in $D_2O$: 7.8 ppm (1H, DvD); 7.5 ppm (1H, DvD); 7.4 ppm (1H, DvT); 7.3 ppm (1H, DvT); 4.9 ppm (2 H, S)

2nd stage: 2-(bromomethyl)-benzene Sulfonic Acid Sodium Salt (M=273.08 q/mol)

21 g (100 mmol) of 2-(hydroxymethyl)-benzene sulfonic acid sodium salt (M=210.19 g/mol) are stirred with 9.6 g of sodium bromide and 240 ml of 48% hydrobromic acid on the oil bath at about 80° C. for 10 hours.

The reaction is monitored by thin-layer chromatography (see above).

After cooling it is evaporated until dry and the light yellow residue is refluxed for 30 minutes in 400 ml of acetone. After cooling the mixture is suctioned off and the residue is washed with acetone.

The filtrate is concentrated and the resultant viscous broth is stirred with 300 ml of diethyl ether and suctioned off. It is washed with diethyl ether until a light beige solid results, which is air-dried. Yield: 64%; NMR in $D_2O$: 7.9 ppm (1H, DvD); 7.6 ppm (1H, DvD); 7.5 ppm (1H, DvT); 7.4 ppm (1H, DvT); 5.0 ppm (2 H, S)

4-(bromomethyl)-benzene-1,3-disulfonic Acid

Production According to DE60105258T2

1st Stage:
4-(Hydroxymethyl)-benzene-1,3-disulfonic Acid 15 g (48 mmol) of 4-formyl-benzene-1,3-disulfonic acid disodium salt (M=310.21 g/mol as a hydrate) are suspended in 400 ml of methanol and mixed portionwise with 1.5 g (40 mmol) of sodium borohydride and stirred at room temperature for about 90 minutes. The reaction is monitored by thin-layer chromatography (water/acetonitrile 1:9). The reaction mixture is evaporated until dry. The result is a colorless powder. Yield: 100%;

NMR in $D_2O$: 8.1 ppm (1H, D); 7.9 ppm (1H, DvD); 7.7 ppm (1H, D); 4.9 ppm (2H, S)

2nd Stage: 4-(bromomethyl)-benzene-1,3-disulfonic Acid 12 g (38 mmol) of 4-(hydroxymethyl)-benzene-1,3-disulfonic acid disodium salt (M=312.25 g/mol) are stirred with 4.5 g of lithium bromide and 100 ml of 48% hydrobromic acid on the oil bath at 80° C. for 10 hours. The reaction is monitored by thin-layer chromatography (see above).

After cooling it is evaporated until dry and the light yellow residue is heated for 30 minutes in 400 ml of acetone to reflux. After cooling it is suctioned off and the solid is washed with acetone. The solid is dried in the exsiccator. Yield: 82%;

NMR in $D_2O$: 8.2 ppm (1H, D); 7.9 ppm (1H, DvD); 7.7 ppm (1H, D); 4.95 ppm (2H, S)

4-(bromoethyl)-benzene-1,3-disulfonic Acid

Produced According to Makarova et al., Polyelectrolytes from Vinylaromatic Monomers which Contain Sulfo Groups, Chimiceskie reaktivy I preparaty 33 (1971), 22-29.

50 ml of 2-bromoethyl benzene are added dropwise under ice cooling to 50 ml of concentrated sulfuric acid. Subsequently, 150 ml of cooled 65% oleum are added dropwise, so that the internal temperature remains less than 50° C. After that it is heated to 80° C. for two hours.

The somewhat cooled reaction mixture is poured onto 500 ml of ice and set to a pH of 9 with solid barium carbonate. This is suctioned from the barium sulfate produced, and this is again washed with cold water. The filtrate is concentrated, whereby a yellowish substance broth is obtained. This is stirred with methanol, suctioned, and dried.

4-(bromoethyl)-benzene Sulfonic Acid

Produced According to DE3023112A1 from 2-bromoethyl Benzene in 30% Oleum and Chlorosulfonic Acid. The Resultant Sulfonyl Chloride is Hydrolyzed in Water/Acetonitrile 42 g of 30% of oleum are added to a round-bottomed flask and cooled in an ice bath. 29 g of 2-bromoethyl-benzene are dissolved in 13 g of acetonitrile and added dropwise to the oleum such that the temperature remains below 25° C. Then it is heated in the oil bath to 40-60° C. and at this temperature 46 g of chlorosulfonic acid are added dropwise. Subsequently it is heated for another hour to 100-120° C.

The reaction mixture is poured onto 500 ml of ice, the resulting precipitate is suctioned off, washed three times with ice-cold water, and dried. 36 g of crude product are obtained.

For purification recrystallization from 400 ml of heptane is performed. Mixture is decanted from the brown, oily sediment. From the supernatant, colorless crystals of the desired product are precipitated in the ice bath. After drying 20 g are obtained.

For hydrolysis of the sulfochloride it is refluxed in a mixture of water and acetonitrile until the reaction is complete (DC-test). The strongly acidic solution is set to a pH of 6.5 with sodium hydroxide and after concentrating 22.7 g of 4-(bromoethyl)-benzene sulfonic acid sodium salt remains (mixed with formed sodium chloride).

This substance is commercially marketed as sulfonic acid or sodium sulfonate.

4-(aminoethyl)-benzene Sulfonic Acid 50 ml of concentrated sulfuric acid are cooled in an ice bath to 0° C. 50 ml of 2-phenethylamine are added dropwise, so that the internal temperature does not rise above 40° C.

After that 150 ml of 30% oleum are added dropwise, so that the temperature does not rise above 70° C. At the end of addition it is heated for 30 minutes to 80° C. The reaction mixture is then added dropwise to 1.5 l of a mixture of diethyl ether and THF (1:1), whereby the product precipitates as a colorless substance. It is suctioned off and dried. 71 g are obtained.

Examples for the preparation of compounds according to the invention.

Compound 6: Alkylation of a Rhodamine with 4-(bromomethyl)-benzene-1,3-disulfonic Acid

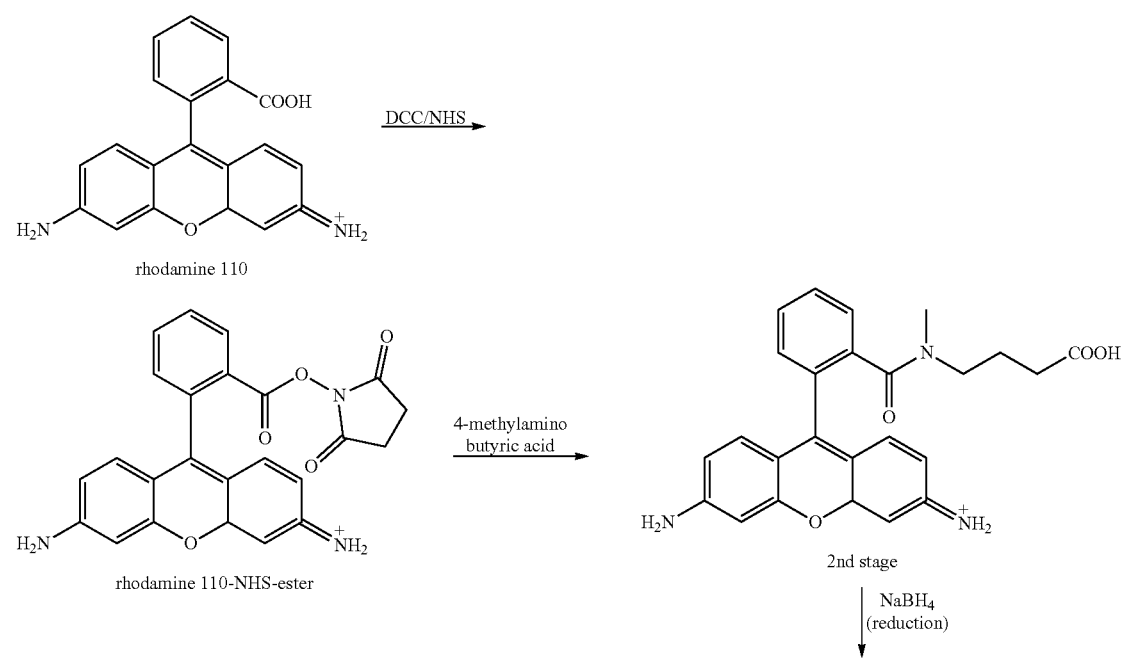

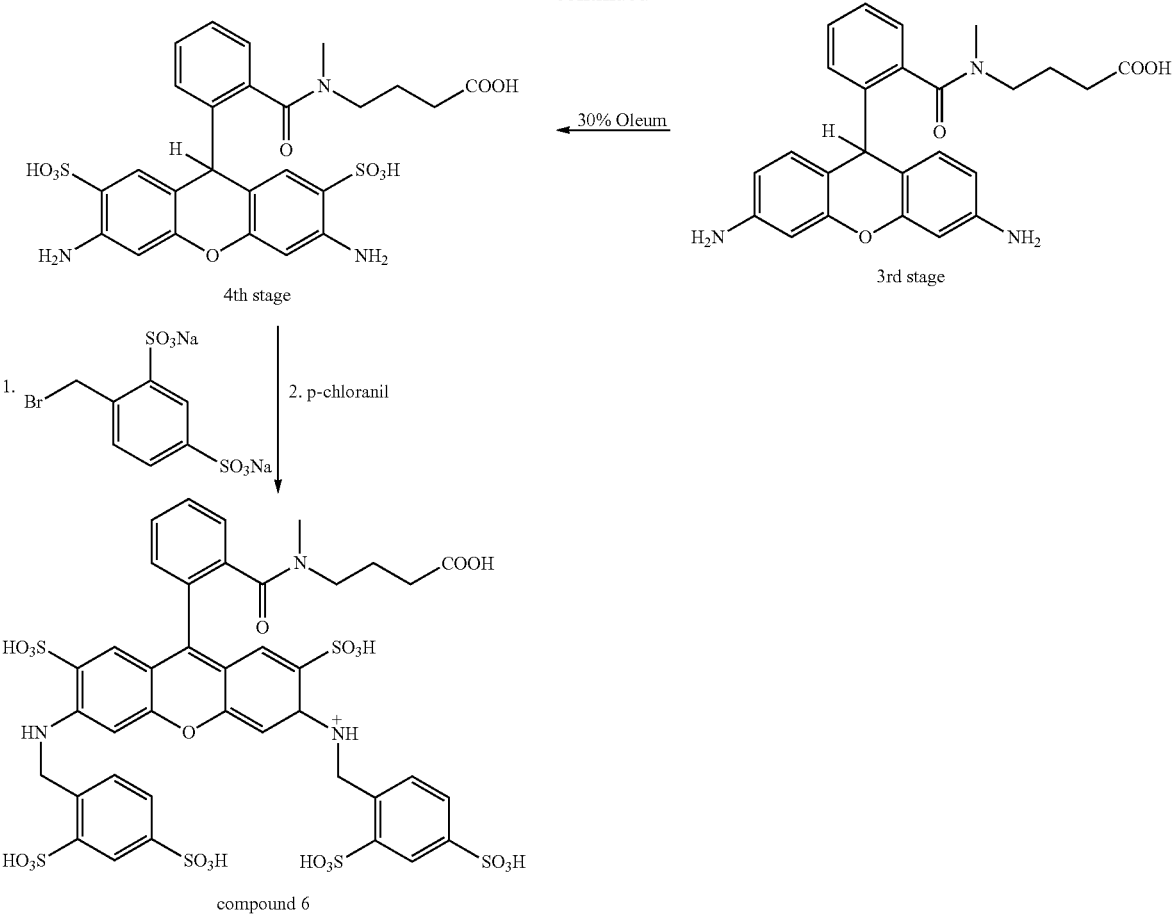

compound 6

1st and 2nd stage: rhodamine 110-chloride is activated and reacted with 4-methylaminobutyric acid (see EP1576059B1).

3rd stage: The dye of the 2nd stage is reduced as described in B. M. Kinsey, A. I. Kassis et al, Synthesis and Biological Studies of Iodinated ($^{127}/^{125}$I) Derivatives of Rhodamines 123, J. Med. Chem. 30, 1987, 1757-1761.

4th stage: The solid resulting from the 3rd stage is sulfonated in 30% oleum according to the known instruction (see U.S. Pat. No. 4,345,017A).

5th stage, Compound 6: The isolated sulfonation product is suspended with 700 mg of 4-(bromomethyl)-benzene-1, 3-disulfonic acid disodium salt, 160 mg of potassium iodide and 130 mg of potassium carbonate in approx. 25 ml of dimethyl formamide (DMF) and stirred for 30-60 minutes at 100° C. on the oil bath. The turbid solution turns reddish.

The reaction mixture is stirred into 500 ml of acetone, the resulting precipitate is filtered and washed two times with acetone. The filter residue is dissolved in 200 ml of water, mixed with 100 ml of acetone and 200 mg of p-chloranil, and stirred at room temperature for one and a half hours, wherein the oxidation process is monitored by thin-layer chromatography. Chromatography purification follows.

Compound 7 (Compound 6-NHS-Ester)

100 mg of compound 6 are dissolved in 10 ml DMF, mixed with 35 mg of TSTU and 100 µl of Hünig's base, then stirred at room temperature for 6 hours. The NHS-ester is precipitated by dropwise addition of the reaction mixture in 100 ml of diethyl ether. the precipitate is suctioned off, washed with diethyl ether and dried in the vacuum exsiccator over phosphorous pentoxide.

Compound 8 (Compound 6-streptavidin-conjugate)

2 mg of streptavidin (IBA, content approx. 75%) are dissolved under cautious swirling in a glass vial with 1 ml of PBS buffer (pH 7.4) and 50 µl of a 0.2 M sodium hydrogen carbonate solution, which is set to a pH of 9 with sodium hydroxide. The clear solution has a pH-value of 8.3.

40.5 µl of a solution of 170 µg of compound 7 in 50 µl of dry DMSO are added; this corresponds to a dye-streptavidin ratio of 4:1.

The reaction solution is kept for two hours at room temperature and then kept overnight in the refrigerator at 4° C.

Purification is performed in the usual manner over superfine Sephadex G25 (column length 40 cm, diameter 2.5 cm) with PBS buffer as the eluent. The first colored zone contains the streptavidin conjugate.

The DOL can be calculated from the absorption spectrum of the conjugate fraction by the known procedure.

Absorption and fluorescence spectrum of the streptavidin-conjugate are shown in FIG. 6. In comparison with FIG. 5 (Compound 6) one can recognize in the absorption spectrum the absorption caused in the conjugate by the streptavidin at 280 nm.

Compound 18: Production of a Dye from Dichlorofluorane

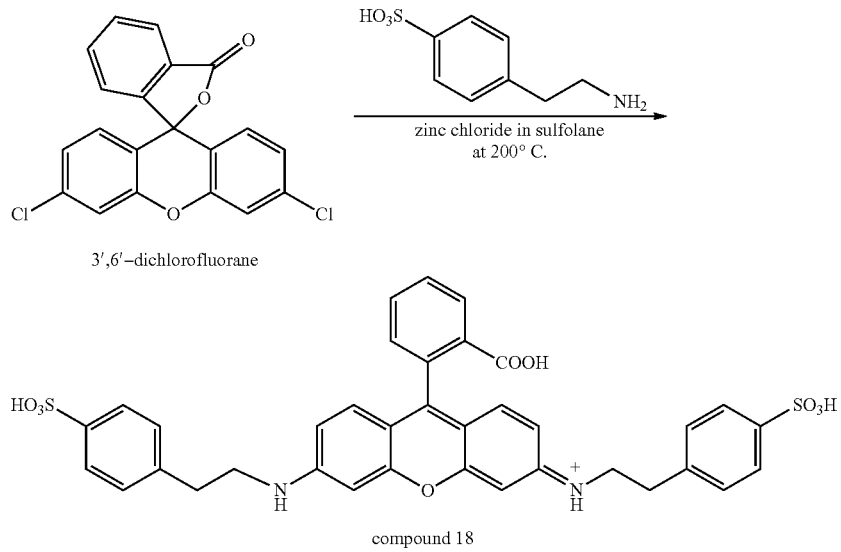

10 g of 3',6'-dichlorofluorane are heated with 15 g of zinc chloride and 15 g of 4-(aminoethyl)-benzene sulfonic acid in 30 ml of sulfolane for 4 hours at 200° C. Thereby a red oil is obtained from the colorless reaction broth.

After cooling it is stirred with a mixture of ethanol and water (1:1) and suctioned off. The filtrate (250 ml) is stirred into 1200 ml of acetone and 200 ml of THF, whereby the product precipitates as red flakes. It is suctioned off, washed several times with acetone and dried in the vacuum exsiccator. Purification is by chromatography. Yield: 40%

Compound 38: Production of an Aryl-Substituted Carbopyronine

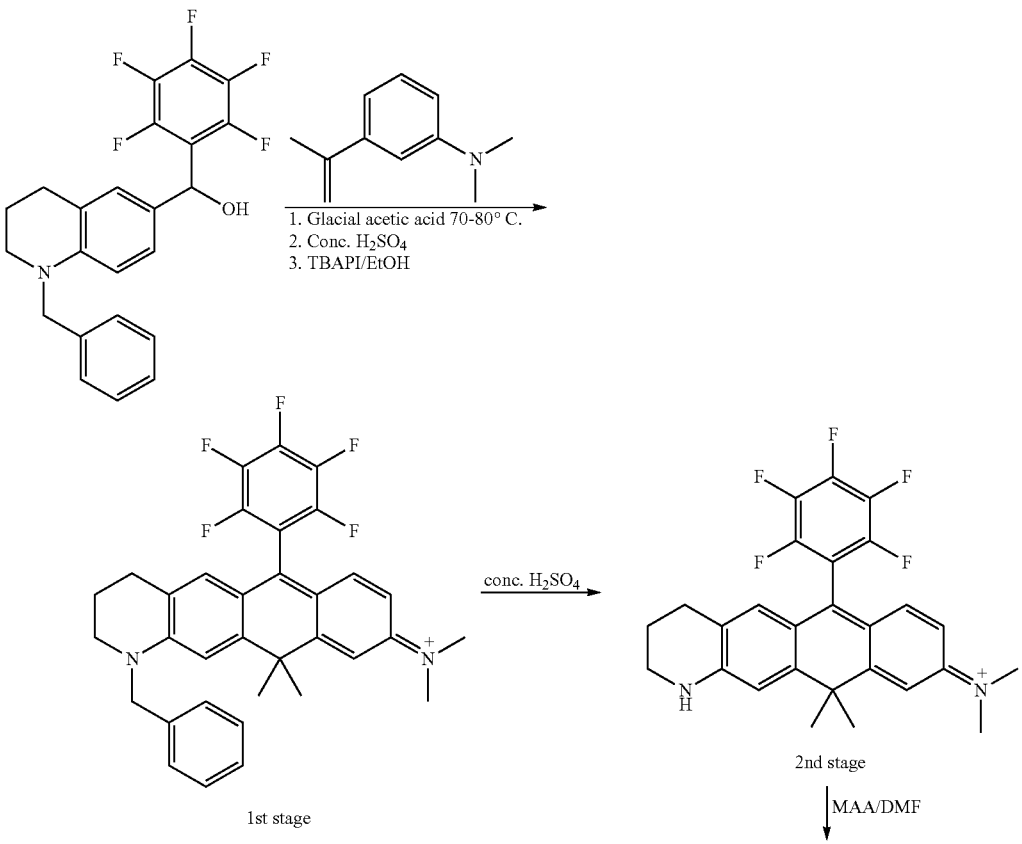

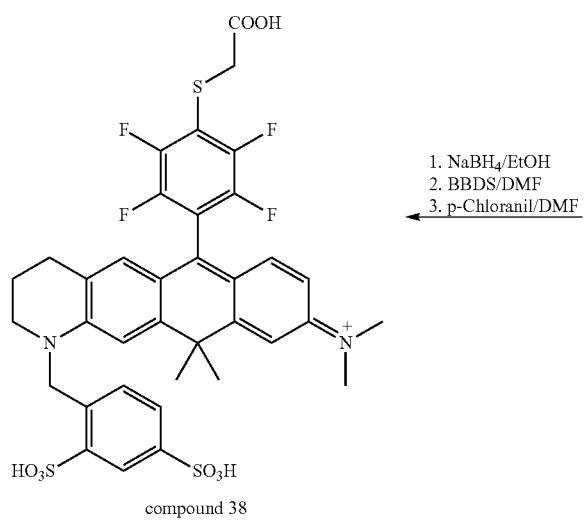

compound 38

1st Stage

The dye is produced according to the procedure for preparing carbopyronins (see EP1173519) from (1-benzyl-1,2,3,4-tetrahydroquinoline-yl)(perfluorophenyl)methanol and N,N-dimethyl-3-(prop-1-en-2-yl)aniline.

2nd Stage 2.6 g of the dye (1st stage) are dissolved in 30 ml of conc. sulfuric acid and stirred at room temperature. The reaction is monitored by HPLC and is completed after 5 h. Mixture is added dropwise to 250 ml of ethanol, mixed with 350 ml of ice water and 100 ml of a 5% sodium perchlorate solution. The precipitate is suctioned off and dried in the vacuum exsiccator. The dye is purified by chromatography. Yield: 89%; HPLC-MS: $M^+$=471.19

3rd Stage 2 g of the dye (2nd stage) are dissolved in 50 ml of dry DMF and mixed with 7 eq. mercaptoacetic acid (MAA). It is heated to 85° C. The reaction is monitored by HPLC and is completed after 90 min. The reaction mixture is cooled and added dropwise to 450 ml of a 5% sodium perchlorate solution. The precipitated dye is suctioned off, vacuum dried, and purified again by chromatography. Yield: 73%; HPLC-MS: $M^+$=543.17

4th Stage, Compound 38

500 mg of the dye (3rd stage) are dissolved in 30 ml of dry acetonitrile and mixed portionwise under protective gas with 5×2 ml of a sodium borohydride solution saturated at 40° C. and stirred for 30 min. The reaction solution comprising the reduced dye is concentrated until dry, the residue is taken up in 30 ml of dry DMF, mixed with 5 eq. 4-(bromomethyl)-benzene-1,3-disulfonic acid (BBDS) and heated to 90° C. The alkylation is monitored by HPLC and is completed after 1 h. The reaction solution is cooled to 50° C. and mixed with 2.5 eq. of p-chloranil. The oxidation to the dye is completed after 30 min. The reaction solution is added dropwise to 400 ml of diethyl ether, the precipitated dye is suctioned off and the crude product purified by chromatography. Yield: 79%; HPLC-MS: $M^+$=793.13

Compound 55: Production of an Aryl-Substituted Carbopyronine

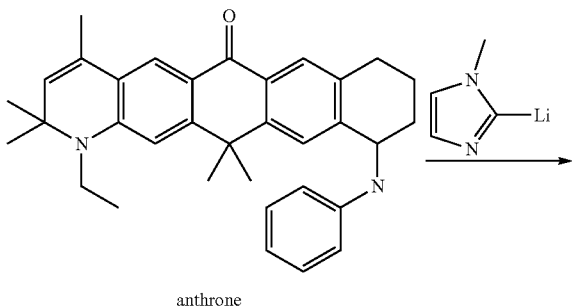

anthrone

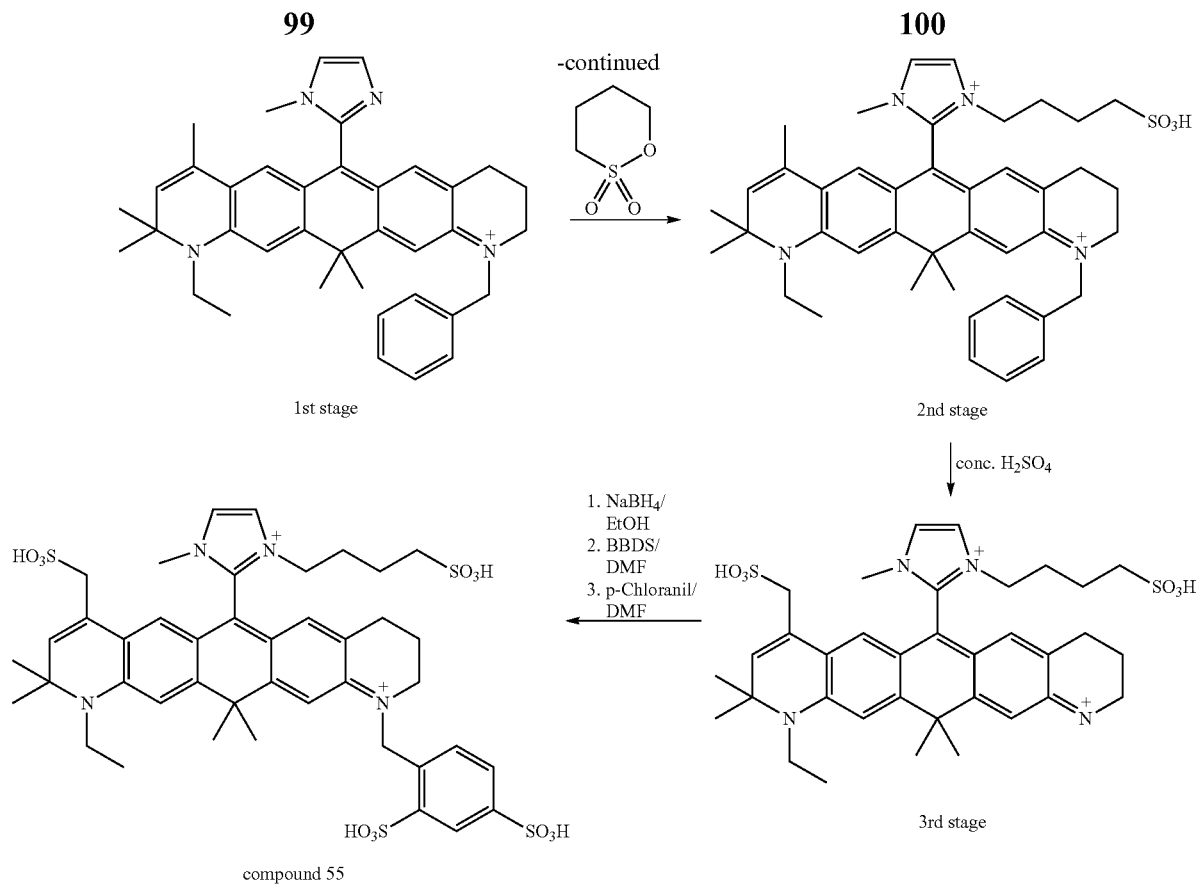

compound 55

1st Stage 0.25 g of 1-methyl-1H-imidazol are provided in 20 ml of dry tetrahydrofurane, mixed dropwise under protective gas at −78° C. with 1 eq. of n-butyllithium and after addition is completed, stirred for 30 minutes. 150 mg of anthrone (produced according to DE102010042634A1) are dissolved in 10 ml of dry tetrahydrofurane and added dropwise at −78° C. to the reaction mixture. The reaction solution is allowed to warm slowly to room temperature and is stirred for another 3 h before it is added under stirring to 100 ml of ethanol+2 ml of trifluoroacetic acid. The solution is evaporated until dry and the dye is purified by chromatography. Yield: 83%; HPLC-MS: $M^+=555.35$

2nd Stage 100 mg of the dye (1st stage) are suspended in 4 ml of butane sultone and heated to 100° C. The reaction is monitored by UV-VIS-spectroscopy and is completed after 2 h. The reaction mixture is added into 50 ml of water:acetonitrile 800:200 and stirred for 30 min. The dye solution is purified by chromatography. Yield: 85%; HPLC-MS: $M^+=692.37$

3rd Stage

Preparation is analogous to synthesis of the 2nd stage of compound 38 with a yield of 74%; HPLC-MS: $M^+=682.28$

4th Stage, Compound 55

Preparation is analogous to synthesis of compound 38 with a yield of 79%; HPLC-MS: $M^+=931.24$

Compounds 79, 80 and 81: Production of a Carbopyronine

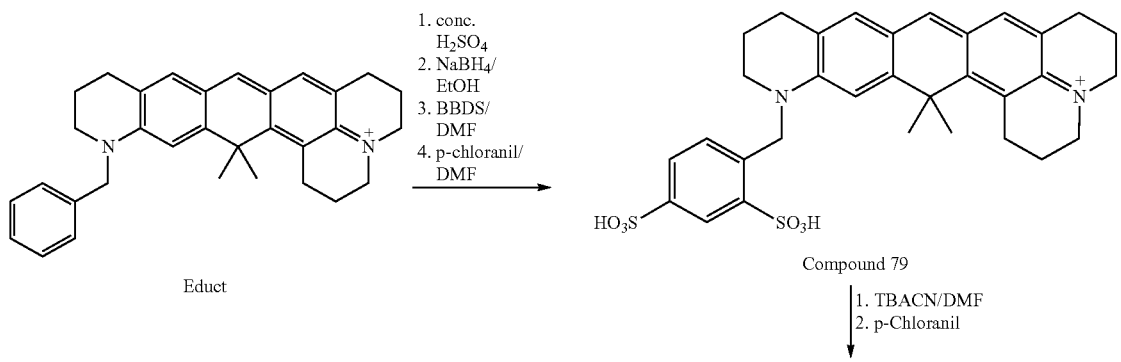

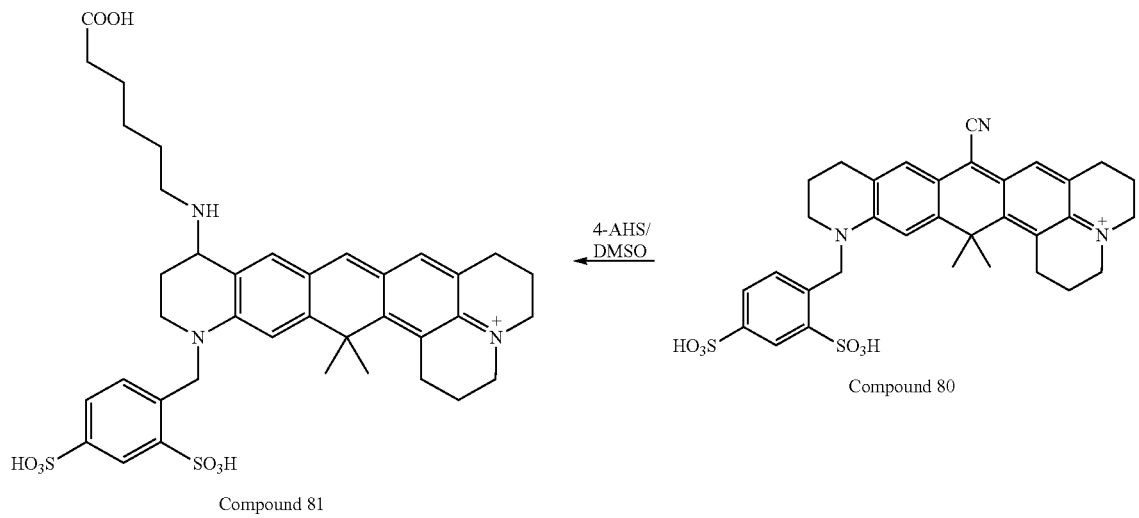

Compound 81

Compound 80

1st Stage, Compound 79

1 g of educt (produced according to DE102010042634A1) is dissolved in 15 ml of conc. sulfuric acid and stirred at room temperature. The reaction is monitored by HPLC and is completed after 5 hours. The reaction solution is added onto 400 ml of ice water, mixed with 200 ml of dichloromethane and adjusted to pH 5 with sodium hydroxide. The organic phase is separated and extracted with dichloromethane. The combined organic phases are dried over anhydrous sodium sulfate, filtered and evaporated until dry. The residue is suspended in 100 ml of ethanol and mixed dropwise with a solution of 0.17 g of sodium borohydride in 5 ml of ethanol. The reaction mixture is stirred for 1 h at room temperature. The dye is reduced and dissolves completely. It is evaporated until dry and the residue suspended under protective gas in 20 ml of DMF. It is mixed with 2 eq. of 4-(bromomethyl)benzene-1,3-disulfonic acid (BBDS) and heated to 100° C. The reaction is monitored by thin-layer chromatography and is completed after 40 min. It is added dropwise into 150 ml of ethanol, mixed with 0.54 g of p-chloranil and heated to 60° C. The Oxidation is completed after 20 minutes. It is evaporated and purified by chromatography. Yield: 63%; HPLC-MS: M$^+$=607.2

2nd Stage, Compound 80

500 mg of compound 79 are suspended in 40 ml of DMF and mixed with 1.5 eq. of tetrabutyl ammonium cyanide under protective gas. It is stirred for 1-2 hours at room temperature and then oxidized with p-chloranil. Under vigorous stirring 300 ml of diethyl ether is added dropwise and it is decanted from the oily precipitated dye. The residue is taken up in 15 ml of water/acetonitrile 9:1 and purified by chromatography. Yield: 60%; HPLC-MS: M$^+$=632.2

3rd Stage, Compound 81

200 mg of Compound 80 are dissolved in 6 ml of DMSO/water 1:1 and mixed with 6 eq. 4-aminohexane acid (4-AHS) in 2 ml DMSO/water 7:3. 6 eq. di-isopropyl ethylamine is added, the reaction mixture is stirred at room temperature and the reaction is monitored by HPLC. The mixture is diluted with 35 ml of water and purified by chromatography. Yield: 67%; HPLC-MS: M$^+$=708.24

Compounds 89 and 90: Production of a Silicopyronine

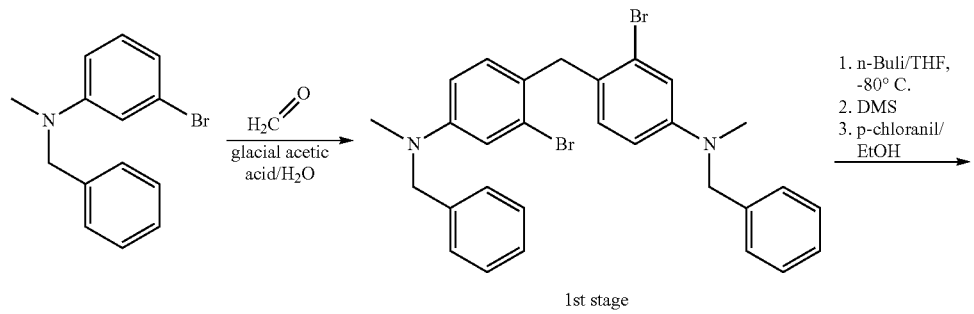

1st stage

-continued

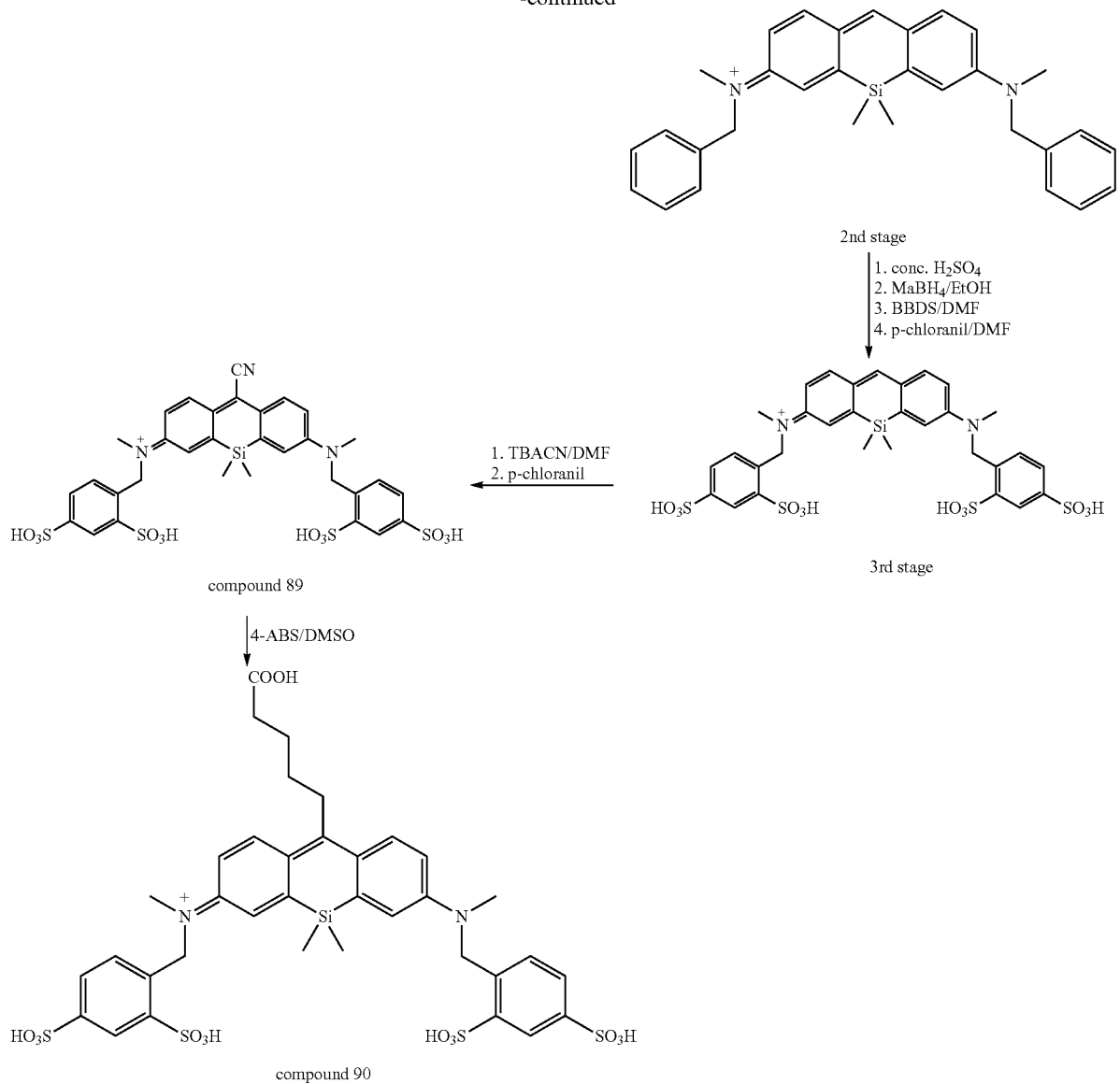

1st Stage 7.1 g of 3-bromo-N-benzyl-N-methylaniline are dissolved in 40 ml of glacial acetic acid, mixed with 2.53 g of a 37% formalin solution, and heated for 3-4 hours to 80° C. It is poured onto 250 ml of ice water and mixed with 100 ml of dichloromethane. It is then neutralized with sodium hydroxide and extracted with dichloromethane. The combined organic phases are dried over anhydrous sodium sulfate, the solvent is removed, and the residue purified by chromatography. Yield: 61%; HPLC-MS: MH$^+$=563.07

2nd Stage 3 g of 4,4'-methylene-bis-(N-benzyl-3-bromo-N-methylaniline) are mixed in 120 ml of dry THE and at −80° C. with n-butyllithium. After addition is complete it is stirred for 1 hour at −80° C. 1.38 ml of dichlorodimethylsilane are added dropwise to the reaction mixture. Then it is allowed to slowly warm to room temperature and stirred for another 2 hours. It is poured into 500 ml of ethanol, mixed with 1.57 g of p-chloranil, and refluxed for 30 min. The deep blue reaction mixture is evaporated under vacuum until dry. The residue is purified by chromatography. Yield: 68%; HPLC-MS: M$^+$=461.2

3rd Stage 1 g of the dye (stage 2) is dissolved in 12 ml of conc. sulfuric acid and stirred for 5 h at room temperature. It is added dropwise into water/acetonitrile 1:1, neutralized with aqueous sodium hydrogen carbonate and extracted with dichloromethane. The combined organic phases are dried over anhydrous sodium sulfate and evaporated on a rotary evaporator until dry. The residue is taken up in 40 ml of ethanol and mixed at room temperature with 0.5 eq. of sodium borohydride. It is again evaporated until dry. The residue is taken up in dimethyl formamide and mixed under protective gas with 4 eq. of 4-(bromoethyl)-benzene-1,3-disulfonic acid and heated to 100° C. It is oxidized by the addition of p-chloranil and purified by chromatography. Yield: 73%; HPLC-MS: M+=781.07

4th Stage, Compound 89

500 mg of the dye (stage 3) are suspended in in 40 ml of DMF and mixed under protective gas with 1.5 eq. of tetrabutylammonium cyanide (TBACN). It is stirred for 1-2 hours at room temperature and then oxidized with p-chloranil. It is then added dropwise with vigorous stirring to diethyl ether after which one decants from the oily precipitated dye. The residue is taken up in 15 ml of water/acetonitrile 9:1 and purified by chromatography. Yield: 56%; HPLC-MS: M+=806.06

5th Stage, Compound 90

300 mg of the dye (stage 4) are dissolved in 6 ml of DMSO/water at 1:1 and mixed with 10 eq. of 4-aminobutyric acid (4-ABA) dissolved in 2 ml of DMSO/water 1:1. The reaction mixture is stirred at room temperature and the reaction is monitored by HPLC. The reaction mixture is diluted with 35 ml of water and purified by chromatography. Yield: 67%; HPLC-MS: M+=882.12

Compounds 102 and 103: Production of a Carbazine

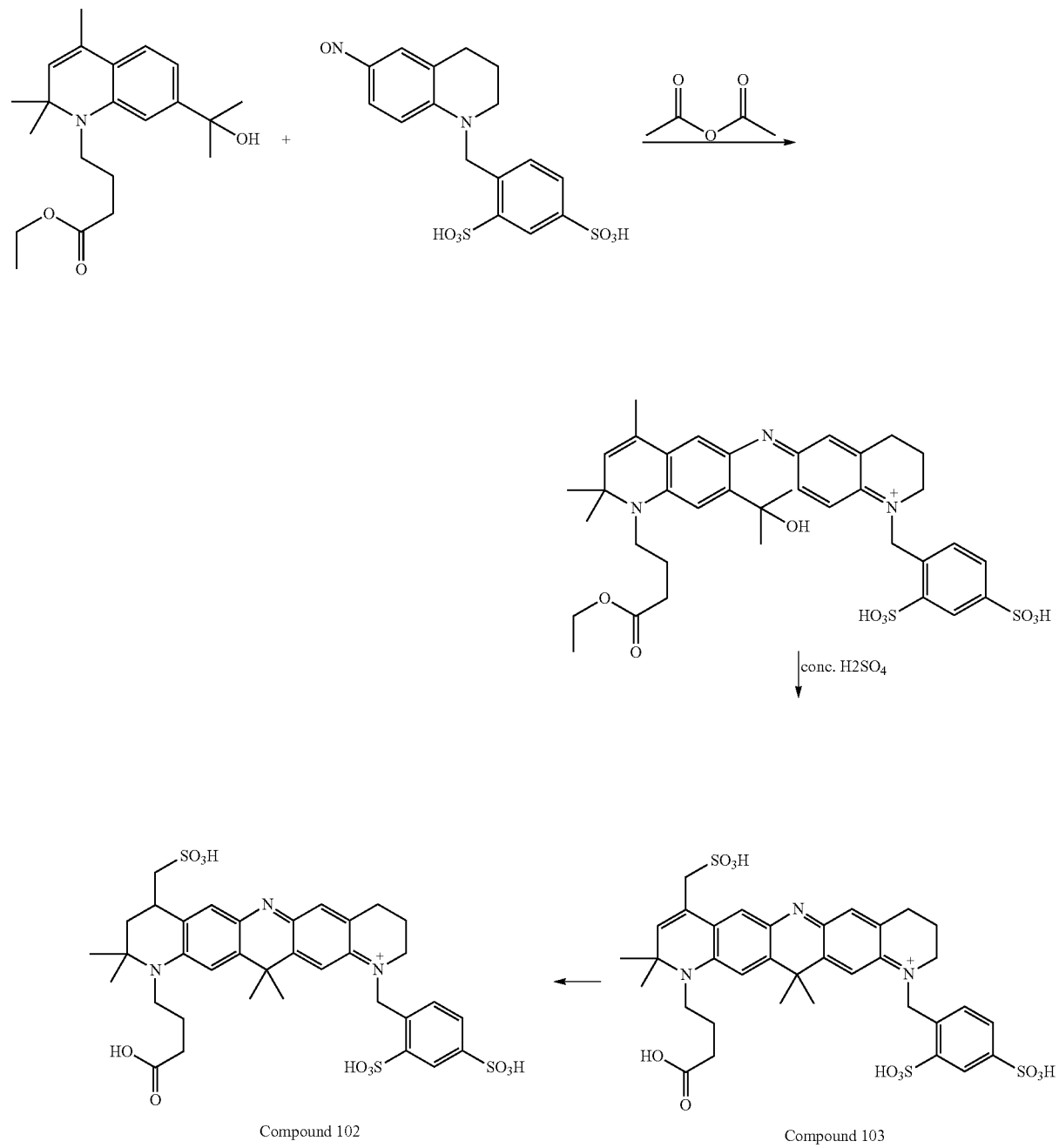

Compound 102

Compound 103

The two educts of the actual dye synthesis are produced by a procedure known to a person skilled in the art:

4-(7-(2-hydroxypropyl)-2,2,4-trimethyl-1,2-dihydroquinolinyl)-butyric acid ethyl ester is obtained from commercial aminobenzoic acid ester in three stages. First the 2,2,4-trimethyl-1,2-dihydroquinoline framework is built according to A. Rosowsky, E. J. Modest, 2,2,4-Trimethyl-1,2-dihydroquinolines. Preparation and Nuclear Magnetic Resonance Studies, J. Org. Chem. 30, 1965, 1832-1837. This is followed by a Grignard reaction with methylmagnesium iodide so as to obtain the tertiary alcohol. Then the amino group is alkylated with 4-iodobutyric acid ethyl.

4-(6-nitroso-1,2,3,4-tetrahydroquinolinyl)-benzyl-1,3-disulfonic acid is obtained from commercial 1,2,3,4-tetrahydroquinoline in two stages. The starting material is initially alkylated with 4-(bromoethyl)-benzene-1,3-disulfonic acid. The alkylation product is then nitrosated with sodium nitrite in hydrochloric acid solution. The synthesis to Compound 103 proceeds as shown in two stages. The connection of the two educts occurs in acetic acid anhydride as described in J. Griffiths, R. Cox, Light absorption and stability properties of some near-IR indamine dyes related to Bindschedler's green, Dyes and Pigments 42, 1999, 29-34. Then follows complete ring closure by treatment of the bridged intermediate stage with conc. sulfuric acid. In this step, saponification of the ethyl ester also occurs, as well as the known sulfonation of the allylic methyl group on the dihydroquinoline ring. The dye is isolated by pouring the sulfuric acid reaction into a mixture of ether/dioxane and then purified by chromatography. Through subsequent catalytic hydrogenation of the dihydroquinoline ring with hydrogen and Pd on activated charcoal in an autoclave the Compound 102 is quantitatively obtained. Total yield: 30%

Compound 106: Production of a Sulfonated Carbostyril

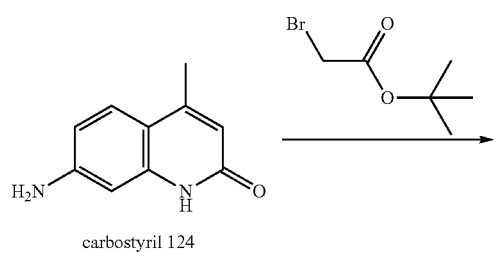

carbostyril 124

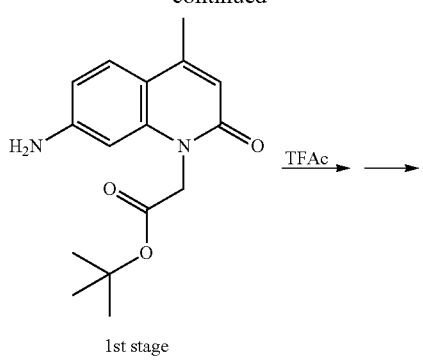

1st stage

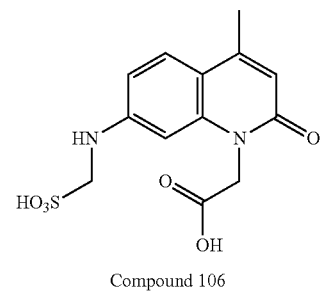

Compound 106

1st Stage 2 g of carbostyril 124 (7-amino-4-methylquinoline-2(1H)-one, CAS: 19840-99-4, Fluorochem) are suspended in 20 ml of dimethyl formamide (DMF) and mixed under protective gas with 480 mg of a 60% suspension of sodium hydride in paraffin oil. The reaction mixture is stirred for 60 min. 1.8 ml of bromoacetic acid tert-butyl ester are added dropwise and stirred for another 24 h. It is added dropwise to 200 ml of water. The formed precipitate is suctioned off, dried, and chromatographed.

Compound 106:

The solid of the 1st stage is dissolved in 60 ml of dichloromethane/trifluoroacetic acid 1:1 and stirred for 18 h. The solvent is removed under vacuum and the residue mixed with 10 ml of acetonitrile. The product crystallizes. The mixture is suctioned off, dried under vacuum, and the solid suspended in 30 ml of water. By addition of 10% sodium hydroxide, it is dissolved completely (pH 10). 2 g of sodium pyrosulfite are added to 20 ml of water, mixed with 5 ml of a 37% formaldehyde solution, and refluxed. The carbostyril solution is added dropwise and after addition is complete, is refluxed for 2 h. The reaction mixture is cooled and purified by chromatography. Total yield: 43%; HPLC-MS: $MH^+$=327.07

Compounds 112 and 113: Introduction of Alkyl Sulfonic Acids by Means of a 1,3,5-Triazine

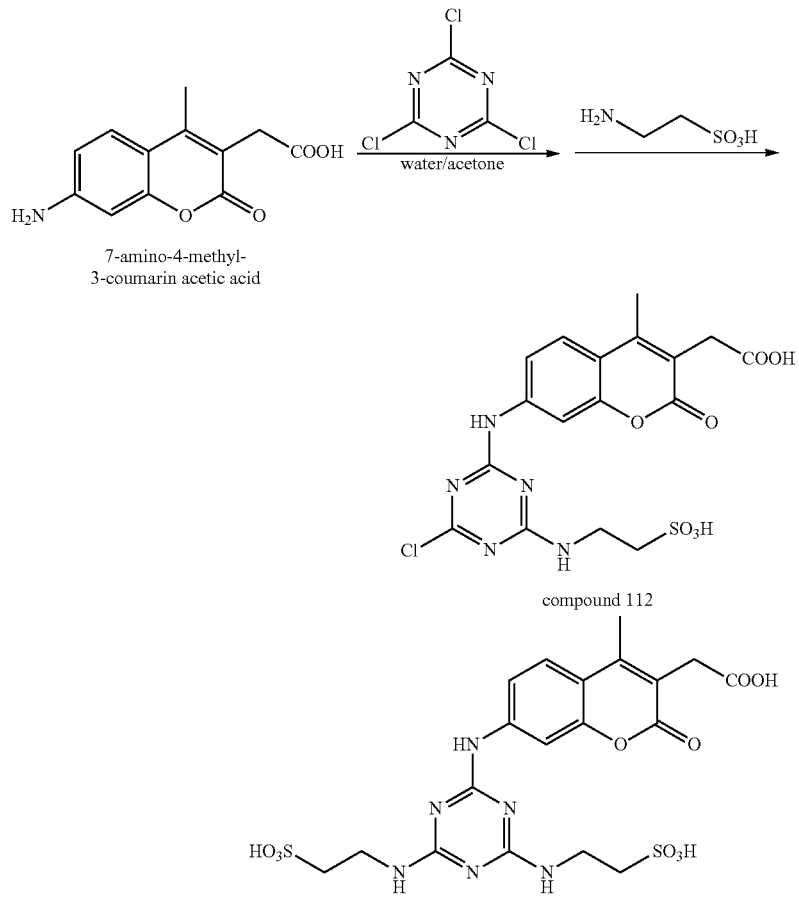

Compound 112

100 mg of 7-amino-4-methyl-3-coumarin acetic acid (Sigma, CAS: 106562-32-7) are suspended in water and completely dissolved by the addition of a sodium carbonate solution (pH 8). 79 mg of cyanuric chloride are dissolved in 3 ml of acetone and added dropwise into 25 ml of ice water. The solution of coumarin is slowly added dropwise at 0° C. into the suspension obtained The pH value is maintained at 8-9 by the addition of 5% sodium hydroxide. After addition is completed, it is stirred for another 10 min at 0° C.

The reaction mixture is warmed to room temperature and mixed dropwise with a solution of 55 mg of taurine in 4 ml of water. During the addition, the temperature is slowly increased to 40-45° C. and the pH-value maintained at 8-9 by the addition of 5% sodium hydroxide. The reaction is monitored by HPLC and is completed after 60 min. The reaction mixture is purified by chromatography. Yield: 82%; HPLC-MS: MH$^+$=470.06

Compound 113:

100 mg of 7-amino-4-methyl-3-coumarin acetic acid are suspended in water and completely dissolved by the addition of a sodium carbonate solution (pH 8). 79 mg of cyanuric chloride are dissolved in 3 ml of acetone and added dropwise to 25 ml of ice water. The solution of coumarin is slowly added dropwise at 0° C. into the suspension obtained. The pH value is maintained at 8-9 by the addition of 5% sodium hydroxide.

After addition is completed, it is stirred for another 10 min at 0° C. The reaction mixture is heated to room temperature and mixed dropwise with a solution of 55 mg of taurine in 4 ml of water. During addition, the temperature is solely increased to 40-45° C. and the pH value maintained at 8-9 by the addition of 5% sodium hydroxide. The reaction mixture is maintained for 30 min at 45° C. Another 70 mg of taurine are dissolved in water and added. The temperature of the reaction mixture is increased for 1 h to 85-90° C. The reaction mixture is purified by chromatography. Yield: 78%; HPLC-MS: MH$^+$=559.09

What is claimed is:

1. Compounds of the general formulae (I)-(IV)

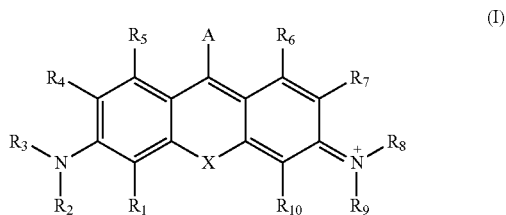

(I)

-continued

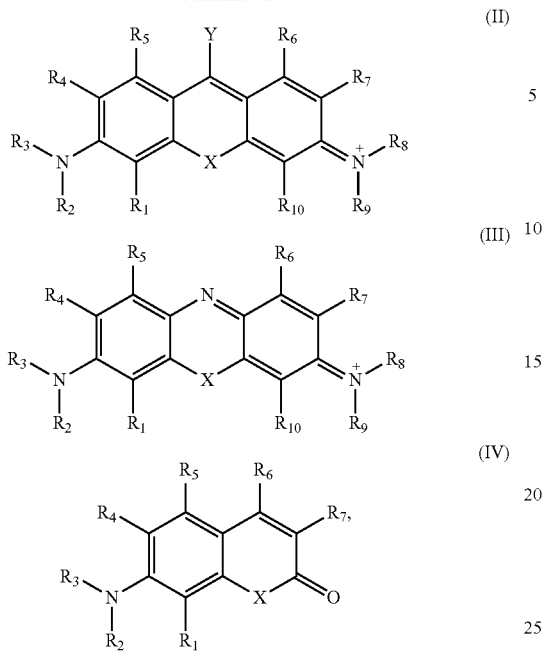

in which $R_1$, $R_4$, $R_5$, $R_6$, $R_7$, and $R_{10}$ independently of one another mean hydrogen, halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$ or a hydrocarbon group having 1-20 C atoms, wherein the hydrocarbon group optionally comprises one or more heteroatoms selected from the group consisting of N, O, and S or/and one or more substituents preferably selected from the group consisting of halogen, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, $R_2$, $R_3$, $R_8$, and $R_9$ independently of one another mean hydrogen or a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, wherein each of the moieties in the compounds of the general formulae (I)-(IV) can form a ring system with one or more adjacent moieties, X in the general formula (I) means a group selected from O, S, $SO_2$, $CR_{11}R_{12}$ or $SiR_{13}R_{14}$, X in the general formula (II) means a group selected from O, S, $CR_{11}R_{12}$, $SiR_{13}R_{14}$ or $NR_{15}$, X in the general formula (III) means a group selected from O, S or $CR_{11}R_{12}$, X in the general formula (IV) means O or $NR_{15}$, and wherein $R_{11}$, $R_{12}$, $R_{13}$, $R_{14}$ and $R_{15}$ independently of one another mean hydrogen, CN, COOH, COO(alkyl), COO(aryl), $PO_3H_2$, $SO_3H$ or a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, or $R_{11}$ and $R_{12}$ or $R_{13}$ and $R_{14}$ in each case together with the atom to which they are attached, form a 3- to 7-membered ring, wherein the ring can comprise one or more double bonds or/and one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$ and a hydrocarbon group having 1-20 C atoms or/and can be annulated with one or more 3- to 7-membered rings, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, and $SO_3H$, A in the general formula (I) means an aryl or heteroaryl moiety, which optionally comprises one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), CONH(alkyl), $CON(alkyl)_2$, CONH(aryl), $CON(aryl)_2$, $PO_3H_2$, $SO_3H$ and a hydrocarbon group, wherein the hydrocarbon group itself optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, Y in the general formula (II) means hydrogen, CN, COOH, COO(alkyl), COO(aryl), $NHR_{16}$, $NR_{17}R_{18}$, $PO_3H_2$, $SO_3H$ or an aliphatic hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, and $R_{16}$, $R_{17}$, and $R_{18}$ independently of one another mean hydrogen, CN, COOH, COO(alkyl), COO(aryl), $PO_3H_2$, $SO_3H$ or a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, or $R_{17}$ and $R_{18}$ together with the atom to which they are attached, form a 3- to 7-membered ring, wherein the ring can comprise one or more double bonds or/and one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$ and a hydrocarbon group having 1-20 C atoms or/and can be annulated with one or more 3- to 7-membered rings, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, provided that at least one of the moieties $R_2$, $R_3$, $R_8$ or $R_9$ has the structure B, wherein B has one of the following isomeric structures (H), (I) or (J)

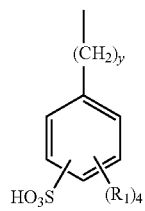

(H)

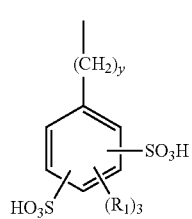

(I)

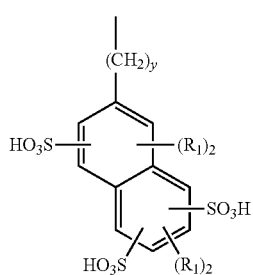

(J)

wherein y is 0, 1, 2, 3, 4, 5, 6, or, wherein B has one of the structures (K) or (L), wherein x is 1, 2, 3, 4, 5, or 6

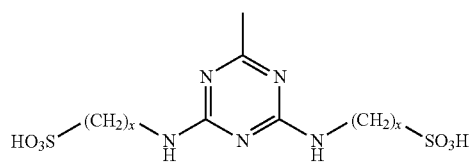

(K)

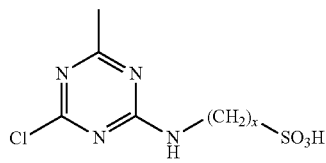

(L)

or, wherein B represents $—CH_2SO_3H$ or $—CH_2CH_2SO_3H$;

wherein structure B is not integrated within a ring system with one or more adjacent moieties, wherein in compounds of the general formula (I) for X=O the moiety B is not $—CH_2SO_3H$ or $—CH_2CH_2SO_3H—$, unless at the same time at least one or more of the moieties $R_1$, $R_4$, $R_5$, $R_6$, $R_7$, $R_{10}$ and/or A comprises at least one further $SO_3H$ group.

2. The compounds of the general formulae (I)-(IV) according to claim 1, wherein $R_1$ and $R_2$, $R_3$ and $R_4$, $R_7$ and $R_8$ or/and $R_9$ and $R_{10}$ together with the atoms to which they are attached, form a 5- or 6-membered ring, wherein the ring can comprise one or more double bonds or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$ and a hydrocarbon group having 1-20 C atoms, wherein the hydrocarbon group optionally comprises one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, and $SO_3H$.

3. The compounds of the general formulae (I)-(IV) according to claim 1, wherein at least one 5- or 6-membered ring is substituted with one or more hydrocarbon groups having 1-20 C atoms, wherein the hydrocarbon group(s) optionally comprise(s) one or more substituents selected from the group consisting of COOH, COO(alkyl), COO(aryl) and $SO_3H$.

4. The compounds of the general formulae (I)-(IV) according to claim 1, wherein the rings have one of the following structures (C), (C') (D), (E), (E'), (F) or (G)

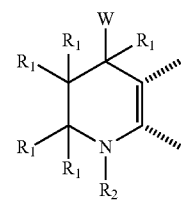

(C)

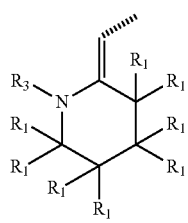

(D)

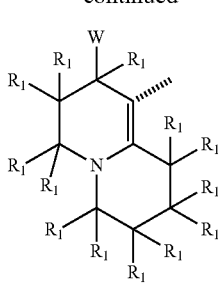 (E)

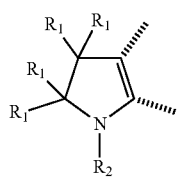 (F)

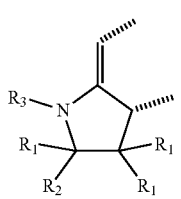 (G)

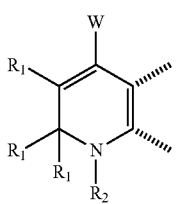 (C′)

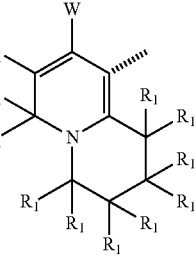 (E′)

with W=H, CH$_3$ or CH$_2$SO$_3$H.

5. The compounds of the general formulae (I)-(IV) according to claim 1, wherein X=O.

6. The compounds of the general formulae (I)-(III) according to claim 1, wherein X=CR$_{11}$R$_{12}$, wherein R$_{11}$ and R$_{12}$ independently of one another mean hydrogen or a hydrocarbon group having 1-20 C atoms, in particular an alkyl group having 1-6 C atoms.

7. The compounds of the general formulae (I) and (II) according to claim 1, wherein X=SiR$_{13}$R$_{14}$, wherein R$_{13}$ and R$_{14}$ independently of one another mean hydrogen or a hydrocarbon group having 1-20 C atoms, in particular an alkyl group having 1-6 C atoms.

8. The compounds of the general formula (I) according to claim 1, characterized in that A has one of the following partially isomeric structures (M), (N), (O), (P), (Q)

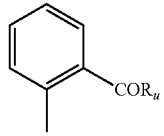 (M)

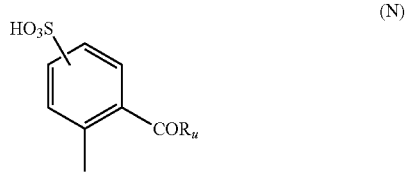 (N)

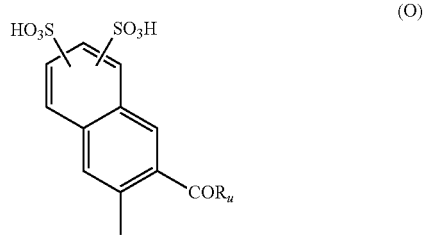 (O)

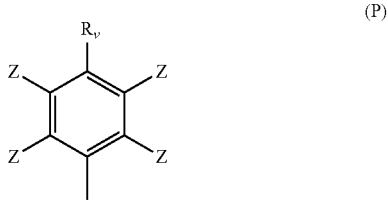 (P)

 (Q)

wherein E represents a group selected from O, S, N or $^+$NR$_{19}$,

R$_u$=halogen, OR$_{20}$, NHR$_{21}$, NR$_{22}$R$_{23}$,

Z is selected from hydrogen or halogen,

R$_v$=Z, S(CH$_2$)$_x$COOH, S(CH$_2$)$_x$SO$_3$H, NHR$_{24}$, NR$_{25}$R$_{26}$ and R$_w$=H, alkyl, (CH$_2$)$_x$COOH, (CH$_2$)$_x$SO$_3$H with x=1, 2, 3, 4, 5, 6, R$_{19}$ and R$_{20}$ independently of one another mean hydrogen or a hydrocarbon group having 1-20 C atoms, wherein the hydrocarbon group optionally contains one or more heteroatoms selected from the group consisting of N, O and S or/and one or more substituents preferably selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, and $R_{21}$, $R_{22}$ and $R_{23}$ as well as $R_{24}$, $R_{25}$ and $R_{26}$ are defined exactly as $R_{16}$, $R_{17}$ and $R_{18}$ and positions not further specified are defined as $R_1$.

9. The compounds of the general formula (II) according to claim 1, wherein Y is hydrogen, CN, $CF_3$, $NHR_{16}$, $NR_{17}R_{18}$, $(CF_2)_x COOH$ with x=1, 2, 3, 4, 5, 6, or the isomeric structure (T)

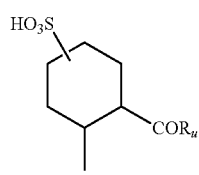 (T)

wherein $R_u$=halogen, $OR_{20}$, $NHR_{21}$, $NR_{22}R_{23}$ and positions not further specified are defined as $R_1$.

10. A method for a qualitative or/and quantitative determination of an analyte in a sample, comprising coupling a compound of the general formulae (I)-(IV) according to claim 1 to the analyte.

11. The method according to claim 10, further comprising coupling the compound of the general formulae (I)-(IV) to a component of a detection reagent or/and to a carrier.

12. The method of claim 10, wherein the compound of the general formula (I)-(IV) is coupled to the analyte by a covalent bond.

13. Conjugate from a compound of the general formulae (I)-(IV) according to claim 1 and a binding partner.

14. Conjugate according to claim 13, wherein the binding partner is selected from lipids, peptides, polypeptides, nucleic acids, nucleosides, nucleotides, nucleic acid analogs, and haptens.

15. The compounds of the general formulae (I)-(IV) according to claim 1, wherein group B represents a residue selected from

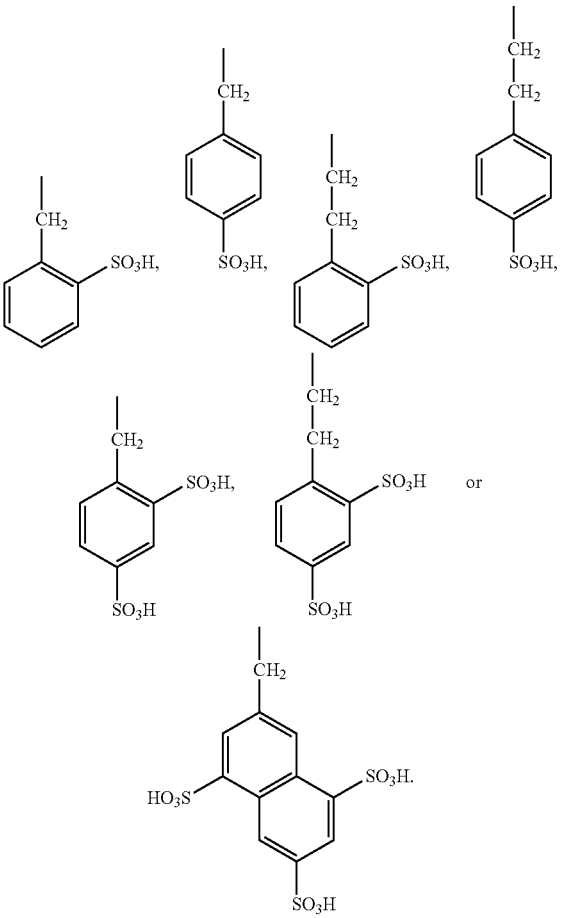

* * * * *

UNITED STATES PATENT AND TRADEMARK OFFICE
CERTIFICATE OF CORRECTION

PATENT NO. : 11,180,657 B2
APPLICATION NO. : 16/145597
DATED : November 23, 2021
INVENTOR(S) : Norbert Kemnitzer et al.

Page 1 of 3

It is certified that error appears in the above-identified patent and that said Letters Patent is hereby corrected as shown below:

In the Claims

In Column 114, Line 47, in Claim 4, delete "(C′)" and insert -- (C′), --.

In Column 114, Lines 58-67, in Claim 4, delete " 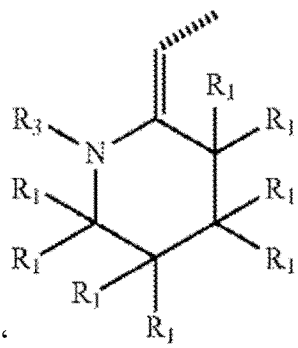 " and insert -- 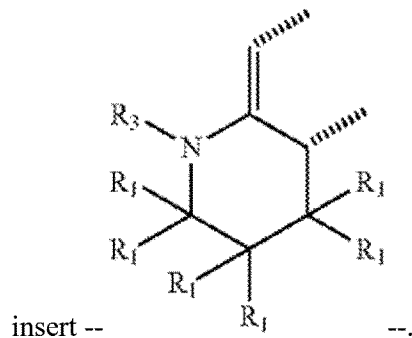 --.

Signed and Sealed this
Seventeenth Day of May, 2022

*Katherine Kelly Vidal*
Katherine Kelly Vidal
*Director of the United States Patent and Trademark Office*

In Column 115, Lines 3-12, in Claim 4, delete " 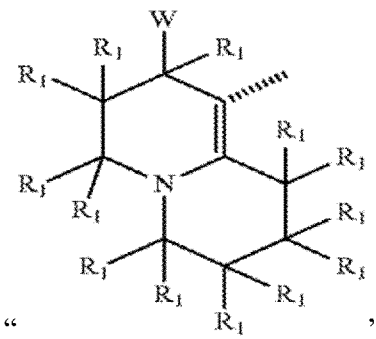 " and
insert -- 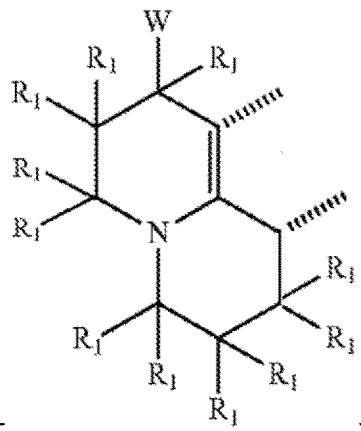 --.
In Column 115, Lines 25-33, in Claim 4, delete " 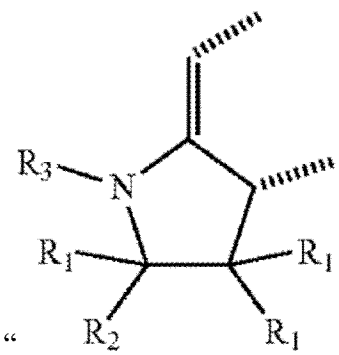 " and
insert -- 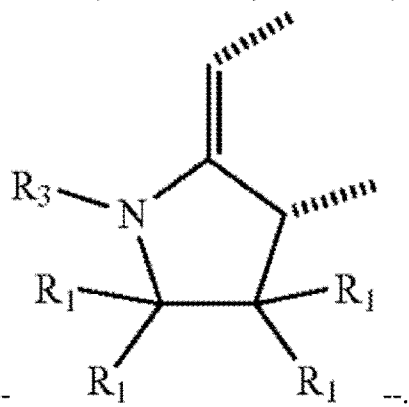 --.

CERTIFICATE OF CORRECTION (continued)
U.S. Pat. No. 11,180,657 B2

In Column 115, Lines 46-55, in Claim 4, delete " 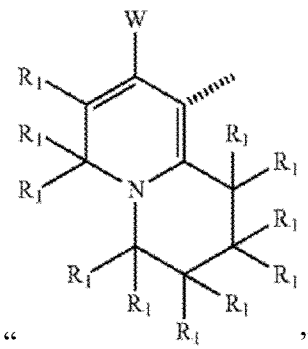 " and insert -- 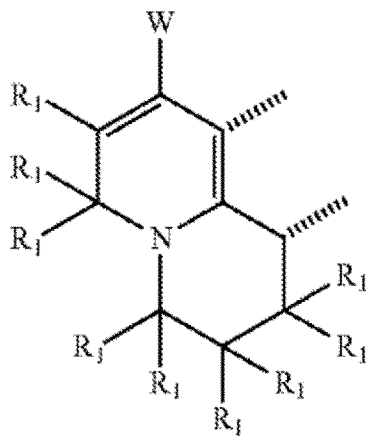 --.